US007067486B2

(12) United States Patent
Soreq et al.

(10) Patent No.: US 7,067,486 B2
(45) Date of Patent: Jun. 27, 2006

(54) ACETYLCHOLINESTERASE-DERIVED PEPTIDES AND USES THEREOF

(75) Inventors: Hermona Soreq, Jerusalem (IL); Amiram Eldor, deceased, late of Tel Aviv (IL); by Sofia Eldor, legal representative, Tel Aviv (IL); Varda Deutch, Jerusalem (IL); Dan Grisaru, Hertzlia (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 353 days.

(21) Appl. No.: 09/998,042

(22) Filed: Nov. 30, 2001

(65) Prior Publication Data

US 2003/0036632 A1    Feb. 20, 2003

Related U.S. Application Data

(63) Continuation-in-part of application No. PCT/IL00/00311, filed on May 31, 2000.

(30) Foreign Application Priority Data

| May 31, 1999 | (IL) | ................................. 130224 |
| Sep. 2, 1999 | (IL) | ................................. 131707 |

(51) Int. Cl.
    *A61K 38/00*     (2006.01)
(52) U.S. Cl. .............................. 514/12; 514/2; 530/324
(58) Field of Classification Search ...................... None
    See application file for complete search history.

(56) References Cited

U.S. PATENT DOCUMENTS 6,258,780 B1 * 7/2001 Soreq et al. ................... 514/12

FOREIGN PATENT DOCUMENTS

| WO | WO9108302 | 6/1991 |
| WO | WO9822132 | 5/1998 |

OTHER PUBLICATIONS

A. Deutch et al., ARP—a novel hematopoietic growth factor and stress signal derived from acetylcholinesterase, *Blood*, 94:46A (Abstract 193, poster session 193-I) (1999).
M.A.R. Ibrahim and J. Gaál, Effects fo Seminal Plasma Cholinesterase on the Viability and Freezing Properties of Bull Spermatozoa, *Acta Vererinaria Academia Scientarium Hungaricae*, 27(4):403-407 (1979).
N. Perdon, Choliensterase Activity of Semical Plasma and Human Spermatozoa in Normal and Infertile Subjects, *Arch. Androl.*, 10(3):249-251 (1980).
J.-M Pallus et al., Mouse Megakaryocytes Secrete Acetylcholinesterase, *Blood*, 58:1100-1106 (1981).

M. Sternfield et al., Acetylcholinesterase Enhances Neurite Growth and Synapse Development Through Alternative Contributions of its Hydrolitic Capacity, Core Protein, and Variable C. Termini, *J. Neurosci.*, 18(4):1240-1249 (1998).
T. Battaini et al., Protein Kinase C Anchoring Deficit in Postmortem Brains of Alzheimer's Disease Patients, *Exp Neurol*, 159:559-564 (1999).
M. Cardell and T. Wieloch, Time Course of the Translocation and Inhibition of Protein Kinase C During Complete Cerebral Ischemia in the Rat, *J Neurochem*, 61:1308-1314 (1993).
B. Y. Chang et al., RACK1, a Receptor for Activated C Kinase and a Homology of the β Subunit of G Proteins, Inhibits Activity of Src Tyrosine Kinases and Growth of NIH 3T3 Cells, *Mol Cell Biol*, 18:3245-3256 (1998).
M. Davis et al., Neurotransmission in the rat amygdale related to fear and anxiety, *Trends Neurosci*, 17:208-214 (1994).
M. Disatnik et al., Phospholipase C-γ1 binding to intracellular receptors for activated protein kinase C, *Proc Natl Acad Sci USA*, 91:559-563 (1994).
G. I. Gallicano et al., PKC—a pivotal regulator of early development, *Bioassay*, 19:29-36 (1997).
J. Gorman et al., Neuronanatomical Hypothesis of Panic Disorder, Revised, *Am J Psychiatry*, 157:493-505 (2000).
M. Grifman et al., Functional redundancy of acetylcholinesterase and neuroligin in mammalian neuritogenesis, *Proc Natl Acad Sci USA*, 95:13935-13940 (1998).

(Continued)

*Primary Examiner*—Bruce R. Campell
*Assistant Examiner*—B. Dell Chism
(74) *Attorney, Agent, or Firm*—John P. White, Esq.; Cooper & Dunham LLP

(57) ABSTRACT

The invention relates to a cell growth and/or differentiation regulatory peptide comprising a sequence of about 9 to about 150 amino acids derived from acetylcholinesterase amino acid sequence, preferably from the C-terminal region of acetylcholinesterase. The invention also relates to pharmaceutical compositions comprising the peptides, particularly for use in promoting survival of stem cells, promoting differentiation of stem cells, promoting growth of stem cells and/or promoting the growth-enhancing effect of a growth factor on stem cells, alone, or in combination with other growth factors. Of particular interest is the use of the peptides in the treatment of thrombocytopenia, post-irradiation conditions, post-chemotherapy conditions, or conditions following massive blood loss and promotion of neural progenitors in use for cell therapies aimed at restoring neural functions in diseased individuals. Further, the invention relates to antibodies against the peptides, inter alia for diagnostic use, for example, the diagnosis of stress-induced male infertility. The invention also relates to in vitro and in vivo methods for screening of drugs that affect the central nervous system, and are potential modulators of interactions between the "readthrough" form of acteylcholinesterase, AChE-R, the intracellular receptor RACK1 and the kinase PKC.

15 Claims, 30 Drawing Sheets

OTHER PUBLICATIONS

J. P. Herman and W. E. Cullinan, Neurocircuitry if stress: central control of the hypothalamo-pituitary-adrenocortical axis, *Trends Neurosci*, 20:78-84 (1997).

D. A. Hoffman and D. Johnston, Downregulation of Transient K$^+$ Channels in Dendrites of Hippocampal CA1 Pyramidal Neurons by Activation of PKA and PKC, *J Neurosci*, 18:3521-3528 (1998).

J. Liliental and D. D. Chang, Rack1, a Receptor for Activated Protein Kinase C, Interacts with Integrin β Subunit, *J Biol Chem*, 273:2379-2389 (1998).

R. K. McNamara et al., Differential Subcellar Redistribution of Protein Kinase C Isozymes in the Rat Hippocampus Induced by Kainic Acid, *J Neurochem*, 72:1735-1743 (1999).

D. Paola et al., Oxidative Stress Induced Increase in Intracellular Amyloid β-Protein Production and Selective Activation of βI and βII PKCs in NT2 Cells, *Biochem Biophys Res Commun*, 268:642-646 (2000).

E.D. Roberson et al., The Mitogen-Activated Protein Kinase Cascade Copules PKA and PKC to cAMP Response Element Binding Protein Phosphorylation in Area CA1 and Hippocampus, *J Neurosci*, 19:4337-4348 (1999).

M. M. Rodriguez et al., RACK1, a Protein Kinase C Anchoring Protein, Coordinates of Binding of Activated Protein Kinase C and Select Pleckstrin Homology Domains in Vitro, *Biochemistry*, 38:13787-13794 (1999).

D. Ron et al., Coordinated movement of RACK1 with Activated βIIPKC, *J. Biol Chem*, 274:27039-27046 (1999).

F. Tronche et al., Disruption of the glucocorticoid receptor gene in the nervous system results in reduced anxiety, *Nat Genet*, 23:99-103.

W. J. Weeber et al., A Role for the β Isoform of Protein Kinase C in Fear Conditioning, *J Neurosci*, 20:5906-5914 (2000).

L. Xu et al., Behavioural stress facilitates the induction of long-term depression in the hippocampus, *Nature*, 387:497-500 (1997).

S. J. Yarwood et al., The RACK1 Signaling Scaffold Protein Selectively Interacts with the cAMP-specific Phosphodiesterase PDE4D5 Isoform, *J Biol Chem*, 274:14909-14917 (1999).

\* cited by examiner

ASP　　　ARP　　　sal　　　in AS3　　　AS3

*Figure 10A*
PVE
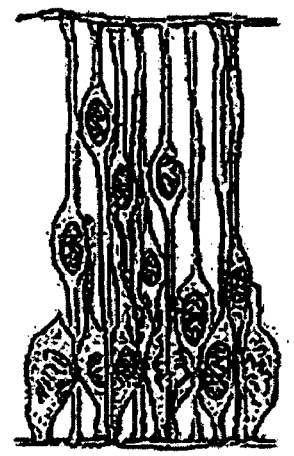
Venticular Lumen
*Figure 10B*
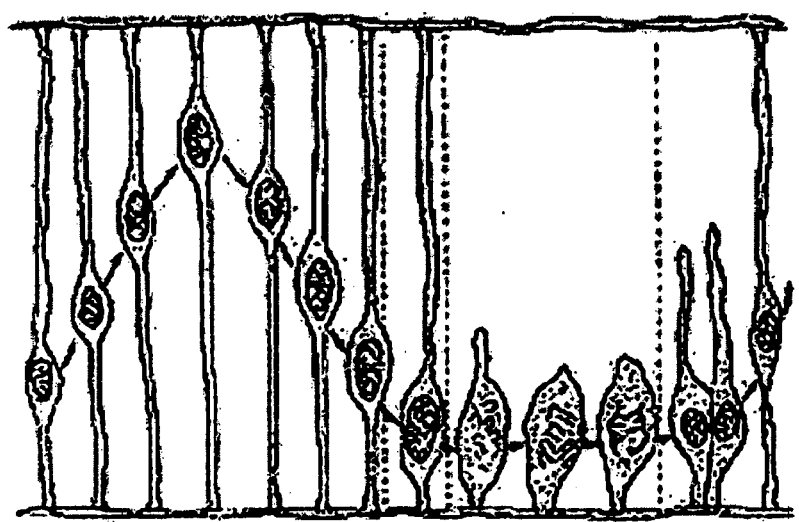
Venticular Lumen Figure 17A
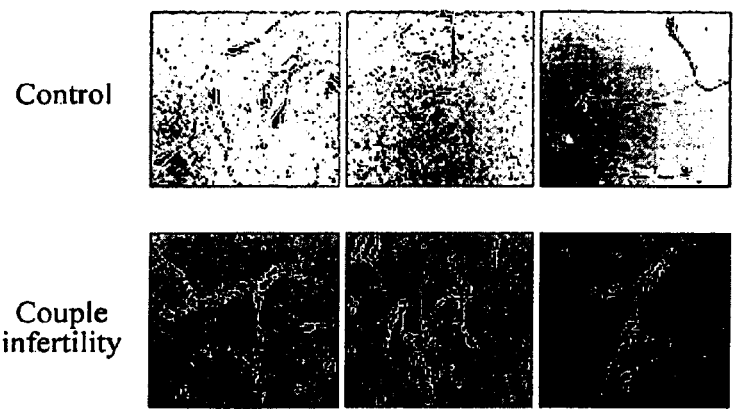
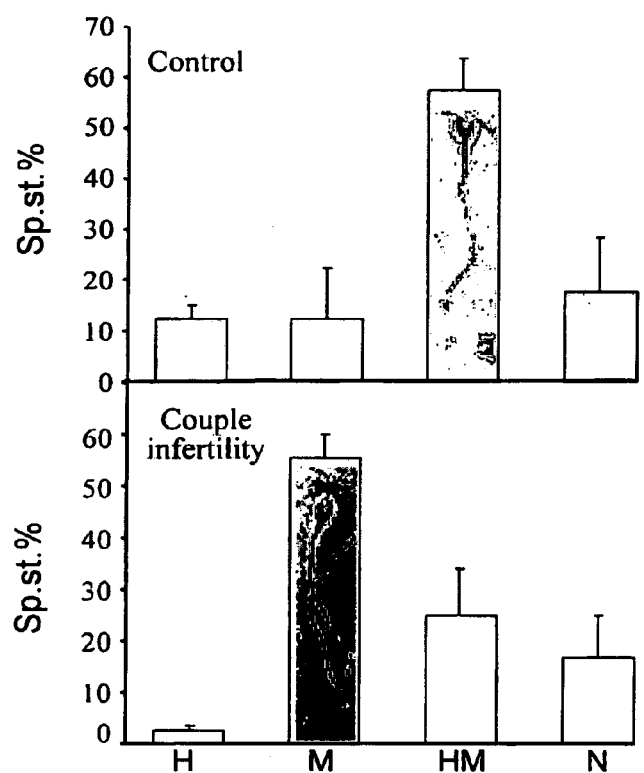
Figure 17B

*Figure 18B*

```
          10         20         30         40         50         60
MTEQMTLRGTLKGHNGWVTQIATTPQFPDMILSASRDKTIIMWKLTRDETNYGIPQRALR
          70         80         90        100        110        120
GHSHFVSDVVISSDGQFALSGSWDGTLRLWDLTTGTTRRFVGHTKDVLSVAFSSDNRQI
         130        140        150        160        170        180
VSGSRDKTIKLWNTLGVCKYTVQDESHSEWVSCVRFSPNSSNPIIVSCGWDKLVKVWNLA
         190        200        210        220        230        240
NCKLKTNHIGHTGYLNTVTVSPDGSLCASGGKDGQAMLWDLNEGKHLYTLDGGDIINALC
         250        260        270        280        290        300
FSPNRYWLCAATGPSIKIWDLEGKIMVDELKQEVISTSSKAEPPQCTSLAWSADGQTLFA
         317
GYTDNLVRVWQVTIGTR
```

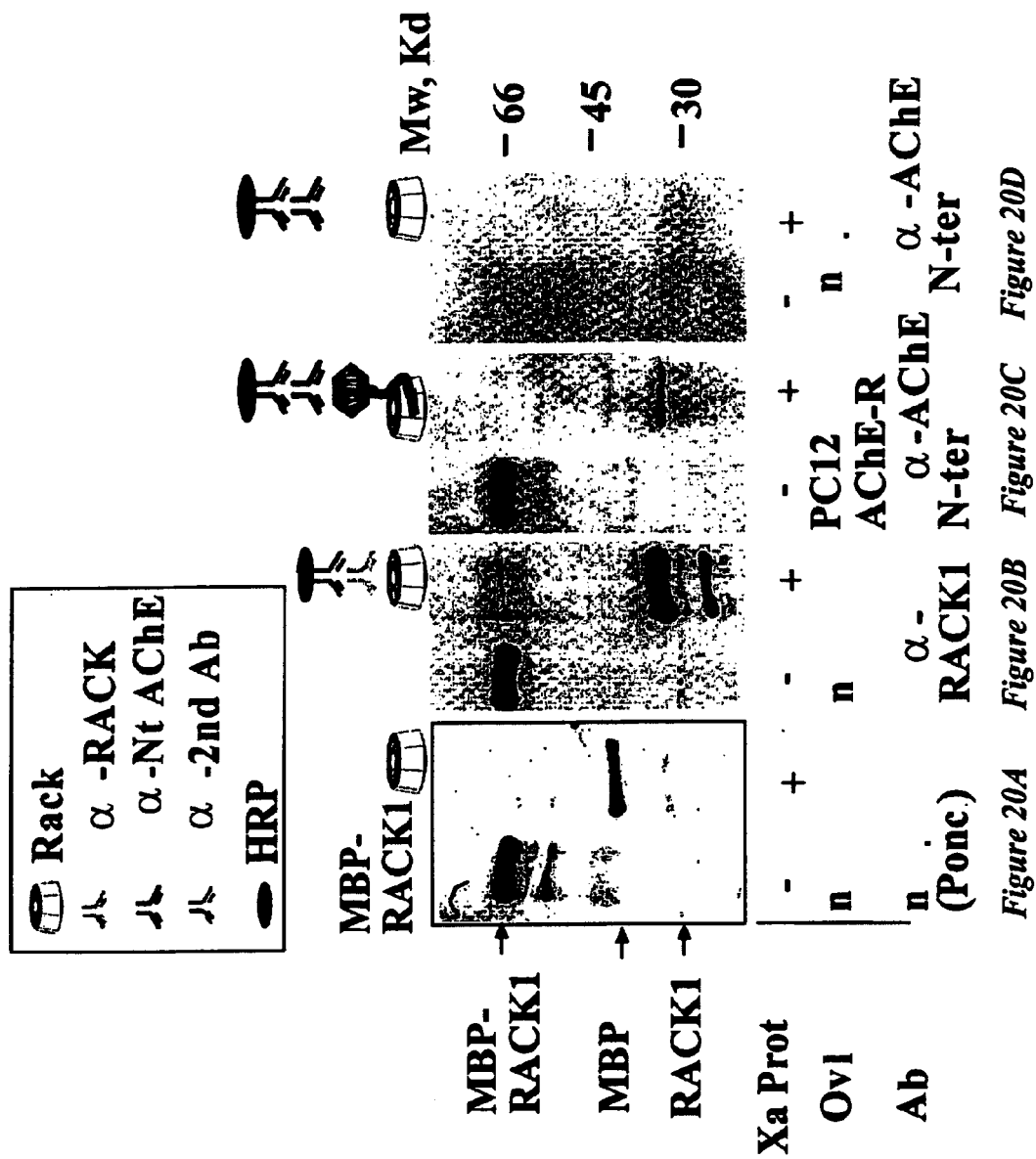

RACK1

AChE-R

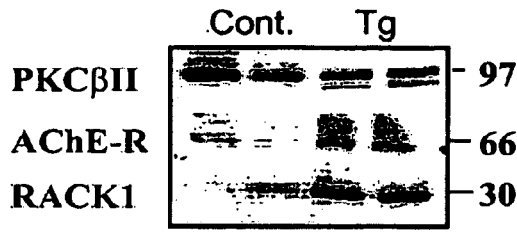
*Figure 25A*
*Figure 25B*
*Figure 25C*
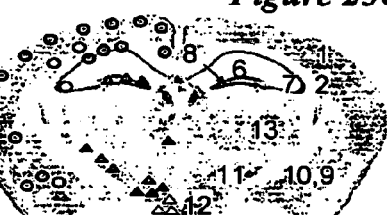
ACHE-R +PKCβII
o +
o ++
o +++
ACHE-R
▲ +
▲ ++
▲ +++
*Figure 25D*
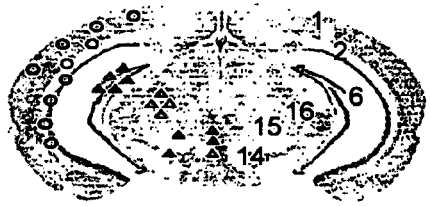
*Figure 25E*

ACETYLCHOLINESTERASE-DERIVED PEPTIDES AND USES THEREOF

CROSS-REFERENCE TO RELATED APPLICATIONS

This application is a continuation-in-part application of international patent application PCT/IL00/00311 filed May 31, 2000.

STATEMENT AS TO FEDERALLY SPONSORED RESEARCH

This work was supported by the US Army Medical Research and Material Command DAMD 17-99-9547 (July 1999–August 2004) and the Defense Advance Research Project Agency DARPA N66001-01-C-8015 (May 2001–May 2004). The U.S. Government therefore has certain rights in this invention.

FIELD OF THE INVENTION

The invention is directed to the field of stem cell survival and expansion. Specifically, the invention is directed at the stem cell survival and expansion effects of peptides derived from acetylcholinesterase. In addition, the invention relates to a system for screening of nervous system drugs that are directed to central nervous system conditions or disorders. More specifically, the invention relates to the screening of modulators of the AChE-R-PKCβII-RACK1 complex.

BACKGROUND OF THE INVENTION

Stress insults evoke a plethora of responses in the organism, affecting the functioning of various systems.

In the hematopoietic system, stress insults are associated with rapid and significant changes in blood cell composition. For example, following massive blood loss, or after surgery, the hematopoietic system responds within hours, by an elevation of the white blood cell and platelet counts. However, the mechanisms responsible for initiating this adjustment are not fully understood. Glucocorticoid hormones, known to be elevated under stress, play a leading role in the adaptive reaction of the bone marrow in response to stress. Glucocorticoid hormones induce absolute increases in all hematopoietic lineages, especially myeloid cells. This involves a cascade of events culminating in changes in the proliferation, differentiation and apoptotic events characteristic of each of the hematopoietic cell lineages [Lansdorp (1995) *Exp. Hematol.* 23, 187–91]. Also, significant changes occur under glucocorticoid hormones in the levels of hematopoietic growth factors controlling the proliferation of stem cells from which blood cells develop.

Hematopoietic stem cells (HSCs) are pluripotent, in that they give rise to all blood cell lineages. These cells migrate during ontogeny to settle in the bone marrow as a permanent self-renewing source of blood cells. Under normal conditions the vast majority of HSCs are nondividing, but under conditions of development or stress they can undergo clonal expansion and self-renewal [Keller and Snodgrass (1990) *J. Exp. Med.* 171, 1407–18]. A large number of cytokines and growth factors, such as stem cell factor (SCF), thrombopoietin (TPO), and FLT-3 ligand, are thought to mediate the proliferative capacity of HSCs, through specific receptors, c-kit, c-mpl and flt3/flk-2, respectively. Alone, their capacity to stimulate proliferation is limited. For example, SCF can maintain survival for a few days in vitro, but not the self-renewal of HSCs (Li and Johnson, Blood 84, 408–14, 1994). However, when used in combination, these growth factors acquire a potent co-stimulatory effect. The early phase of adaptation of the hematopoietic system to stress (first 24 hr), requires coordinator(s), such as leu-enkephalin, which modulate the effects of growth factors on stem cells. However, leu-enkephalin is present in the circulation only immediately following the stress insult, whereas the modulation of hematopoiesis continues long after that phase. Therefore, additional long-acting modulators remain to be identified.

The enzyme acetylcholinesterase (AChE) is expressed in brain tissue, but also in most, if not all, of the mammalian hematopoietic cell lineages. AChE is expressed in many parts of the vertebrate embryo, with a developmentally regulated pattern in specific cell types and tissues during the embryonic and adult stages. AChE diversity is noted in several pathological states, such as Alzheimer's disease, where AChE activity was shown to decrease, not only in the primary site of the disease, the brain, but also in the hematopoietic system.

It has now surprisingly been found that the C-terminal peptides of AChE-S and AChE-R have independent biological activities. Specifically, it has been found that these peptides promote stem cell survival. It has also been found that these peptides promote stem cell expansion, when used in combination with growth factors. Further, it has been found that such peptides are capable of augmenting hematopoiesis in vivo.

In the central nervous system (CNS), physiological stress induces rapid and robust signaling processes in mammalian brain neurons. These processes are known to suppress long term potentiation (LTP) [Vereker, E. et al. (2000) *J Neurosci*, 20, 6811–9], augment long term depression (LTD) [Xu, L. et al. (1997) *Nature*, 387, 497–500], and induce release of synaptic vesicles, potentiating neurotransmission [Stevens, C. F. and Sullivan, J. M. (1998) *Neuron*, 21, 885–93]. At the long term, stress-induced signaling attenuates the stress response, enabling the organism to be less excessively affected by a stressful event. This induces neuronal dendrite branching [Sousa, N. et al. (2000) Neuroscience, 97, 253–66] and synapse re-organization [McEwen, B. S. (1999) *Ann Rev Neurosci*, 22, 105–22]. However, the molecular pathway(s) leading from short to long term processes and which enable the adjustment to stressful stimuli, are not yet known.

Ample information suggests the involvement of specific protein kinases in at least some of these stress-induced processes. The enzymatic activity of certain subtypes of protein kinase C (PKC) [Coussens, L. et al. (1986) *Science*, 233, 859–66] was shown to be subject to changes (i.e. biochemical activation, membrane translocation) under physiological [Hu, G. Y. et al. (1987) *Nature*, 328, 426–9], biochemical [Macek, T. A. et al. (1998) *J Neurosci*, 18, 6138–46] and cytoarchitectural [Tint, I. S. et al. (1992) *Proc Natl Acad Sci USA*, 89, 8160–4] responses at the cellular and organismal levels. A relevant mediator of the stress-related changes in PKC activities is likely to be largely absent from brain neurons under normal conditions, but should be induced rapidly and for long periods following stress insults.

A relevant putative mediator of the stress-related changes in PKC activities should be intracellular in its location and capable of activating or translocating active PKC within neuronal perikarya. The "readthrough" acetylcholinesterase variant AChE-R is a promising candidate for this role [Soreq, H. and Seidman, S. (2001) *Nat Rev Neurosci*, 2, 294–302]. Brain AChE-R is exceedingly rare in the adult, non-stressed brain. Various stress insults induce AChE-R overproduction through alternative splicing, creating a different C-terminal domain from that of synaptic AChE (AChE-S). AChE-R levels rise rapidly under acute psychological stress [Kaufer, D. et al. (1998) *Nature*, 393, 373–7] or chemical neurotoxication [Shapira, M. et al. (2000) *Hum Mol Genet*, 9, 1273–81] and stay elevated for over two weeks following head injury [Shohami, E. et al. (2000) *J Mol Med*, 78, 228–36]. Being a secretory protein, AChE-R fulfills the extracellular function of reducing the stress-induced acetylcholine levels. In parallel, it accumulates in neuronal cell bodies [Sternfeld, M. et al. (2000) *Proc Natl Acad Sci USA*, 97, 8647–52], where acetylcholine hydrolysis is unlikely. Transgenic mice overexpressing neuronal AChE-R, but not the normally abundant synaptic variant AChE-S, display reduced levels of stress-associated neuropathologies [Sternfeld et al. (2000) id ibid.]. This suggests distinct stress-related function(s) for the AChE-R protein. Intriguingly, the unique C-terminal domain of AChE-R does not participate in acetylcholine hydrolysis for which the core domain, common to all of the AChE variants is sufficient [Duval, N. et al. (1992) *J Cell Biol*, 118, 641–53].

Using a yeast two-hybrid screen, the inventors discovered that the C-terminal domain of AChE-R forms a tight complex with RACK1 [PCT/IL00/00311]. Interestingly, the inventors have shown that PKCβII is also part of this complex (FIG. 1), and all three proteins can be co-immunoprecipitated.

In search for the marker of the transition between short and long term processes following stress stimuli, the inventors have demonstrated that interaction with AChE-R activates PKCβII and facilitates its translocation into densely packed neuronal clusters (FIGS. 4 and 5), which may be causally involved with the stress-protection capacity of overexpressed AChE-R.

In view of these unprecedented results, it this an object of this invention to provide a method for screening of nervous system drugs that modulate the trimeric complex AChE-R/PKC/RACK1 interactions.

SUMMARY OF THE INVENTION

This invention is directed at a cell growth and/or differentiation regulatory peptide comprising a sequence of about 9 to about 150 amino acids derived from Acetylcholinesterase amino acid sequence. The said sequence preferably contains a region predicted to be rich in beta-pleated sheet structure and turns. Also preferably, the said sequence contains a predicted amphipathic helix structure. In another embodiment of the peptide of the invention, the said sequence is derived from the C-terminal region of acetylcholinesterase.

The said sequence is preferably derived from the readthrough or synaptic variant of acetylcholinesterase, preferably from the mature form thereof. The said sequence is preferably about 20 to about 70 amino acids in length. More preferably, the said sequence is SEQ ID: No. 1, SEQ ID: No. 2, SEQ ID: No. 3, SEQ ID: No.7 or SEQ ID: No.8. Still more preferably, the said peptide is SEQ ID: No. 1, SEQ ID: No. 2, SEQ ID: No. 3, SEQ ID: No. 7 or SEQ ID: No.8.

A peptide of the invention which is a cyclic peptide is also considered to be within the scope of the invention.

The peptide of the invention is preferably synthetic and preferably comprises the amino acid sequence of SEQ ID: No. 1, SEQ ID: No. 2, SEQ ID: No. 3, SEQ ID: No.7 or SEQ ID: No.8. More preferably, the peptide has the amino acid sequence denoted by SEQ ID: No. 1, 2, 3, 7 or 8. The peptide is preferably linear and synthetic.

In one embodiment, the invention provides a peptide capable of promoting cell survival and/or differentiation and comprising the amino acid sequence denoted by SEQ ID: No. 1, SEQ ID: No. 2 or SEQ ID: No. 3, and functional analogues and derivatives thereof.

In another embodiment, the invention provides a peptide of the invention which is a hematopoietic stem cell growth and/or differentiation regulatory peptide. Preferably, said peptide is capable of promoting stem cell survival and/or myeloid and megakaryocytic differentiation and comprises the amino acid sequence denoted by SEQ ID: No. 1, SEQ ID: No. 2 or SEQ ID: No. 3, or functional analogues and derivatives thereof. Said peptide may be either linear or cyclic, and is preferably synthetic.

In a still further embodiment, the invention provides a peptide thereof for use in ex vivo or in vivo expansion of hematopoietic stem cells and of neural progenitors.

The invention also provides a peptide thereof for use in ex vivo or in vivo promotion of megakaryocytic differentiation of hematopoietic stem cells.

The invention also relates to a pharmaceutical composition comprising a synthetic peptide of any one of the preceding embodiments of the invention.

The pharmaceutical composition preferably comprises a synthetic peptide comprising the amino acid sequence of SEQ ID: No. 1, SEQ ID: No. 2, or SEQ ID: No. 3. More preferably, the pharmaceutical composition comprises a synthetic peptide having the amino acid sequence denoted by SEQ ID: No. 1, SEQ ID: No. 2, or SEQ ID: No. 3. The peptide contained within the pharmaceutical composition may be either linear or cyclic, and is preferably synthetic.

The invention provides a pharmaceutical composition according to the invention, for regulating hematopoietic stem cell growth, promoting survival of stem cells, differentiation of stem cells, promoting growth of stem cells, and/or promoting the growth-enhancing effect a growth factor on stem cells. The growth factor is preferably GM-CSF, SCF, TPO, EGF or bFGF.

In a preferred embodiment of the invention, the stem cells are embryonic stem cells, nerve stem cells, epithelial stem cells, mesenchymal stem cells, or hematopoietic stem cells.

The invention provides a pharmaceutical composition comprising a peptide according to the invention for the treatment of thrombocytopenia, post-irradiation condition, post-chemotherapy condition, or condition following massive blood loss. The invention also provides said pharmaceutical composition for use in inducing synthesis of acetylcholinesterase mRNA and/or promoting the formation of hematon bodies.

In a further embodiment, the invention provides an antibody directed against a peptide of the invention. The antibody is preferably provided for use in diagnosing elevated glucocorticoid level; bone marrow stress, abnormality, dysfunction, or stressed condition, or of increased platelet count or of brain infarct risk in a mammal, or stress-induced male infertility. The antibody is preferably directed at a peptide comprising SEQ ID: No. 1, SEQ ID: No. 2, or SEQ ID: No. 3. More preferably, the antibody is directed at a peptide which is selected from SEQ ID: No. 1, SEQ ID: No. 2, or SEQ ID: No. 3.

In yet another embodiment, the invention provides a method for the diagnosis of elevated glucocorticoid level; bone marrow stress, abnormality, dysfunction or stressed condition, or of increased platelet count or of brain infarct risk in a mammal, comprising obtaining a sample from said mammal, contacting said sample with an antibody of the invention, removing unbound antibody, and detecting the extent of reaction between said antibody and acetylcholinesterase or a fragment thereof present in said sample. The said sample is preferably a serum or bone marrow sample.

In a specifically preferred embodiment, the invention provides a method for the diagnosis of stress-induced male infertility comprising obtaining a sperm cell sample from said male, smearing and drying said sperm cells, contacting said cells with an antibody of the invention, removing unbound antibody and detecting the extent of reaction between said antibody and acetylcholinesterase or a fragment thereof present in said sperm cell.

In another specifically preferred embodiment the invention provides a method for the diagnosis of stress-induced male infertility further comprising the step of determining the pattern of expression of acetylcholinesterase or a fragment thereof in said sperm cell.

In yet another embodiment, the invention provides a method for the diagnosis of stress induced male infertility for use in fertility counseling.

Another aspect of the invention relates to a method of screening for a candidate drug or substance (hereinafter the "test drug") that affects the central nervous system, wherein said test drug is a modulator of the interaction between AChE-R/RACK1/PKC, and which screening method comprises the steps of:
a. providing a reaction mixture comprising the AChE-R variant of AChE or any functional fragment thereof, the cognate receptor for activated kinase C (RACK1) and the protein kinase C II (PKCII);
b. contacting said mixture with a test drug under suitable conditions for said interaction; and
c. determining the effect of the test drug on an end-point indication, wherein said effect is indicative of modulation of said interaction by the test drug.

In this screening method, the said modulator inhibits or enhances the interaction between AChE-R/RACK1/PKC.

The reaction mixture may be a cell mixture or a cell-free mixture, and may optionally further comprise solutions, buffers and compounds which provide suitable conditions for interaction between AChE-R/RACK1/PKC and the detection of an end-point indication for said interaction. The modification of said end-point indicates modulation of the interaction between AChE-R/RACK1/PKC by said test drug.

In one embodiment of this screening method, the reaction mixture is a cell-free mixture.

In this embodiment, the screening method comprises the steps of:
a. providing a cell free mixture comprising the AChE-R variant of AChE or any functional fragment thereof, RACK1 and PKC II;
b. contacting said mixture with the test drug under conditions suitable for an in vitro interaction; and
c. determining the effect of the test drug on co-precipitation of PKC II and RACK1 with the AChE-R or fragment thereof as an end-point indication, whereby the absence or increase of said co-precipitation indicates modulation of formation of a complex between AChE-R/RACK1/PKC by the test drug.

The cell-free mixture may comprise any one of AChE-R variant of AChE or any functional fragment thereof, RACK1 and PKC II, which are provided as purified recombinant proteins or as a cell lysate of cells expressing said proteins.

The said AChE-R variant of AChE may be a fusion protein comprising AChE-R or functional fragment thereof and any one of GST (Glutathion-S-Transferase) and GFP (Green Fluorescent Protein).

In another embodiment of this screening method, the said reaction mixture is a cell mixture, particularly a transfected cell culture, and more particularly a transfected mammalian cell culture.

In this embodiment, the screening method comprises the steps of:
a. providing a transfected cell culture expressing the AChE-R variant of AChE or functional fragment thereof, the cognate receptor for activated kinase C (RACK1) and the PKC II;
b. contacting said transfected cell culture with the test drug;
c. detecting the interaction between AChE-R/RACK1/PKC in the presence of the test drug by searching for an end-point indication, whereby inhibition of said end-point indicates inhibition of complex formation between AChE-R/RACK1/PKC by said test drug.

The transfected cell to be used may be transfected by:
a. an expression vector comprising a nucleotide sequence coding for the AChE-R variant of AChE or a functional fragment thereof;
b. optionally, constructs comprising a nucleic acid sequence coding for any one of the cognate receptor for activated kinase C (RACK1) and the PKCβII.

The end-point indication may be the subcellular translocation of catalytically active PKCβII, which can be detected by a visually detectable signal.

Alternatively, the end-point indication may be co-precipitation of PKCβII and RACK1 with the AChE-R or functional fragment thereof leading to a detectable signal, whereby modification of said detectable signal in the presence of the test drug indicates modulation of the formation of a complex between AChE-R/RACK1/PKC by said test drug.

In a yet further embodiment of the screening method, the modulator of the interaction between AChE-R/RACK1/PKC also modulates the expression of RACK1 and/or PKCβII.

A further aspect of the present invention is a method for the in vivo screening of candidate drugs that affect the central nervous system, wherein said drug is a modulator of an interaction between AChE-R/RACK1/PKC, and which screening method comprises the steps of:
a. providing an AChE-R transgenic animal;
b. administering the test drug to said animal;
c. sacrificing the animal and dissecting its brain to give samples for preparation of brain extracts or for immunohistochemistry;
d. detecting the expression of RACK1 or PKCβII in said brain samples; and
e. determining the effect of the test drug on an end-point indication, wherein said effect is indicative of the in vivo modulation of said interaction by the test drug;

The end-point indication of this in vivo screening method is the expression of RACK1 and PKCβII in the brain, which can be detected by a visually detectable signal.

Preferred transgenic animals are *Xenopus* and mammals, such as mice, cows, goats, pigs and sheep. Most preferably, the transgenic animal is an AChE-R transgenic mouse, which has been described in Sternfeld et al. (2000) [Sternfeld et al. (2000) id ibid.] herein incorporated by reference.

In one embodiment of the in vivo screening method, the RACK1 or PKCβII expression can be detected by means that can detect RNA or protein.

In one specific embodiment, the RNA detection is performed by means appropriate for RNA detection, said means selected from the group consisting of RT-PCR, Northern Blot, in situ hybridization, RNAse protection and S1 nuclease analysis.

In another specific embodiment, the protein detection is performed by means appropriate for protein detection, said means selected from the group consisting of Western Blot and immunohistochemistry.

The evaluation and screening methods of the invention are suitable for assessing and screening for any test drug, e.g. test drugs selected from protein based, carbohydrates based, lipid based, nucleic acid based, natural organic based, synthetically derived organic based, antibody based and metal based substances. In preferred embodiments, the protein or antibody based substance may products of combinatorial libraries.

The drugs to be evaluated by the methods of the invention can be any candidate or known drugs, e.g. drugs for the treatment of anxiety conditions, post-traumatic stress, Alzheimer's disease, muscle malfunctioning, neurodegenerative disorders, damage resulting from exposure to xenobiotics, panic, neuromuscular disorders, Parkinson's disease, Huntington's chorea, muscle fatigue, multiple chemical sensitivity, autism, multiple sclerosis and Shorgren's disease.

In yet a further aspect, the invention provides for a method for the treatment of stress-associated conditions or disorders, for a subject in need of such treatment, said method comprising:

a. providing a composition comprising as active ingredient a modulator of an interaction between AChE-R/RACK1/PKC;

b. administering a therapeutic effective amount of said composition to said subject;

wherein said modulator is selected by the drug screening methods provided by the invention.

All the above and other characteristics and advantages of the invention will be further understood through the following illustrative and non-limitative description of preferred embodiments thereof, with reference to the appended drawings.

BRIEF DESCRIPTION OF THE FIGURES

FIG. 1A—Scheme of the ACHE Upstream Gene Sequence

Arrow indicates transcription start site, triangles, conserved transcription factor binding motifs, boxes, exons 1, 5, 6 and intron 4' as indicated, white boxes, exons 2–4 and introns 2'-3-as indicated; GRE half site (hs).

Figure 1A:
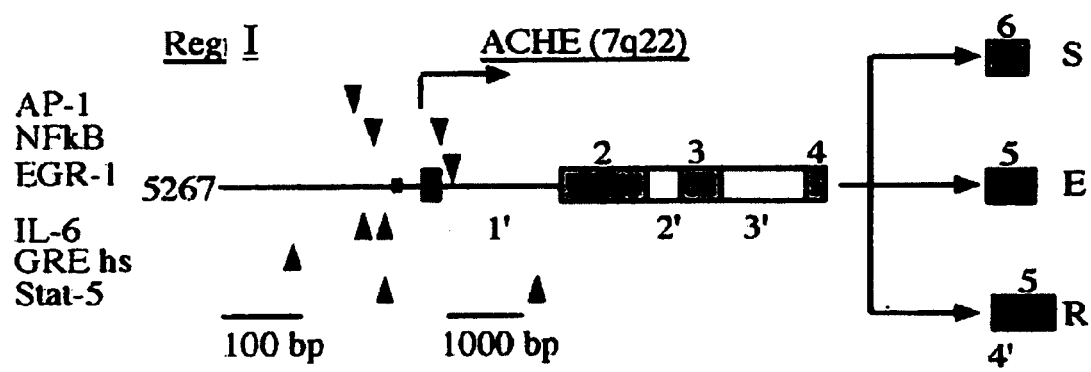
FIG. 1A–D
Figure 1B:
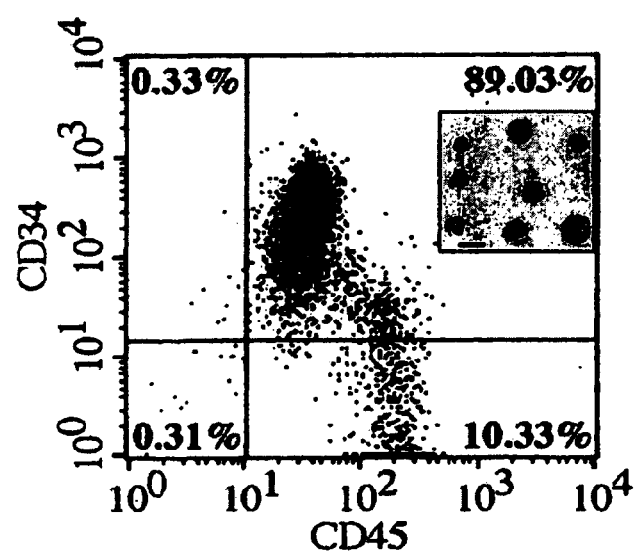

FIG. 1B—Enrichment of UCB CD34$^+$ Cells

Flow cytometry of the recovered cells, using anti CD34 and anti CD45 antibodies.

Figure 1C:
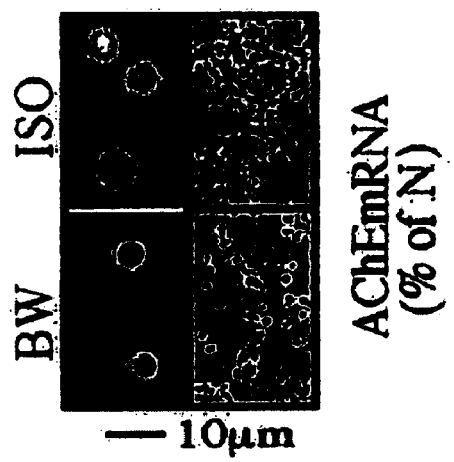

FIG. 1C—Cytochemical Staining of Enriched CD34$^+$ Cells

Cytochemical staining of enriched CD34$^+$ cells for AChE catalytic activity in the presence of inhibitors for BuChE and AChE. The inhibitors are iso-OMPA (ISO) and BW284C51 (BW). Nuclear staining (right) of the different forms of AChE was performed in the presence of different concentrations of Hydrocortisone, the AChEmRNA signal is shown as % of normal (N).

Figure 1D:
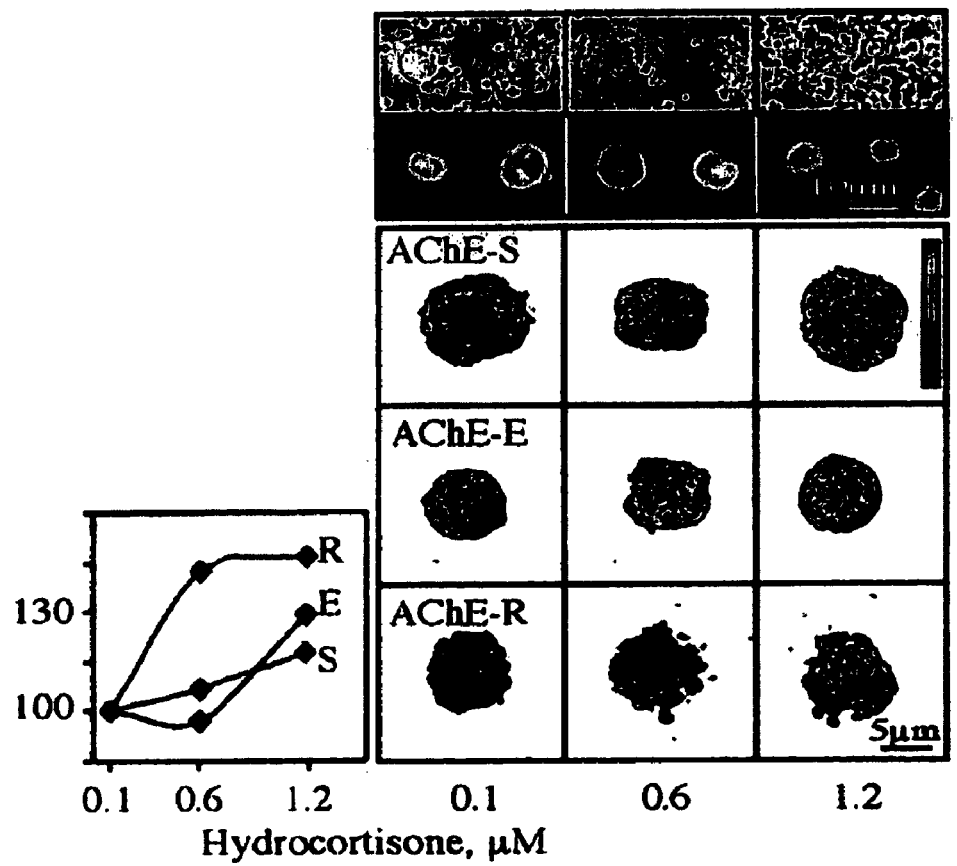

FIG. 1D—Effect of Hydrocortisone on the Expression of AChEmRNA Splicing Variants (R, H and S) in UCB CD34$^+$ Cells Upper panel shows cytochemical staining of enriched CD34$^+$ cells for AChE catalytic activity in the presence of different concentrations of Hydrocortisone. The lower panel shows in situ hybridization for detection of the different forms of AChE under different concentrations of Hydrocortisone.

Figure 2A:
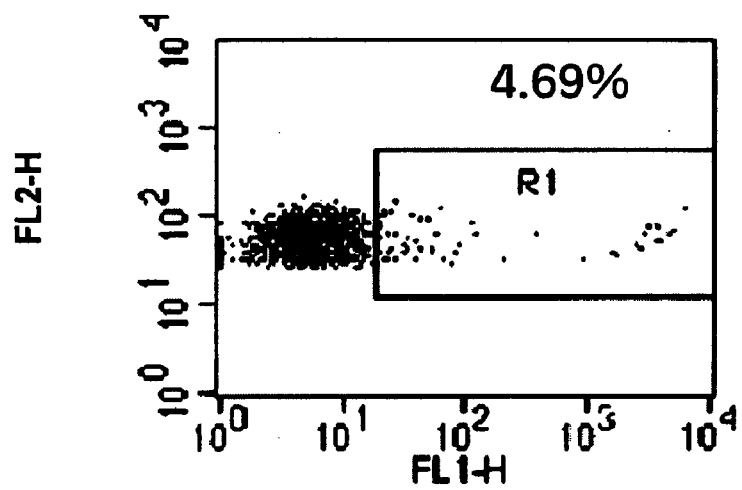
Figure 2B:
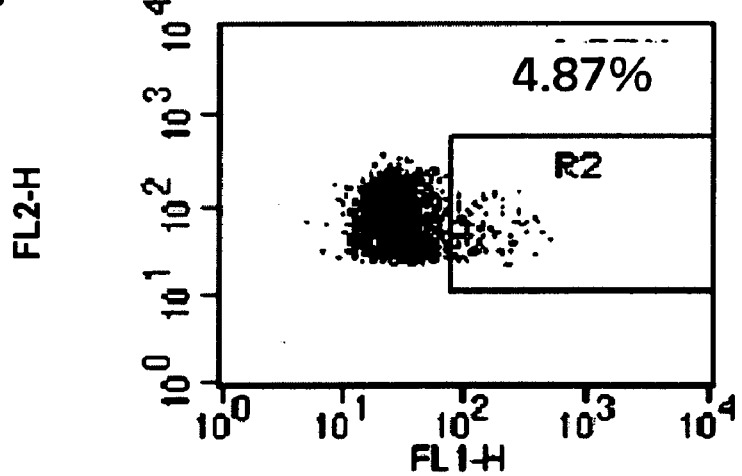

FIG. 2A–B: Expression of ARP in CD34 Cells.

FIG. 2A—shows the expression of ARP in CD34$^+$ hematopoietic cells as evaluated by flow cytometry in whole cord blood.

FIG. 2B—shows the expression of ARP in CD34$^+$ hematopoietic cells as evaluated by flow cytometry in bone marrow from a patient with immune thrombocytopenic purpura (ITP).

Cells were fixed and permeabiliazed with Fix and Perm (Caltag, Calif. and stained with moncoclonal antibodies to CD34 conjugated to pycoerythrin indicated as FL-2 and with highly specific rabbit anti-ARP antibodies followed by anti rabbit antibodies conjugated to fluoroscein isothiocyanate, indicated as Fl-1. CD34$^+$ cells were gated and 40,000 cells were analyzed for ARP expression indicated as percentage of positive cells.

Figure 3A:
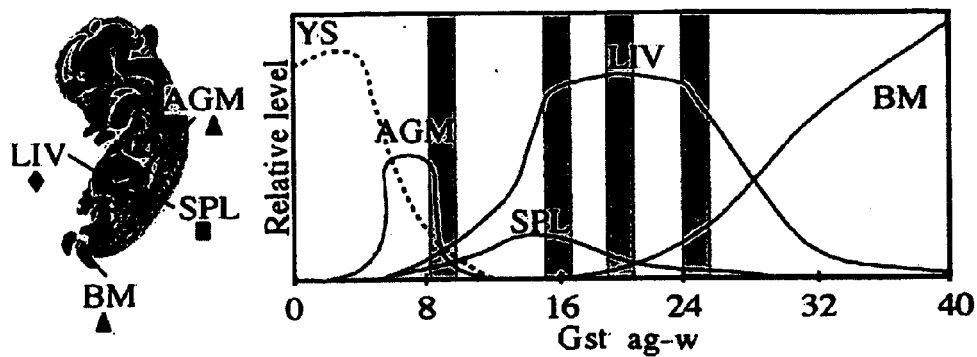
Figure 3B:
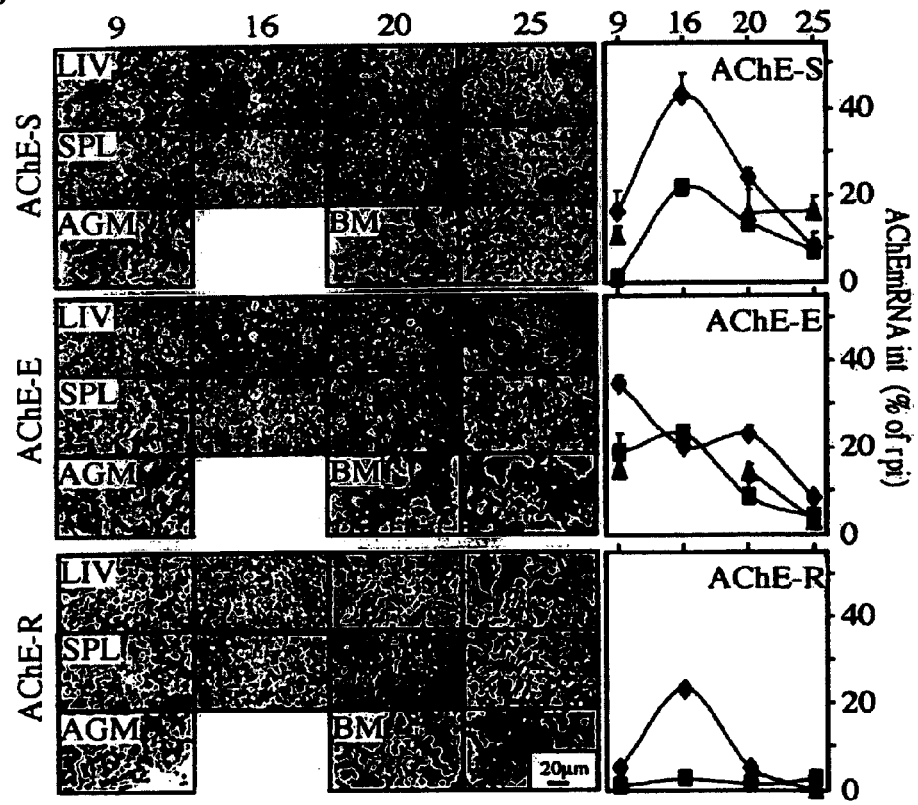

FIG. 3A–B: The Spatiotemporal Shifts in the Intensity of Embryonic AChEmRNA Transcripts through Blood Cell Forming Tissues.

FIG. 3A—shows the analysis of blood cell-forming organs—Top left: A sagittal section of a human embryo showing the hematopoietic organs-AGM (aorta-gonad-mesonephros), LIV (liver), SPL (spleen), and BM (bone marrow). Top right: Scheme of gestational shifts in hematopoietic processes in yolk sac (YS).

FIG. 3B—shows ACHE gene expression in embryonic tissues. In situ hybridization results and the average labeling intensities for the AChE-S, AChE-E and AChE-R mRNA transcripts in AGM (triangles, week 9), liver (diamonds), spleen (squares) and bone marrow (triangles, weeks 20–25) of human fetuses at different gestational ages (right side curves). The right side of the Figure shows spatiotemporal changes in labeling intensity (int) for each probe and organ as % of pixels (pi).

Figure 4A:
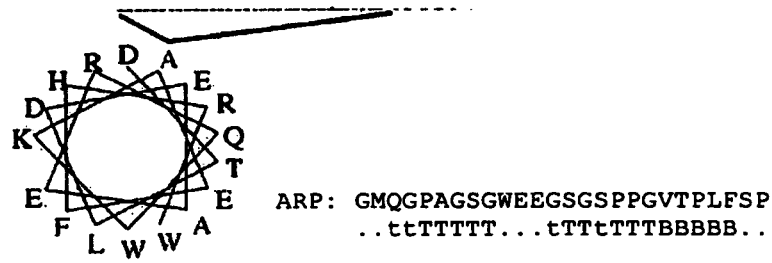
Figure 4B:
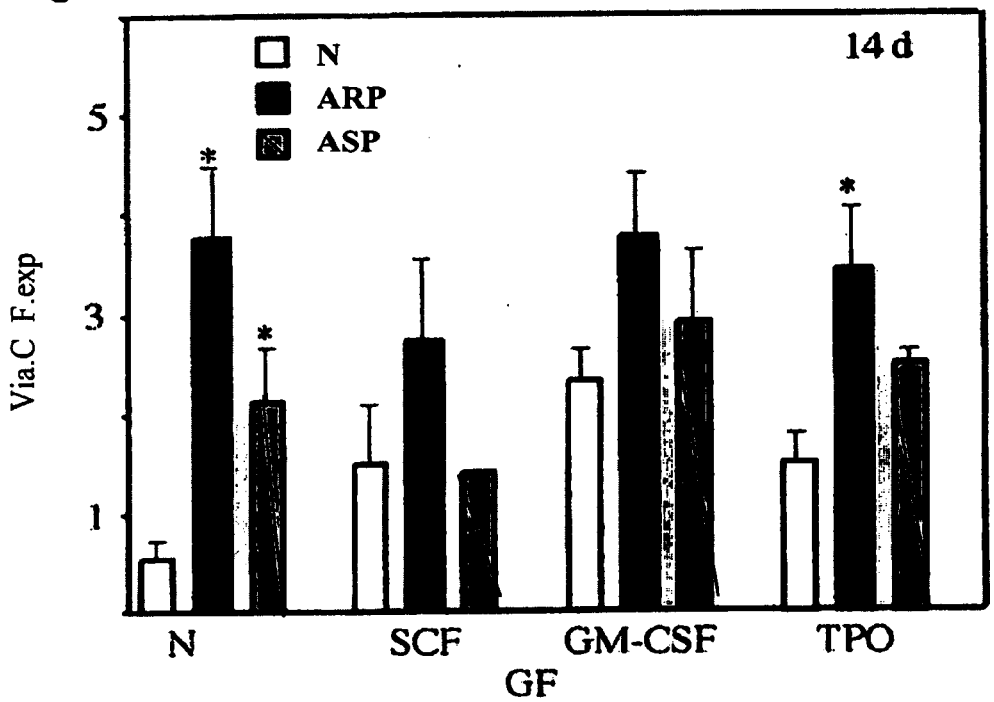

FIG. 4A–B: Structure of the Peptides ARP and ASP, and Their Effect on Survival of CD34$^+$ Cells.

FIG. 4A—shows the amino acid sequence and predicted secondary structure of the ARP and ASP peptides.

FIG. 4B—shows the effect of ARP (black bars) or ASP (gray bars) peptide, compared to controls (white bars) on survival of CD34$^+$ cells, in combination with the indicated growth factors (GF) or with no addition of growth factors—None (N), for 14 days (d). The results are represented as Viable cells (fold of expansion (Via.C. f.exp).

Figure 5:
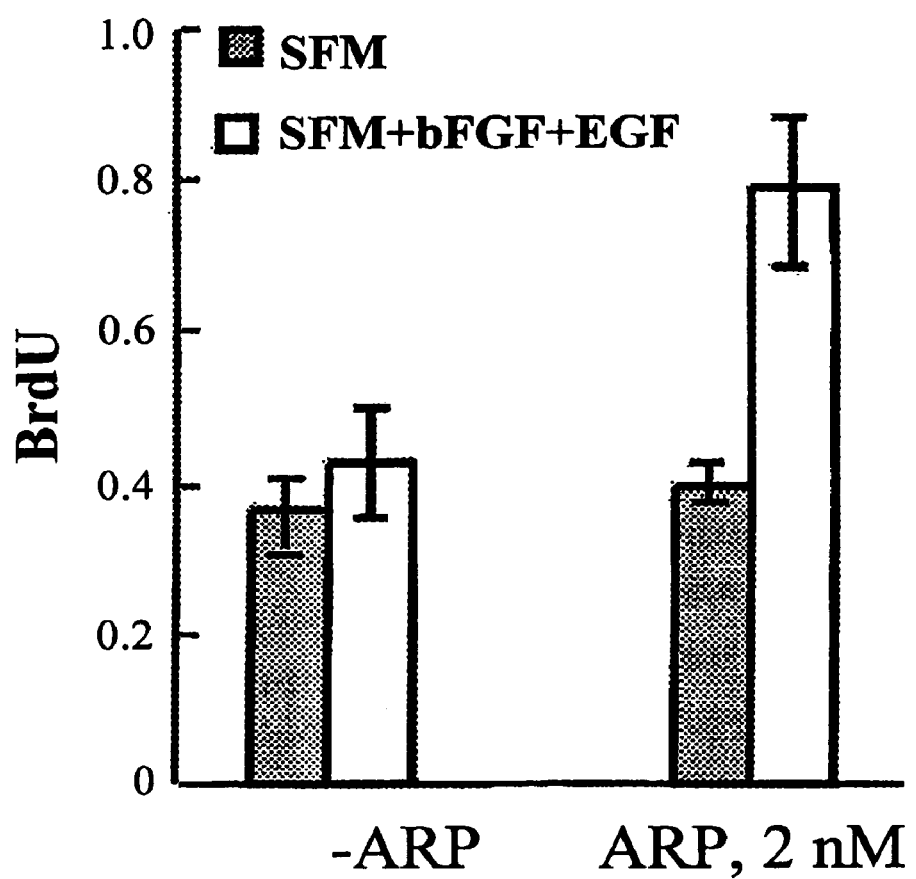

FIG. 5: Effect of ARP and Growth Factors on Transformed Bone Marrow Endothelial Cell Proliferation.

Transformed bone marrow endothelial cells were incubated in a serum free medium (SFM) with 2 nM of ARP, with or without endothelial growth factors (bFGF 20 ng/ml and EGF 10 ng/ml), for 48 hrs. Cell proliferation was determined by the level of BrdU incorporation measured by 5-Bromo-2'-deoxy-Uridine Labeling and Detection Kit III. Each column shows the average value of four wells +/− the standard error of the mean.

Figure 6:
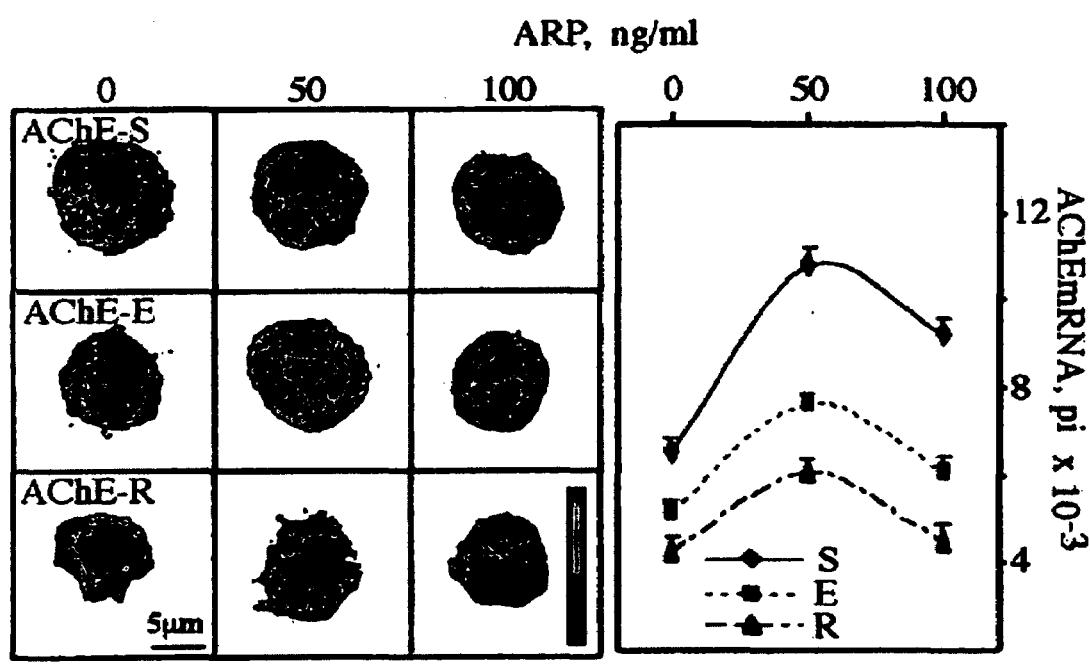

FIG. 6: ARP Operates as an Autologous Inducer of ACHE Gene Expression.

Left—In situ hybridization of representative CD34$^+$ cells treated with ARP.

Right—Average labeling densities of AChE mRNA splice variants (S, E, R) versus ARP concentration (top), as pixels (pi)x10$^3$.

Figure 7A:
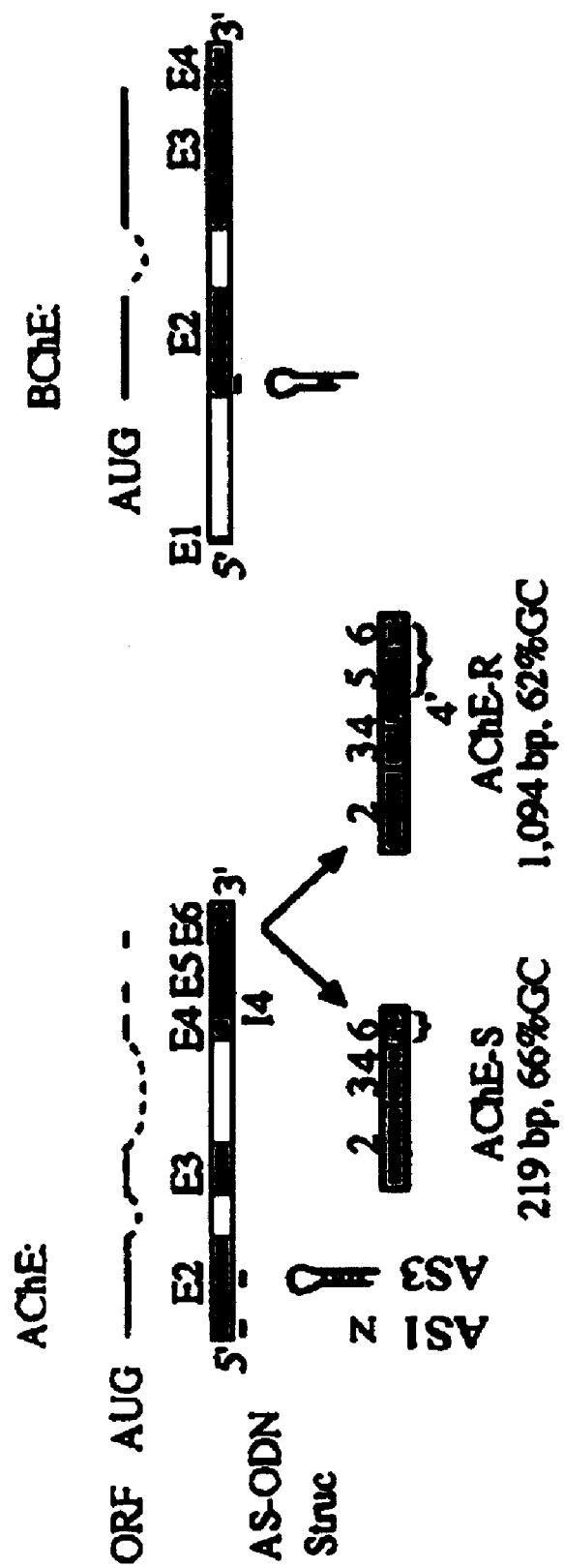
Figure 7B:
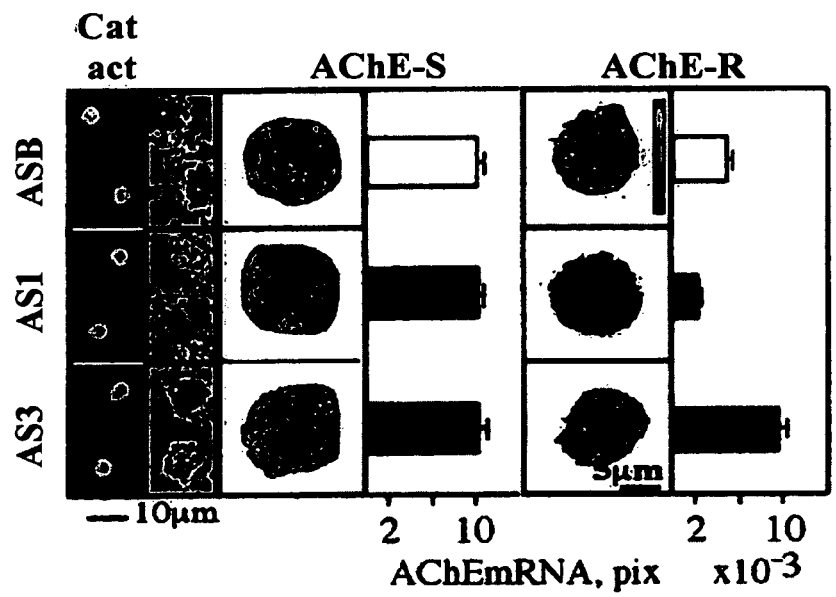
Figure 7C:
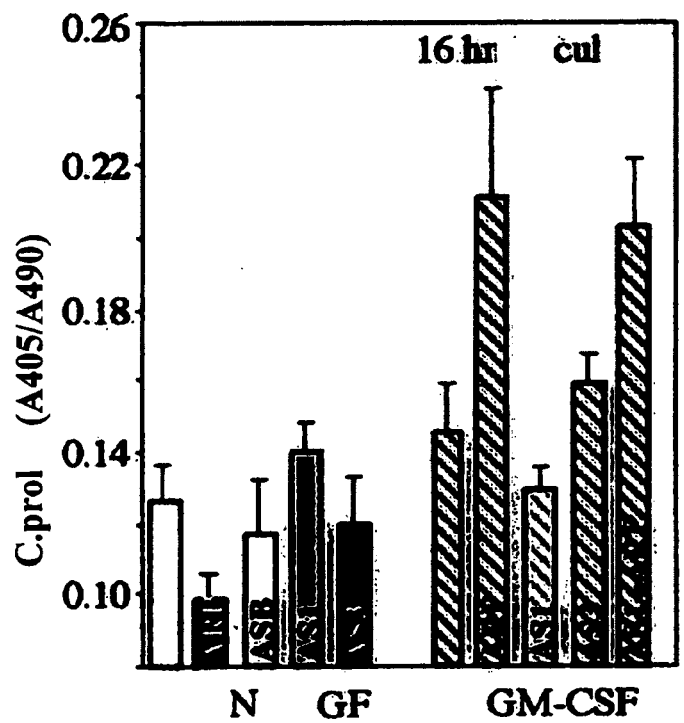

FIGS. 7A–C: ARP Induces Stem Cell Proliferation as Measured by BrdU Incorporation.

FIG. 7A—shows scheme of AChE and BuChE (BChE) genes and AChE splice variants.

FIG. 7B—shows selective susceptibility of AChE-R mRNA in CD34$^+$ stem cells to AS-ODN destruction as parameter of pixels (pi)x10$^3$.

FIG. 7C—shows stem cell proliferation in the presence of the indicated antisense ODNs with GM-CSF and ARP added as indicated for 16 hours (h) culture (cul), cell proliferation (c proli) is shown.

Figure 8A:
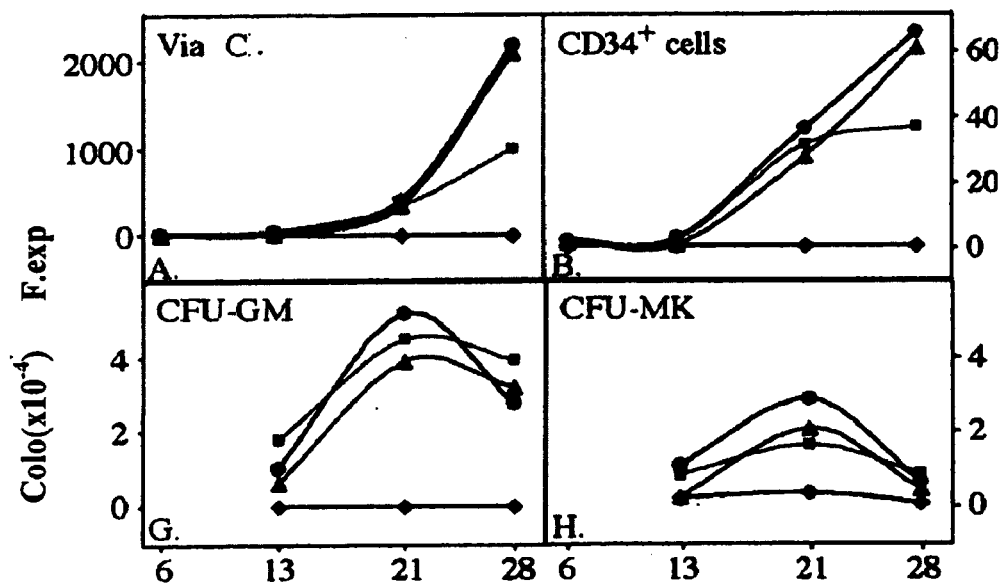
Figure 8B:
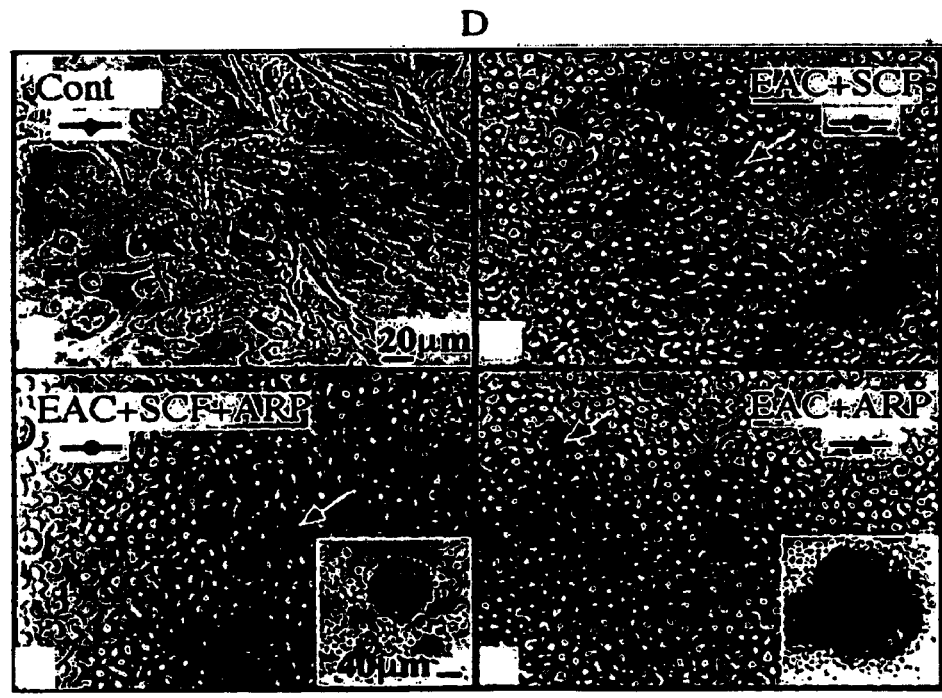

FIGS. 8A–B: Redundant Properties of ARP and SCF.

FIG. 8A—shows cell counts from long-term CD34$^+$ liquid cultures grown in the absence of growth factors (diamonds), in the presence of early-acting cytokines (EAC: IL3, IL6, TPO and FLT3) and SCF (squares), in the presence of EAC+ARP (triangles) or in the presence of EAC+ARP+ SCF (circles). Upper left, viable cell (Via c) count as a parameter of fold of expansion (F exp), Upper right, CD34$^+$ cell count, Lower left, colony (Colo) forming unit count for GM progenitors; Lower right, colony forming unit count for MK progenitors.

FIG. 8B—shows representative photographs of the 28-day (D) liquid cultures detailed in FIG. 8A. Upper left, control (Cont); Upper right, cultures treated with EAC and SCF; Lower left, cultures treated with EAC+SCF+ARP; Lower right, cultures treated with EAC+ARP.

Figure 9A:
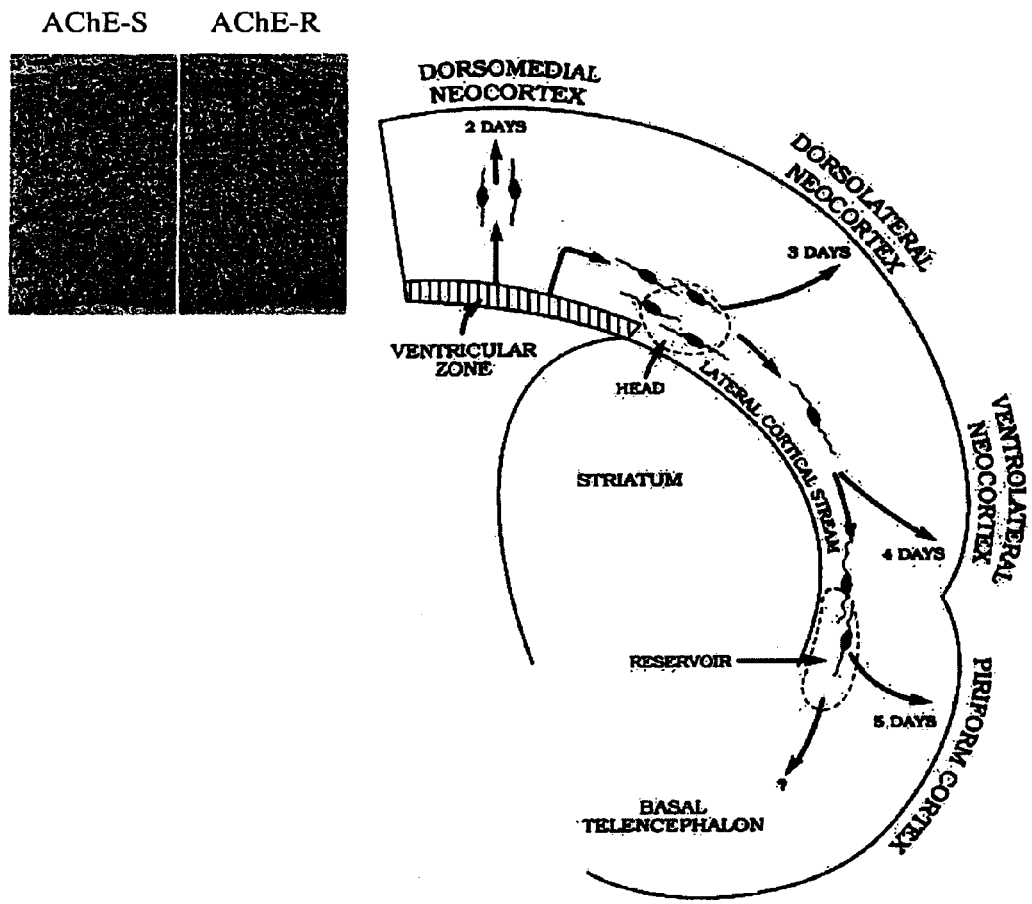
Figure 9B:
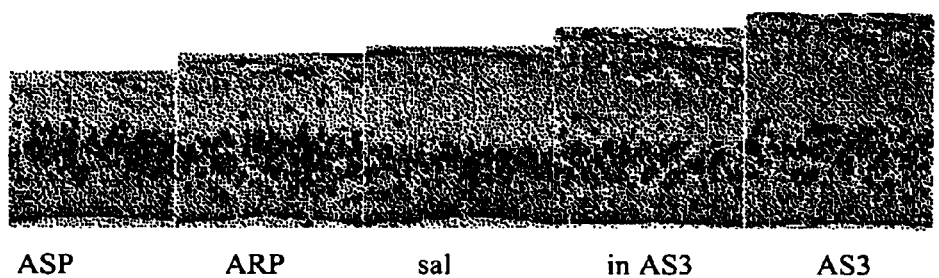

FIG. 9A–B: Migration of Neurons to the Perimeter of the Cortex in Embryonic Mouse Brain.

FIG. 9A—shows labeling with anti-ARP that labels distinct structures in embryonic cortex of mouse brain, or with anti-AChE that labels neurons.

FIG. 9B—shows BrdU labeling in developing brain in order to correlates the effects on mitotic activity with the treatment by the C-terminal peptides: ARP, ASP, saline (sal), and an anti-AChE oligodeoxynucleotide (ODN): inverse AS3 (in AS3) or AS3.

FIG. 10: Schematic Illustration of the Cortical Plate.

Figure 11A:
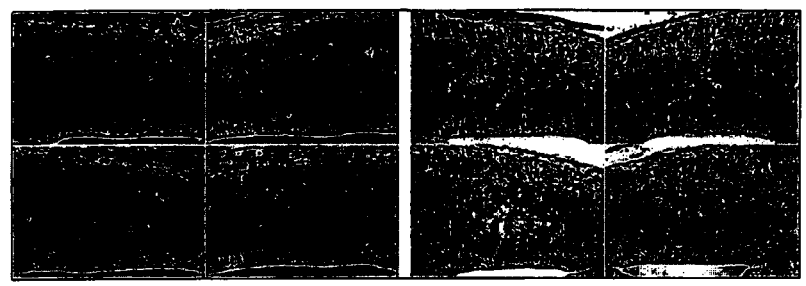
Figure 11B:
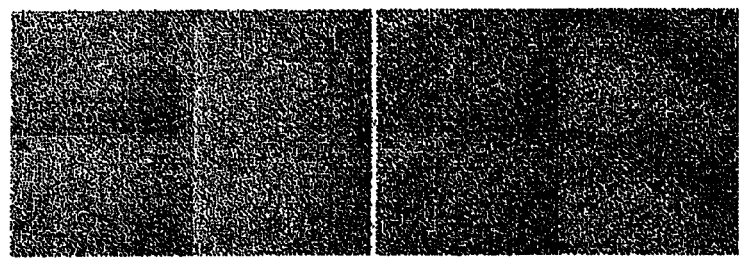

FIG. 11A–B: Suppression of ARP Levels by Antisense Treatment.

FIG. 11A—shows immunolabeling of ARP in treated brain.

FIG. 11B—shows in situ hybridization analysis in embryonic brain.

Figure 12A:
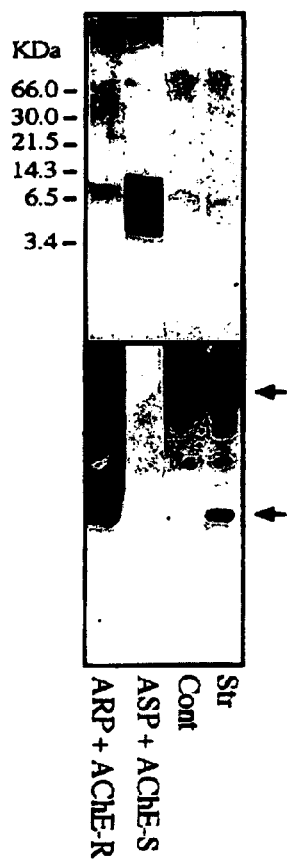
Figure 12B:
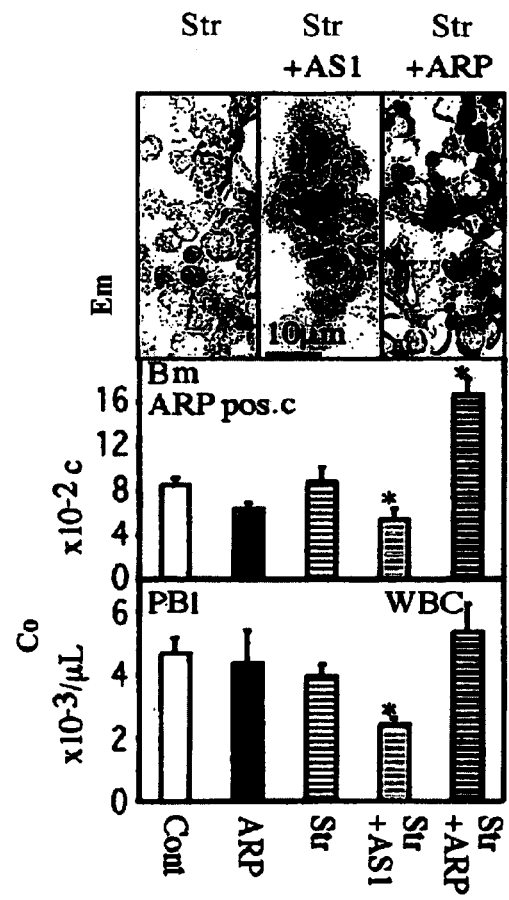
Figure 12C:
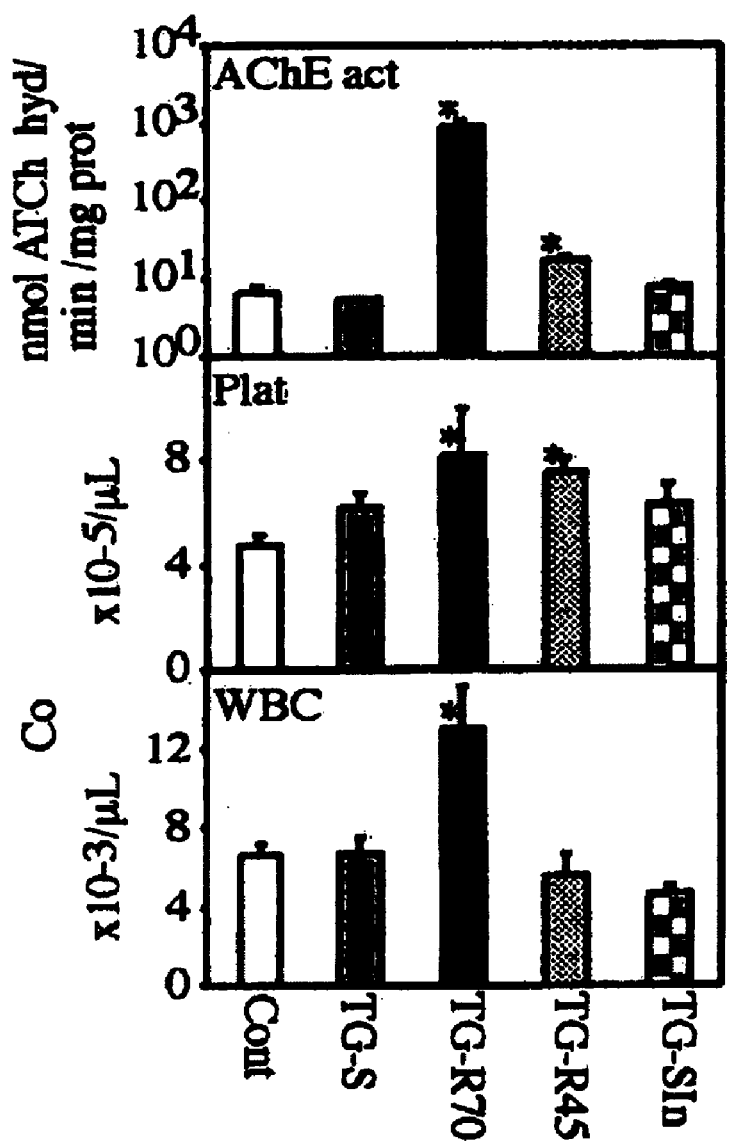

FIGS. 12A–C: ARP has Short- and Long-term Hematological Effects in vivo.

FIG. 12A—shows that ARP accumulates in the serum under stress. Top: Poinceau-stained polyacrylamide gels; Bottom: detection of ARP and AChE (arrows) in the immunoblot by anti-ARP antibodies in Stress (Str) or control (cont).

FIG. 12B—shows that ARP facilitates the stress (str)-induced hematopoietic responses in vivo by showing the number of labeled cells (C) per 100 cells counted (Co) at ×1000 magnification in 5 different fields. Bone-marrow (BM) labeling and white blood cell (WBC).

Asterisks in FIGS. 12A and B denote statistical significance (p$\leq$ 0.05, ANOVA).

FIG. 12C—shows that persistent AChE-R overproduction increases platelet (plt) and WBC counts (Cou) in a dose-dependent manner. The upper panel shows the AChE activity (act) as a function of nmol ATCh hydrolysis (hyd) per min and mg protein (prot).

Figure 13B:
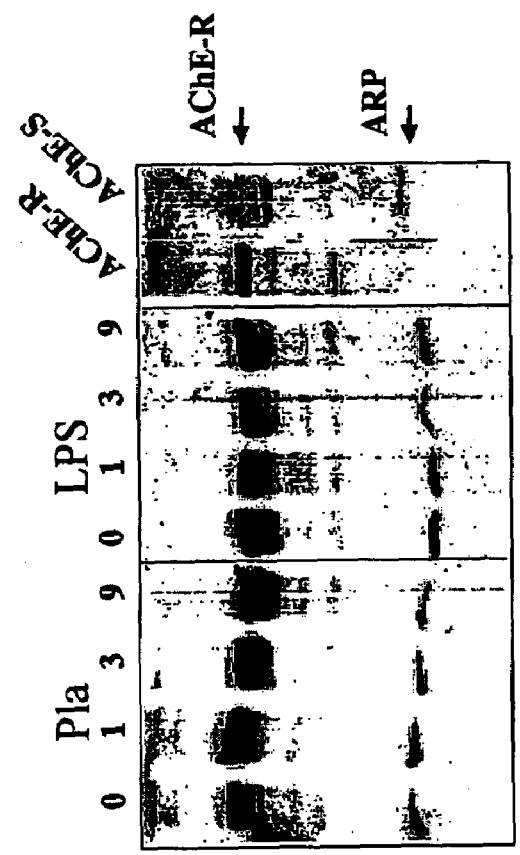
Figure 13A:
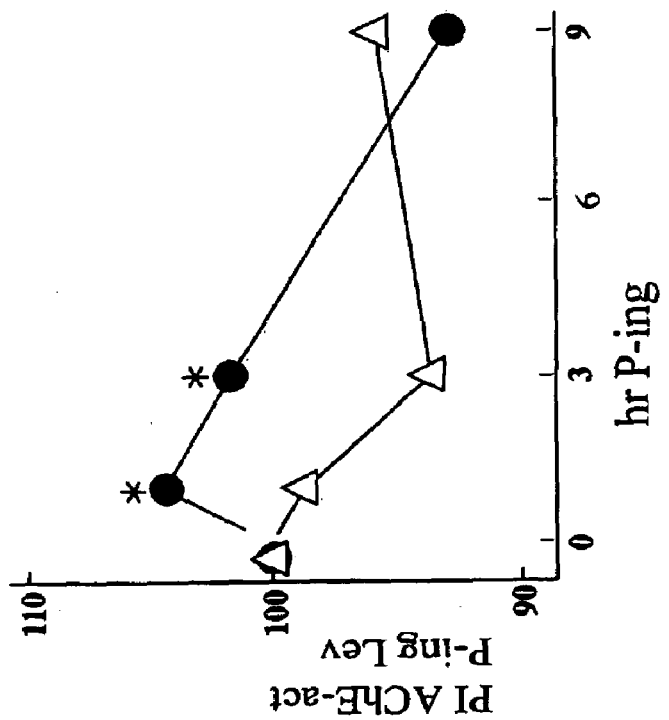
Figure 13C:
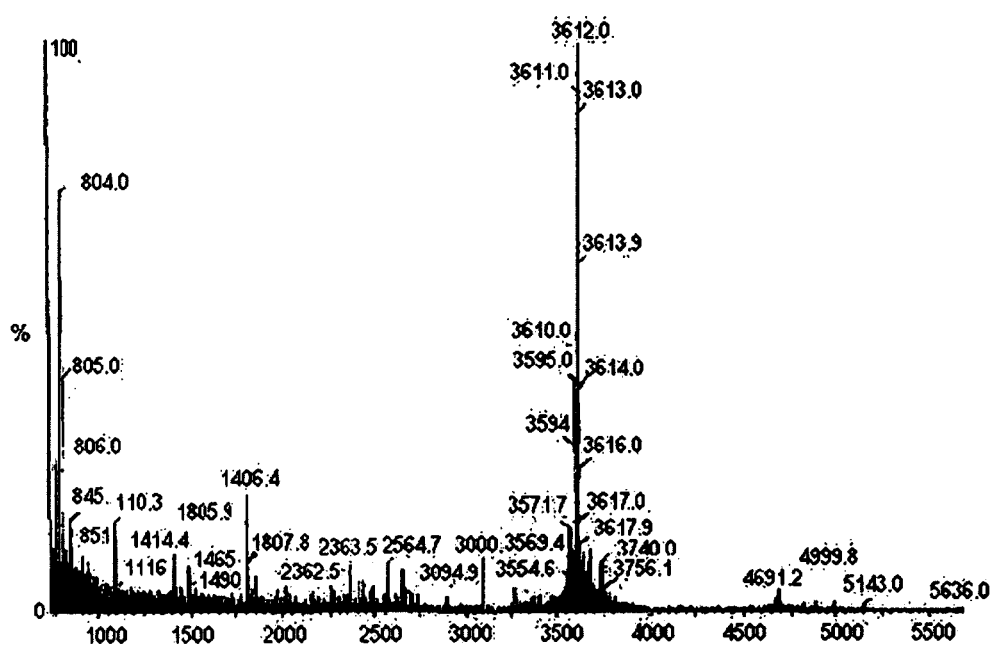

FIG. 13A–C: AChE and ARP in Human Blood Plasma.

FIG. 13A—shows plasma AChE activities (pl AChE act) under lipopolysaccharide exposure (8 ng/kg body weight). The level of AChE activity in all samples was determined in the presence of $10^{-5}$ M iso-OMPA and for each individual was compared to the placebo injection performed within 10 days as precents from the pre injection levels (p inj lev) (* denotes statistical significance).

FIG. 13B—shows immunodetection of ARP epitopes in human blood. Plasma prepared from the blood of one volunteer was electrophoresed by SDS-PAGE, and the gel immunoreacted with anti-ARP-GST antibodies. The right lanes indicate the response to a placebo (pla) injection; the next set, the response to injection of lipopolysaccharide (LPS) as a parameter of hours post injection (h po inj).

FIG. 13C—shows mass spectroscopy of gel-eluted band.

FIG. 14: Injected Synthetic ARP (0.1 mg/Kg) Induces Slow Onset of LTP Measured 24 Hr Post-injection.

Schaffer collaterals-CA1 synaptic pathway on hippocampal slices from a injected mice with ARP (i.p. 0.1 mg/Kg body weight) or with P-BAN as control, were tested after LTP induction. The changes in the slope (sl) of the post synaptic field potential was followed for 3 hrs (indicated by Time =T in minutes).

Figure 15A:
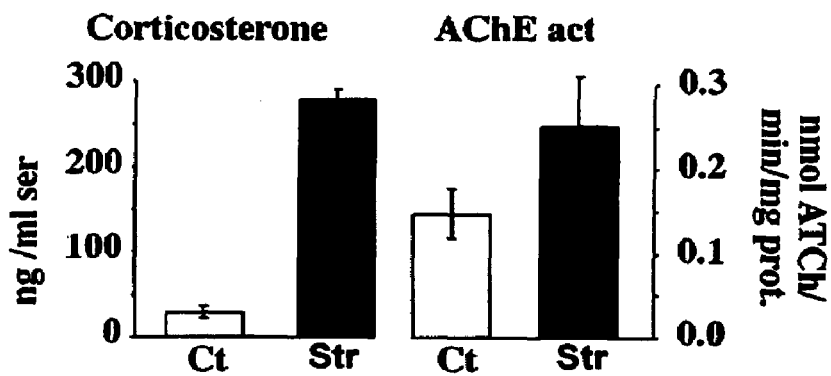
Figure 15B:
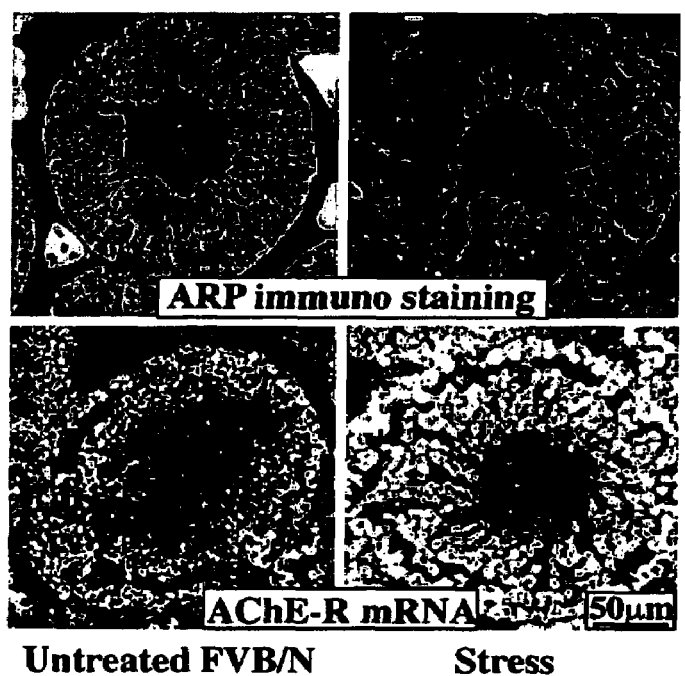

FIG. 15A–B: Repeated Confined Swim Stress Induces Testicular AChE-R Overexpression FIG. 15A—shows biochemical stress correlates. Shown are average values and standard evaluation of the mean for serum corticosterone concentrations and catalytic activities (act) of AChE in testicular homogenates from untreated control (ct) and stressed (str) mice as parameter of ng/ml serum (ser). Stars note statistically significant differences (Wilcoxon-Mann-Whitney, p<0.01).

FIG. 15B—shows elevated AChE-R production. Shown are sections of testicular tubules from untreated FVB/N mice or from FVB/N mice subjected to 4 consecutive daily treatments of confined swim stress. Labeling was with antibodies selective for ARP, the C-terminal peptide unique to AChE-R (top lane), or with an AChE-R cRNA probe detecting AChE-R mRNA transcript (lower lane).

Figure 16A:
Figure 16B:
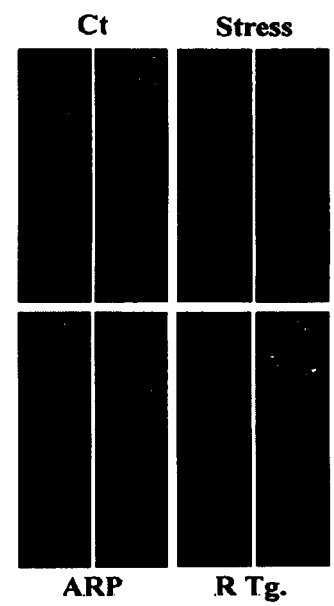

FIG. 16A–B: Differential Distribution of Sperm Labeling with Antibodies Targeted to AChE-R or AChE-S.

FIG. 16A—shows a scheme of mammalian sperm displaying its various components.

FIG. 16B—shows ARP staining in mature spermatids. Shown are compound confocal images of the most mature sperm cells in the central space within testicular tubules. Analyzed sections were labeled with antibodies targeted towards ARP. ARP labeling was performed in mice subjected to confined swim stress (str) or ARP injection as compared to untreated mice as control (Ct) or transgenic mice expressing the AChE-R transgene.

FIG. 17A–B: Suppressed ARP Labeling of Sperm Heads in Subjects with Unexplained Couple Infertility.

FIG. 17A—shows representative staining examples. Shown are compound confocal images of anti ARP-stained sperm cells from healthy donors (cont) or from male partners from couples with unexplained infertility (Cou infl).

FIG. 17B—shows cumulative fractions of sperm cells with various stained domain. Shown are average ±SEM values of 3 analyzed populations from healthy donors (con) (top) or infertile couples (Cou inf) (bottom) in sperm head (H), head+midpiece (HM), midpiece (M), or unstained (none=N). Shown is the % of stained sperms (sp st). Note example magnified cells in corresponding columns.

Figure 18A:
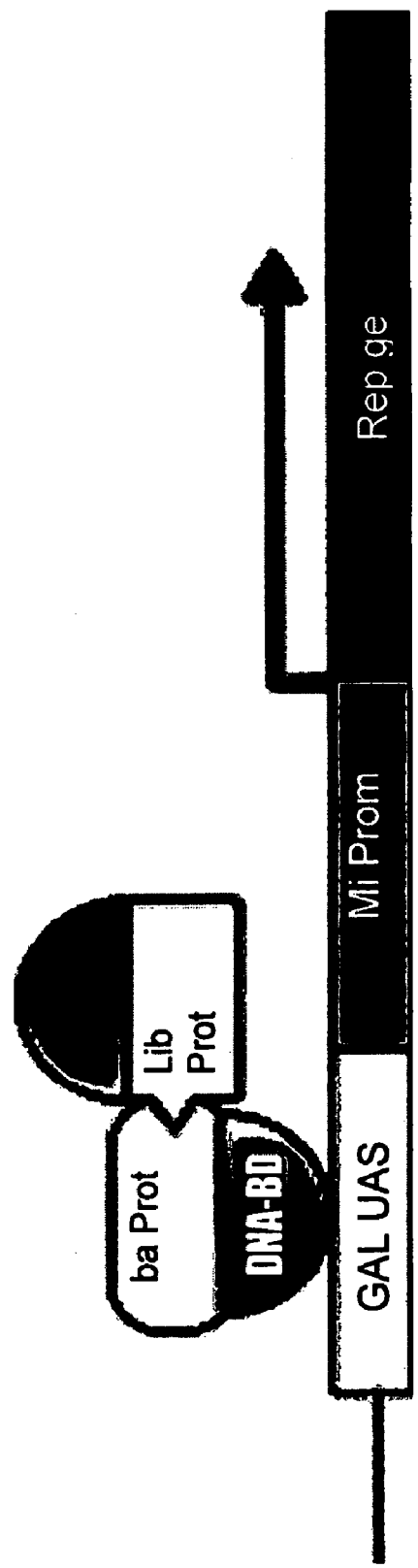
Figure 18B:
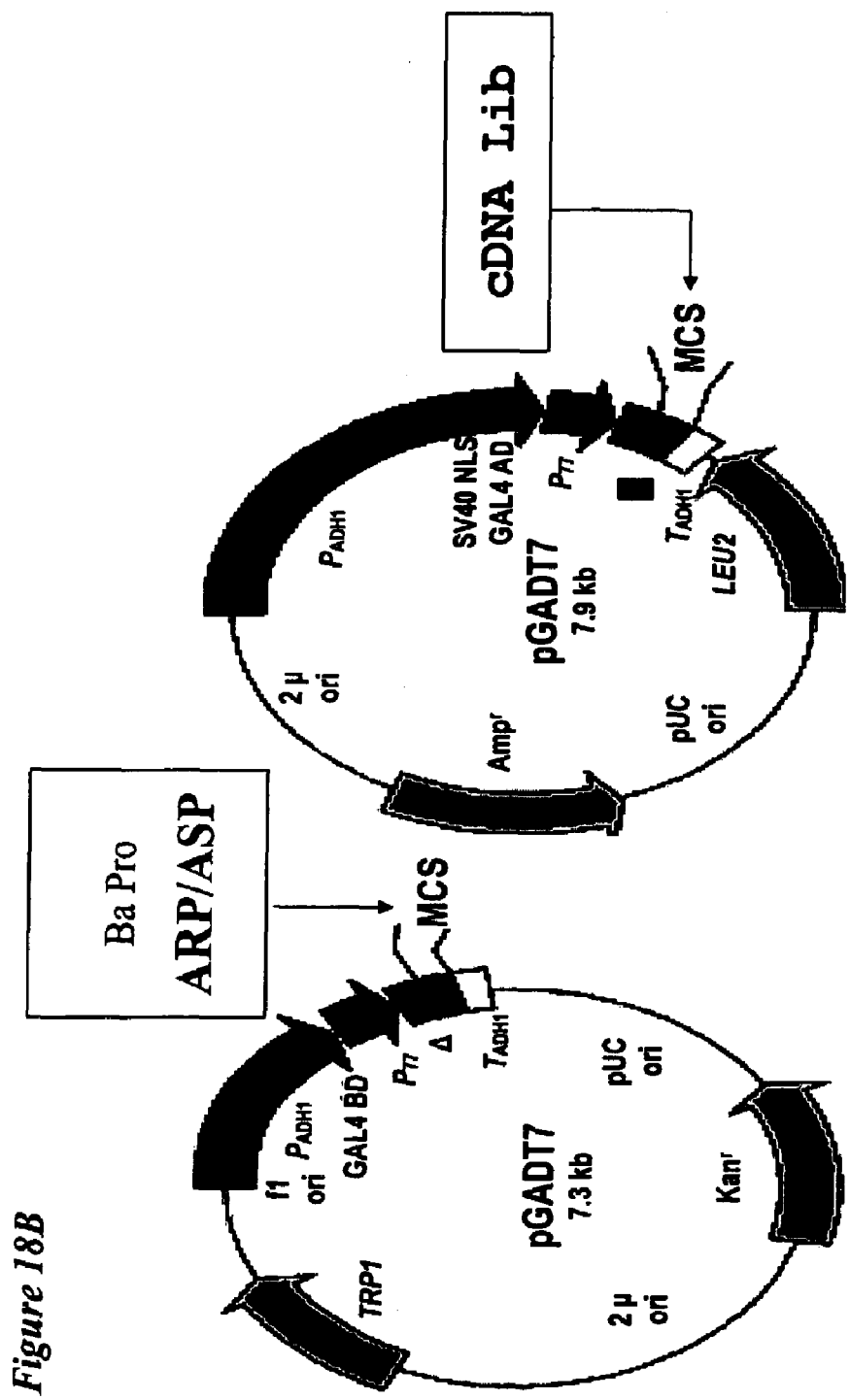

FIG. 18A–B: The Two Hybrid System Vectors.

FIG. 18A: Shows schematic model of the yeast two-hybrid system.

FIG. 18B: Shows a scheme of the pGBKT7 that was used to generate a fusion protein of the GAL4 DNA-BD and the bait protein, ARP or ASP. pGADT7 is used to express the cDNA library as a fusion to the GAL4 DNA-AD.

FIG. 19: Amino Acid Homology between RACK1 and the Sequence Established from the Rat Neonatal Aorta ARP.

Amino acid homology between RACK1 and the sequence established from the rat neonatal aorta ARP-two-hybrid positive clone (boxed), the synthetic peptides which inhibit PKC binding to RACK1 and are therefore homologous, at least in part, to the binding site of PKC to RACK1.

FIG. 20: Overlay Assay for AChE-R-RACK1 Interaction.

RACK1 was purified from E. coli as a fusion with maltose binding protein (MBP), released from the fusion protein by proteolytic cleavage with factor Xa. Both cleaved and uncleaved preparations were used for the overlay assay (ove). RACK1 samples were electrophoresed on a 4–10% denaturing polyacrylamide gel, blotted on an NC membrane, which was then stained with Ponceau, and striped. Thus, membrane protein blots were subjected to various labeling experiments:

FIG. 20A—Ponceau S staining of purified RACK1 fused to bacterial maltose binding protein (MBP-RACK1,–) or the 36 kDa RACK1 protein released by factor Xa proteolysis (+). Maltose binding protein (MBP) served as an internal control.

FIG. 20B—Horseradish peroxidase (HRP) immunolabeled RACK1 and its MBP complex and degradation products. Anti-RACK1 labeling either in fusion with MBP or alone, but not with MBP itself, demonstrated binding specificity.

FIG. 20C—RACK1-AChE-R complexes labeled by overlay with a PC12 cell homogenate overproducing recombinant AChE-R, followed by development with antibody to AChE N-terminus.

FIG. 20D—AChE N-terminus antibody showed no signal in membranes that were not overlaid previously with AChE-R overproducing cell homogenate (negative control).

Abbreviations: Prot.=protease; Ovl.=overlay; Detec. Ab.=detection antibody; Ponc.=Ponceau; Hom.=homogenates; N-ter.=N-terminus; n.=none.

Figure 21:
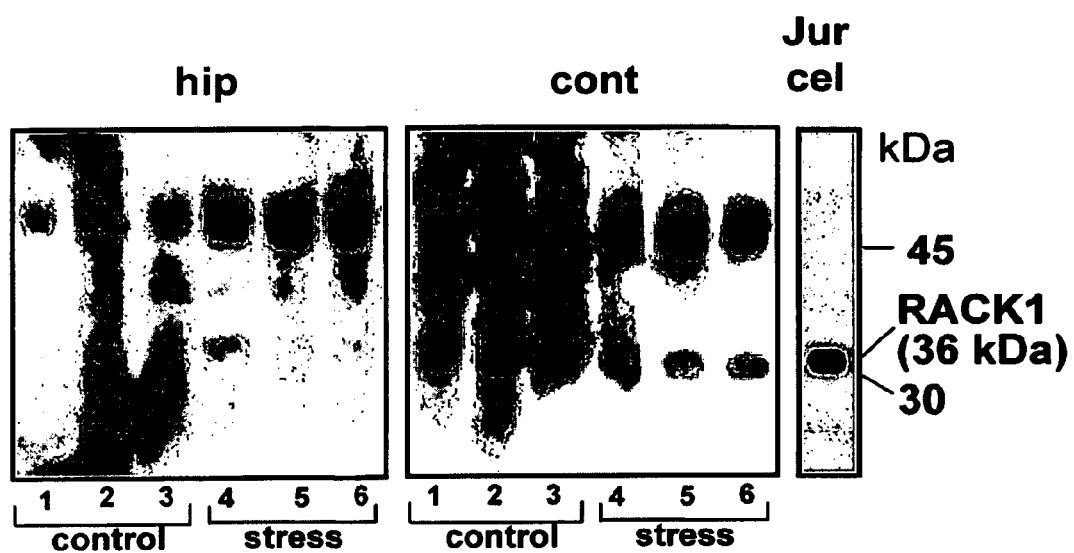

FIG. 21: Accumulation of a RACK1-Immunoreactivce Protein in the Mouse Post-Stress Brain.

Homogenates from mouse hippocampus (hip) and cortex (crt) [composed of 3 stressed (str), 4–6 and 3 control (cont), 1–3 mice] were separated on a denaturing gel and analyzed by immunoblot with anti-RACK1 antibody. Jurkat cells (Jc) homogenate was separated as well.

Figure 22:
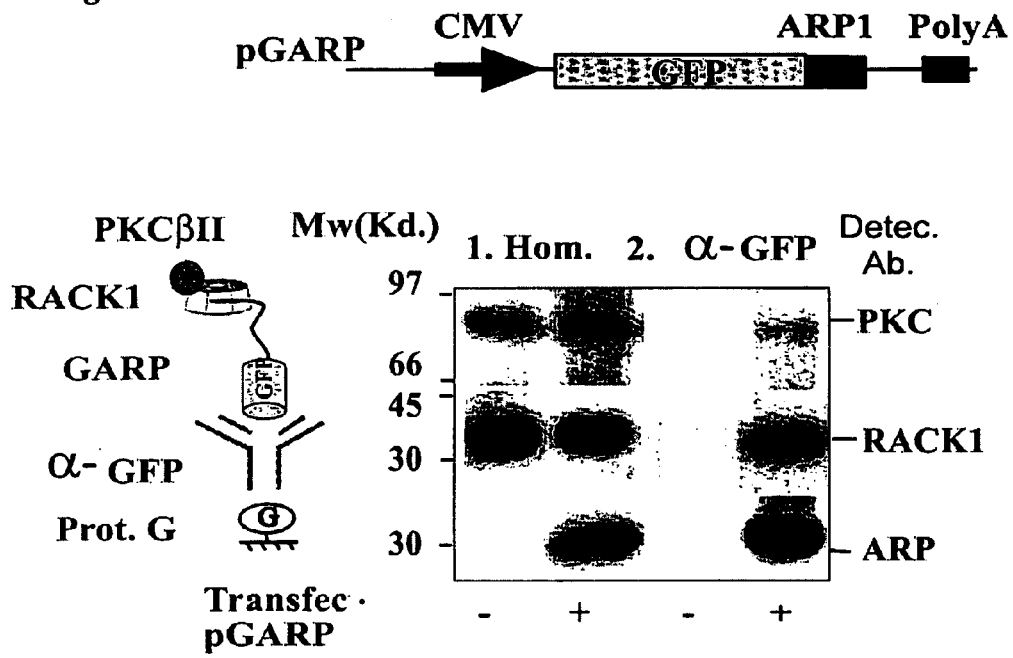

FIG. 22: ARP1 Promotes AChE-R/RACK1/PKCβII Triple Complex Formation in Transfected COS Cells.

Top: CMV-based vector encoding pGARP, a GFP fusion protein with ARP1.

Bottom: The drawing on the side represents the experimental concept.

1. Homogenates: Shown are immunolabeled RACK1 and PKCβII (but not ARP1) in non-transfected COS cell homogenates (–). In the presence of transfected GARP (+), COS cells show a band in the position correspondent to ARP.
2. Anti-GFP: Immunoprecipitation with anti-GFP antibodies precipitates PKCβII, ARP and RACK1 in pGARP transfected but not in non-transfected COS cells.

Abbreviations: Transfec.=transfection; Detec. Ab.=detection antibody

Figure 23:
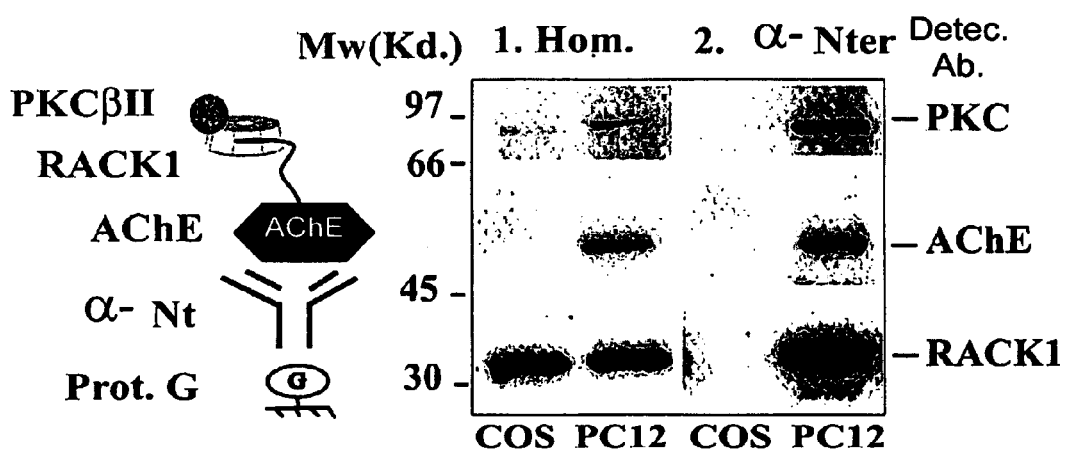

FIG. 23: Immunoprecipitation of AChE-R/RACK1/PKCβII Complexes.

RACK1 and PKCβII co-immunoprecipitate with anti-AChE antibodies. The schematic on the left represents the experimental concept.

1. Homogenates; PKCβII and RACK1 are immunodetected in homogenates of COS cells, which do not express AChE, and PKCβII, RACK1 and AChE are detected in PC12 cell homogenates.
2. Anti-AChE N-terminus: Dissolved immunoprecipitation complexes created with antibodies to the N-terminus of AChE display no signals in COS cells, but are positive for all three partner proteins in PC12 cells, demonstrating AChE requirement for the creation of these complexes.

Abbreviations: Detec. Ab.=detection antibody; Hom.=homogenates; Nter.=N-terminus; Prot.G=protein G.

FIG. 24A–J; RACK1 and AChE-R Co-overexpression in Parietal Cortex and CA1 Neurons Under Stress.

Shown are parietal cortex sections stained with cresyl violet or with anti-RACK1 or anti-AChE-R antibodies, in lower and higher magnifications. Note uneven labeling patterns of both proteins in the cytoplasm and proximal processes of individual pyramidal neurons in the parietal cortex and hippocampus CA1 (insets). Note RACK1 and AChE-R expression increases in layers 5 (arrows) of the parietal cortex under stress.

Figure 24A:
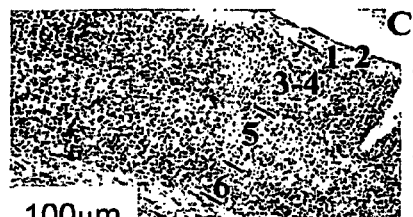
Figure 24B:
Figure 24C:
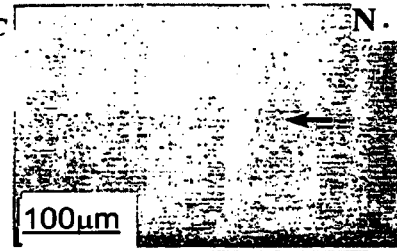
Figure 24D:
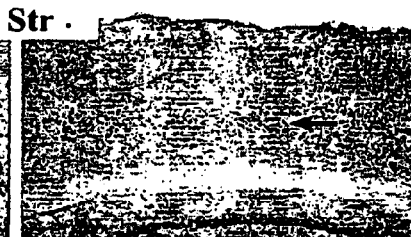
Figure 24E:
Figure 24F:
Figure 24G:
Figure 24H:
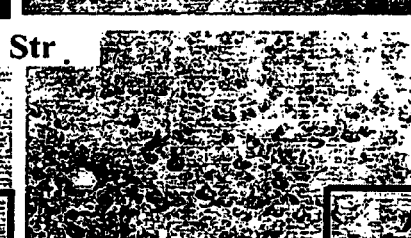
Figure 24I:
Figure 24J:
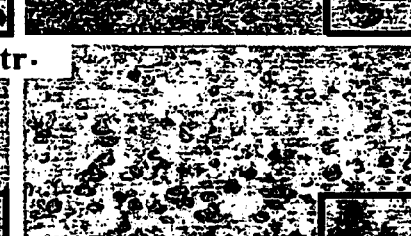

FIG. 24A: Cresyl violet staining, lower magnification.
FIG. 24B: Cresyl violet staining, higher magnification.
FIG. 24C: No stress, anti-RACK1 staining, lower magnification.
FIG. 24D: No stress, anti AChE-R staining, lower magnification.
FIG. 24E: Stress, anti-RACK1 staining, lower magnification.
FIG. 24F: Stress, anti-AChE-R staining, lower magnification.
FIG. 24C: No stress, anti-RACK1 staining, lower magnification.
FIG. 24D: No stress, anti AChE-R staining, lower magnification.
FIG. 24E: Stress, anti-RACK1 staining, lower magnification.
FIG. 24F: Stress, anti-AChE-R staining, lower magnification.
FIG. 24G: No stress, anti-RACK1 staining, higher magnification.
FIG. 24H: No stress, anti AChE-R staining, higher magnification.
FIG. 24I: Stress, anti-RACK1 staining, higher magnification.
FIG. 24J: Stress, anti-AChE-R staining, higher magnification.

Abbreviations: CV=cresyl violet; N. Str.=no stress; Str.=stress.

FIG. 25: Transgenic AChE-R Overexpression Intensifies Neuronal RACK1 and PKCβII Labeling in Hippocampal CA1 Neurons.

FIG. 25A—Immunoblot analysis. The immunoblot shows the bands corresponding to PKCβII, AChE-R and RACK1 following gel electrophoresis of clear hippocampal homogenates from two FVB/N controls and two sex and age-matched AChE-R transgenic mice (Tg). Note the intensified staining in transgenics and the fast migrating additional PKCβII band, which could not be detected in controls. Representative results from five reproducible experiments.

FIG. 25B–D—Partial overlaps in neuronal ACHE-R accumulation and PKCβII distributions. Shown are selected brain sections (posterior to Bregma 0.0–0.2 mm, 1.5–1.7 mm and 2.9–3.1 mm respectively) and the corresponding subregions where AChE-R accumulation (triangles) or PKCβII co-labeling in AChE-R accumulating neurons (circles) were detected. Staining intensity was low (+), medium (++) or high (+++). The corresponding subregions are numbered as follows: 1, Cortex upper layers; 2, Cortex lower layers; 3, striatum; 4, lateral septum; 5, piriform cortex; 6, hippocampus CA1; 7, hippocampus CA3; 8, hippocampus dentate gyrus; 9, basolateral amygdala; 10, central amygdala; 11, lateral hypothalamus; 12, ventromedial hypothalamus; 13, ventral lateral thalamus; 14, Edinger-Westphal nucleus; 15, Red nucleus; 16, Pre-tectal area.

FIG. 25E: Hippocampal immuohistochemistry. Shown are parallel CA1 regions from representative control and AChE-R transgenics stained with antibodies toward PKCβII, AChE-R or RACK1, as indicated. Note the intensified non-homogeneous staining of hippocampal neurons in the brain of transgenics for both AChE-R and RACK1, the relatively high background staining of PKCβII and the microglia (arrows) positive for AChE-R.

Abbreviations; Cont.=control; Tg.=transgenic.

Figure 26A:
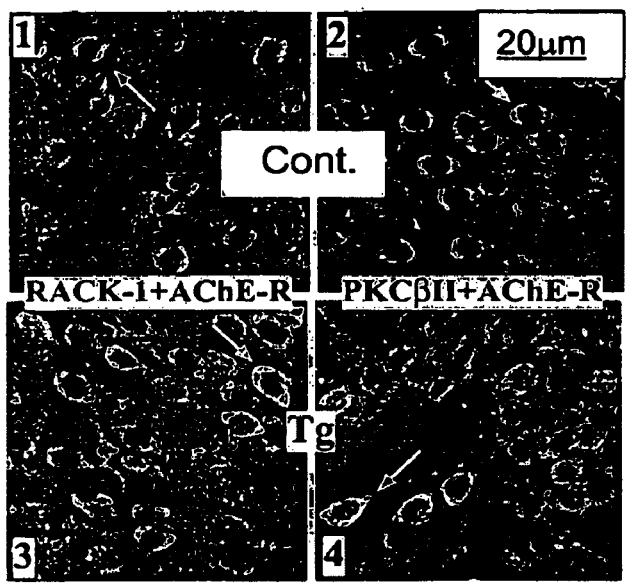
Figure 26B:
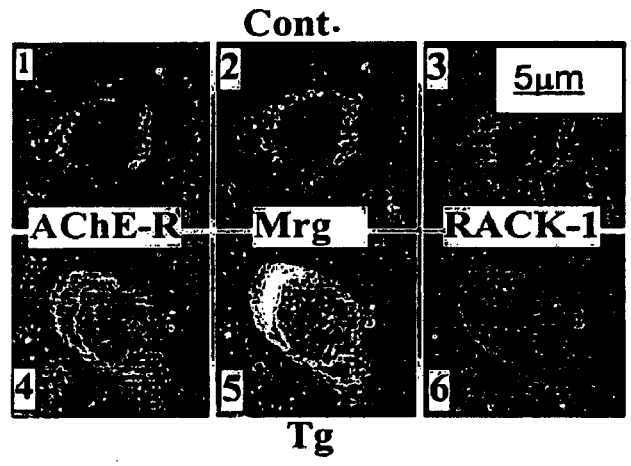
Figure 26C:
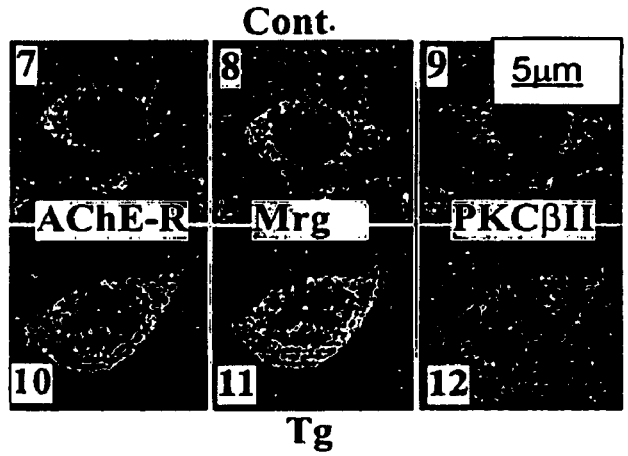

FIG. 26A–C: Double-Labeling Highlights the AChE-R Modulation of AChE-R/RACK1/PKCβII Complexes.

FIG. 26A—PKC activity is increased in ACHE-R transgenics PKC activity in brain homogenates from AChE-R transgenic was measured using the PKC assay kit (Upstate Biotechnology). Note the elevation of PKC activity in the different brain regions in the AChE-R transgenics as compared to FVB/N controls.

FIG. 26B–C—Shown are merged confocal micrographs from individual upper layer parietal cortex neurons of FVB/N and AChE-R overexpressing transgenic mice, co-immunolabeled with AChE-R/RACK1 or AChE-R/PKCβII. Staining was with antibodies to AChE-R (green) and RACK1 or PKCβII (red); merged micrographs show yellow signals for overlap staining, with orange regions reflecting high partner levels. Note the uneven, distinct distributions of the analyzed antigens in cortical neurons, with AChE-R labeling demonstrating perikaryal distribution, RACK1 more mobilized toward the perikaryal region identified in top sections (No. B5) and PKCβII highlighted in dense clusters co-localized with both RACK1 and AChE-R (No. C11).

FIG. 26B—co-immunolabeling with AChE-R and RACK1.

FIG. 26C—co-immunolabeling with AChE-R and PKCβII.

Abbreviations: Cont.=control; Mrg.=merge; Tg.=transgenic.

EXAMPLES

Experimental Procedures

Cell Source: UCB was collected, following informed consent of the parents and with the approval of the Sourasky Medical Center Ethics Committee, as previously described [Grisaru et al. (1999a) *Am. J. Obstet. Gynecol*, 180, 1240–1243]. Following 1:1 (v/v) dilution in Iscove's modified Dulbecco medium (IMDM, Beit Haemek, Israel), mononuclear cells were separated using 3% gelatin (Difco, Detroit, Mich.) and Ficoll-Hypaque gradients (<1.077 g/ml; Pharmacia, Uppsala, Sweden) [Pick et al. (1998) *Br. J. Haematol*. 103, 639–50]. CD34$^+$ cells were enriched using CD34 immunoglobulin-coated magnetic beads (CD34 progenitor cell selection system, Dynal, Norway). CD34$^+$ cells analysis was performed by flow cytometry (Becton Dickinson Immunocytochemistry System Inc., San Jose, Calif.), using CD34-PE (Becton Dickinson Immunocytometry System, Inc.) and CD45-FITC (Dako, Glostrup, Denmark) monoclonal antibodies. May-Grünwald-Giemsa staining revealed stem cell morphology.

Liquid Cultures: UCB CD34$^+$ cells were set for liquid cultures at a concentration of $10^5$/mL in IMDM, containing 10% autologous plasma, 2 mM L-glutamine (Sigma Chemical Co., St Louis, Mo.), penicillin (100 mg/mL), streptomycin (100 mg/mL), amphotericin B ($2\times10^{-5}$ M) (Sigma Chemical Co.), and heparin (20 IU/mL, Gibco, Grand Island, N.Y.), all in a fully humidified atmosphere at 37° C. and 5% $CO_2$. The following elements were added where noted:
1. Hematopoietic growth factors: Interleukin 3 (IL3, 5 ng/mL, Immunex, Seattle, Wash.), interleukin 6 (IL6, 50 ng/mL, R&D Systems, Minneapolis, Minn.), TPO (1 ng/mL, R&D Systems), stem cell factor (SCF, 10 ng/mL, R&D Systems), FLT-3 ligand (FLT3, 50 ng/mL, R&D Systems), granulocyte-macrophage colony stimulating factor (GM-CSF, 50 ng/mL, Biogenesis Ltd, Bournemouth, UK) and combinations of the above, for 24 hr to 28 days (supplemented every 4 days).
2. Endothlial Growth factors: Epidermal growth factor (EGF 10 ng/ml, Sigma Chemical Co.), basic Fibroblast growth factor (bFGF 20 ng/ml, Sigma Chemical Co.) incubated in a serum free medium (SFM) for 48 hr.
3. Stress mimicking conditions: Hydrocortisone sodium succinate (Abic Ltd., Netanya, Israel) at concentrations equivalent to normal, intermediate and stress serum cortisol levels (0.1, 0.6 and 1.2 µM, respectively (De Vroede et al., Arch. Des. Child 78, 544–7, 1998), for 24 hr.
4. Antisense oligonucleotides: 3'-terminal 2'-O-Methylated 15- and 20-mer oligodeoxynucleotides in the antisense (AS) orientation, targeted against the common sequence domain in human AChEmRNA and BuChE mRNA, as control, were used for 24 hr, as detailed elsewhere [Grisaru et al. (1999b) *Mol. Cell. Biol.* 19, 788–95].
5. AChE C-terminal peptides: The following C-terminal peptides of the AChE synaptic (ASP, also denoted SEQ ID: No. 2) and readthrough (ARP, also denoted SEQ ID: No. 1) isoforms were synthesized using a 433A peptide synthesizer (PE Applied Biosystems, Inc., Norwalk, Conn.).

ASP: 1-DTLDEAERQWKAEFHRWSSYMVHWKN-QFDHYSKQDRCSDL-40, also denoted as SEQ ID: No. 2.

ARP: 1-GMQGPAGSGWEEGSGSPPGVTPLFSP-26, also denoted as SEQ ID: No. 1.

Length and integrity of the peptide preparations were ensured following purification by HPLC, using a D-6000 chromatography data station (Hitachi Instruments, Inc., San Jose, Calif.). The working concentrations were 50 and 100 ng/mL (supplemented every 4 days) for liquid cultures grown between 24 hr to 28 days.

Culture Analyses: Twenty-four hr liquid cultures served for cytochemical staining, in situ hybridization, and cell proliferation assay by 5-bromo-2'-deoxy-Uridine (BrdU) incorporation [Grisaru et al. (1999b) id ibid.]. Twenty-eight day liquid cultures were sampled every 6–8 days for viable cell counting (using trypan blue dye exclusion), cell phenotyping (CD34$^+$, CD33$^+$ and CD41$^+$ quantification using flow cytometry, with CD34-PE, CD33-FITC (Immunotech/Coulter, Hialeah, Fla.), CD41-FITC (Immunoquality Products, Groningen, Netherlands) and CD45-FITC monoclonal antibodies), and growth of progenitor colony (granulocyte-macrophage and megakaryocytic), using previously described techniques (Pick et al. (1998) id ibid.).

Cytochemical Staining: Staining of AChE activity was essentially as detailed elsewhere [Grisaru et al. (1999b) id ibid], on non-fixed liquid cultures following 300×g centrifugation on collagen-coated cover slips placed on the bottom of the culture well, in the presence of $10^{-5}$ M iso-OMPA (ISO) or BW284C51 (BW), selective inhibitors of BuChE and AChE, respectively [see also Keymer et al.(1999) *Eur. J. Neurosci.* 11, 1049–57]. Nuclear staining w with 4',6-diamidino-2- phenylindole [DAPI, see e.g., Peterson et al. (1999) *Genetics* 152, 427–439].

Animals and Tissue Collection: Male FVB/N mice (2–6 months old) were sacrificed 24 hr following 4 successive days of a forced swim session as detailed [Kaufer et al. (1998) id ibid.], or a single injection of ARP (34 nmol/kg weight), or phosphate buffer (PB) for control. ARP, a 26 amino acid residue peptide synthesized according to the C-terminal sequence of human AChE-R [Grisaru et al. (1999b) id ibid.] was HPLC purified and mass-spectrometry analysed for purity. Control naïve mice and hAChE-R transgenics were sacrificed with no prior treatment.

Blood samples were allowed to clot 1 hr at room temperature and overnight at 4° C., followed by centrifugation and serum collection.

Testes and seminal vesicles were excised and weighed, fixed in 4% paraformaldehyde or Bouin's fixative for histological staining or kept at −70° C. for protein extraction.

Sperm cells were collected from one cauda epididymis shredded in 1 ml saline.

Evaluation of Serum Corticosterone Levels: concentrations were determined by radioimmunoassay.

Epididymal sperm motility was assessed by visually determining percent motile sperm. Sperm concentration was measured using the Makler chamber (company, city, state).

In Situ Hybridization: In situ hybridization procedures, were performed on cultured cells and human fetal tissues, as detailed elsewhere [Grisaru et al. (1999b) id ibid; Kaufer et al. (1998) id ibid.]. Cultured cells were centrifuged at 300× g and fixed, using 4% paraformaldehyde, to collagen-coated cover slips placed on the bottom of the culture well. Tissues from fetal hematopoietic organs (AGM, liver, spleen and bone marrow) were obtained in each of the selected gestational stages, from 2–3 normal aborted human fetuses. The project was approved by the Sourasky Medical Center Ethics Committee, and written informed consent was obtained from the parents. 5'-Biotinylated, 2'-O-methylated AChEcRNA probes complementary to 3'-alternative human ACHE exons were employed. Detection and quantification of the various AChEmRNA transcripts in fetal tissues were performed as previously described [Grisaru et al. (1999b) id ibid.]. Confocal microscopy scans of the culture-derived cells were obtained using a MRC-1024 Bio-Rad confocal microscope (Hemel Hempsted Herts., UK). A projection was built from each cell image and specific criteria were set for size and intensity of the Fagt Red fluorescence. Image-Pro 3.0 software (Media Cybernetics, Silver Spring, Md., USA) was used to analyze the signals obtained. ANOVA (Analysis of Variance) test was used for calculation of p values.

Human Sperm Smears: Air dried sperm smears of ejaculates collected from male donors or infertility patients were stained with the anti-ARP antibody as mentioned above.

Confocal Microscopy: An MRC-1024 Bio-Rad confocal microscope equipped with an inverted microscope and a 63×/2.4 oil immersion objective was used to scan the fast red precipitate used for ARP and ASP immunodetection. Fast red was excited at 488 nm, emission was measured using a 580df32 filter. Sections were scanned every 0.35 µm, and a three-dimensional projection was created from all sections.

For imaging of AChE-R, RACK1 and PKC, brain slices were scanned using a Bio-Rad MRC-1024 scanhead (Hemel Hempsted Herts., UK) coupled to an inverted Zeiss Axiovert 135M microscope with a 40× oil immersion objective (N.A. 1.3). Excitation wavelength was 488 nm (using 10% of a 100 mW laser power). Fluorescence emission was measured using a 580df32 bandpass interference filter (580 nm ±16 nm) for detecting tetra-methyl-rhodamine and a 525/40 filter for detecting fluorescein. The confocal iris was set to 3 mm. Conditions of scanning took into consideration the overlap of fluorescein fluorescence into the rhodamine filter (as were determined by control experiments). Images were then further processed using Image pro Plus 4.01 program (version 4.0, Media Cybernetics, Silver Spring, Md.).

DNA Sequence Analysis: The reverse sequence of the 7q22 cosmid (accession no. AF002993) containing the human ACHE gene and its upstream sequences, was searched for consensus motifs for binding transcription factors which regulate hematopoietic expression, using the MatInspector program with core similarity of 1, or the Findpatterns program of the University of Wisconsin GCG software package (Quandt et al., Nucleic Acids Res. 23, 4878–84, 1995).

Immunoblot: Mouse serum was diluted 1:10. ARP, ASP, recombinant AChE-S (Sigma Chemical Co.) and recombinant AChE-R extracted from transfected COS cells served as positive controls. Protein electrophoresis in SDS gradient (4–20%) polyacrylamide gels (Bio-Rad Laboratories, Hercules, Calif.) was followed by immunodetection using the rabbit anti-GST-ARP antibodies, Peroxidase-conjugated anti-rabbit immunoglobulins and ECL™ detection (Amersham Pharmacia Biotech, UK).

Methods for Culturing Murine Hematopoietic Cells:

Cell Collection

Blood: 1 ml of murine blood is collected by cardiac puncture and immediately deposited into pediatric vacutainer tubes containing Na citrate. Blood counts are performed using the AcT diff Coulter counter (Coulter-Beckman).

Bone Marrow: The tibia and femurs are surgically removed, cleaned and both ends of the bone cut open. The bones are placed in small tissue culture plates containing 2–5 ml of medium composed of RPMI, antibiotics and 10% heat inactivated fetal calf serum (complete medium) supplemented with heparin (5 U/ml) to prevent clotting. The BM contents are flushed out into the medium using a 25 gauge needle. Cells are passed up and down through the syringe three times to guarantee a single cell suspension.

Spleen: The spleen is surgically removed and cleaned and placed in 5 ml of medium composed of complete RPMI with heparin (5 U/ml) as described above. Both ends of the spleen are cut open and the spleen cells are expressed from the organ capsule by squeezing down on the spleen with the back barrel of a 5 cc sterile syringe. A single cell suspension is prepared by passing the cells up and down three times through a 5 ml syringe.

Cryopreservation

The hematopoietic cells are washed by the addition of an additional 5 ml of medium composed of complete RPMI with heparin, counted by manual hemocytometry and pelleted at 1500 RPM for 10 minutes. The cell pellets are resuspended at a concentration of $5 \times 10^6$–$10^{-7}$ cells/ml in ice cold freezing medium containing 50% DMSO and 30% RPMI (as above). Cells are allowed to remain on ice for up to 5 minutes and subsequently placed at −20° C. for 30 minutes. Cells are then transferred to −80° C. for a period of up to 6 months; for longer storage, cells are transferred to −180° C.

Hematopoietic Progenitor Cultures

For all colony assays duplicate samples of $1$–$2 \times 10^5$ cells are placed into 1 ml of medium plus the appropriate supplements for each cell lineage in small round tissue culture dishes (2.5 cm). These small dishes are placed into a larger TC dish (10 cm) together with a third small dish containing sterile water to prevent evaporation in the cultures. Cells are cultured at 37° C. in a fully humidified atmosphere containing 5% $CO_2$.

BFU-E

Two hundred thousand ($2 \times 10^5$) cells are placed into 1 ml of Alpha medium containing antibiotics, 30% methyl cellulose, 10% FCS and 2 ng/ml recombinant murine (r-mu) erythropoietin, and both BFU-E and the smaller CFU-E are counted after 10 days.

CFU-GM and CFU-GEMM

One hundred thousand ($1 \times 10^5$) cells are placed into 1 ml of Alpha medium containing antibiotics, 3% agar, 10% FCS and 5 ng/ml or both r-mu IL-3 and r-mu GM-CSF. CFU-GM, CFU-GEMM and CFU-bl are counted after 12 days.

CFU-MK

Two hundred thousand ($2 \times 10^5$) cells are placed into 1 ml of Alpha medium containing antibiotics, 30% methyl cellulose, 10% FCS and 5 ng/ml. r-mu thrombopoietin and 10 ng/ml stem cell factor. CFU-MK and BFU-MK are counted by staining the cells for AChE after 12 days.

Animal Models and in vivo Experiments—Transgenic—

FVB/N mouse pedigrees expressing human AChE variants were described elsewhere, as were the biochemical methods for measuring AChE activity [Sternfeld et al. (1998b) *J. Physiol. Paris*, 92, 249–55]. The confined swim protocol for exerting acute psychological stress was performed as detailed [Kaufer et al.(1998) id ibid.]. Immediately following the stress, the treated mice were injected intraperitoneally with 100 ng ARP or 0.03 ng AS1, both per gram body weight. Another group of non-stressed mice were injected either with normal saline or ARP. Twenty-four hours later, the animals were sacrificed and peripheral blood was collected in EDTA covered tubes (Becton Dickinson Immunocytochemistry System, Inc., San Jose, Calif.) prepared with 25 units of heparin sodium USP (Kamada LTD, Kibbutz Beit-Kama, Israel). Whole blood AChE activity was analyzed, and WBC and platelet counts determined, using an Ac·T diff hematology analyzer (Beckman Coulter, Inc., Fullerton, Calif.).

Cytochemical and Immunohistochemical Staining

Staining of AChE activity was as detailed above. For immunohistochemistry, murine bone marrow smears were fixed with 4% paraformaldehyde (10 minutes, room temperature, RT); permeabilized with buffer containing 20 mM HEPES (pH 7.4), 300 mM sucrose, 50 mM NaCl, 3 mM $MgCl_2$ and 0.5% Triton X-100 (4 minutes on ice); washed twice with PBS (5 min each, RT); incubated in 1% $H_2O_2$ in methanol (15 min RT); and washed twice in PBS. Non-specific sites were blocked by incubating in 5% horse serum in PBS (20 min, RT). Labeling was in a humidified chamber with 1:50 dilution of affinity purified rabbit antiserum prepared against GST-fused recombinant ARP (1 hr, RT). Following 3 washes with PBS, smears were incubated with 1:100 biotinylated goat anti-rabbit Ig (Amersham Pharmacia Biotech UK Ltd., Buckinghamshire, UK) (30 min, RT). After 3 PBS washes, a mixture of biotin and avidin-peroxidase was added (30 min, ABC Elite Kit, Vector Labs, Burlingame, Calif.) and reacted with diaminobenzidine-hydrogen peroxide mixture (Sigma Chemical Co., St. Louis, Mo., 10 min), followed by counterstaining with Meyer's hematoxylin mixture (Sigma Chemical Co., St. Louis, Mo.), and immunomounting.

Immunohistochemistry and Nuclear Staining in Testis Sections

Detection of the AChE core protein and/or its variant C-terminal peptides was performed on 7 µm thick paraffin embedded testis sections with either anti-ASP (C-16; Santa Cruz Biotechnology, Santa Cruz, Calif.) or anti-ARP polyclonal antibodies [Sternfeld et al. (2000) id ibid.]. PCNA was detected using a dedicated staining kit (Zymed Laboratories, San-Francisco, Calif.); nuclear staining and counterstaining was with DAPI and hematoxylin, respectively (Sigma, St. Louis Mo.).

Expression of Recombinant ARP

The sequence, coding the C-terminal region of I4 (i.e., the "readthrough" variant of acetylcholinesterase, comprising the ARP peptide sequence), was amplified by PCR using the following oligonucleotide primers: GCT GGA TCC ATC GAG GGG CGA GGT ATG CAG GGG CCA GCG GGC (I4-up), also denoted as SEQ ID: No. 4, and TAT AAG CTT CTA GGG GGA GAA GAG AGG GGT (I4down), also denoted as SEQ ID: No. 5, and introduced into pGEX-KG (ATCC accession No. ATCC77103, see also Anal. Biochem. 192:262–267, 1991) plasmid.

Antibody Production

GST and I4-GST fusion protein were purified from the supernatant of *E. coli* lysate by affinity chromatography on glutathione-Sepharose (Pharmacia), eluted with 10 mM reduced glutathione in 50 mM Tris-HCl, pH 8.0, dialyzed to 0.1 M ammonium acetate buffer, pH 7.0, aliquoted and lyophilized. The stability and identity of the protein was confirmed by SDS-PAGE. The following protease inhibitors were used during the preparation: aprotinin (10 microgram/ml), benzamidine (5 mM), Pefabloc SC (0.2 mM), and EDTA (1 mM). Prior to affinity chromatography, the *E. coli* lysate was incubated for 20 min at 37° C. with 0.2 mM Mg-ATP in order to dissociate the fusion proteins from contamination of bacterial proteins. The procedure was performed according to Pharmacia recommendations.

Two New Zealand female rabbits were immunized subcutaneously with 0.3 mg fusion protein in complete Freund's adjuvant, and then reimmunized monthly with 0.2 mg fusion protein in incomplete Freund's adjuvant. Blood samples were taken 10 days after the immunization. The specific antibodies in the sera were detected by ELISA on immobilized fusion protein, in the presence of excess of soluble GST (20 microgram/ml). The reacting sera were chosen for antibody purification. The immobilized I4-GST, GST and *E. coli* lysate were prepared using Affigel 10 (Bio-Rad) according to the manufacturer's recommendations.

Crude IgG fraction was prepared from the serum by 50% saturation $(NH_4)_2SO_4$ precipitation and dialyzed in 100 mM Tris-HCl, pH 8.0. In order to get rid of anti-GST antibodies, the IgG fraction was incubated with GST beads (Affigel 10, Bio-Rad) overnight at 4° C. The bound material was eluted with 4.5 M $MgCl_2$. The procedure was repeated with the unbound material several times, until no antibodies were eluted from GST beads. In order to get rid of antibodies against possible contamination of bacterial proteins, the same procedure was performed with immobilized heat-shocked E. coli lysate proteins.

The unbound material was then applied to I4-GST beads (Affigel 10, Bio-Rad), incubated 2 hr at room temperature or overnight at 4° C., and the bound material was eluted with 3.5 M $MgCl_2$. The eluted antibodies were dialyzed against 10 mM Tris-HCl, pH 8.0, and then against PBS, containing 0.025% $NaN_3$.

Two-hybrid Screen

Vectors

A fragment of human AChE-R cDNA (nt 1796–1865 of hAChE, accession number M55040, followed by nt 1–111 from the genomic hAChE I4-E5 domain (Accession No. S71129, stop codon in position 86) was used as "bait" for the two-hybrid screen. Cloning into the EcoR1/SmaI sites of pGBK-T7 (Clontech, Palo Alto, Calif.), yielding the plasmid pGBK-ARP1. Cloning of the "bait" sequence into the Bsp120I/XbaI sites of pEGFP-C2 (Clontech) yielded the pGARP vector. The AChE-R expressing plasmid used for transfections has been described in detail [Seidman et al. (1995) Mol Cell Biol., 15, 2993–3002].

Screening

The "bait" EcoRI/HpaI fragment of AChE-R cDNA encodes the 51 amino acid long C-terminal fragment of AChE-R fused to the DNA-binding domain (BD) (amino acids 1–147) of the yeast GAL4 transcriptional activator. An amplified and CsCl gradient-purified human fetal brain cDNA library cloned into the AD vector [Chien et al. (1991) Proc. Natl. Acad. Sci USA 88, 9578–9582] encodes for a fusion protein with the yeast GAL4 activation domain AD, (amino acids 768–881). The AH109 yeast strain (Clontech) was sequentially transformed with the pGBK-ARP1 plasmid, and with 10–25 µg of the library DNA, using the Yeastmaker transformation system (Clontech). A total number of 240,000 independent clones were screened.

Preparation of Recombinant RACK1

A plasmid overexpressing MBP-RACK1 in E. coli pDEM31, a derivative of pMAL-c2 (New England Biolabs, Beverly, Mass.) [Rodriguez et al. (1999) id ibid.], was a kind gift from Dr. Daria Mochly-Rosen, Stanford. The pDEM31 vector expresses in E. coli recombinant RACK1 fused to the maltose binding protein, which was purified on an amylose affinity column (New England Biolabs). The 36 kDa RACK1 protein was released by proteolysis with factor Xa (New England Biolabs).

Cell Transfection Experiments

PC12 cells were transiently transfected with the plasmid encoding AChE-R, using Lipofectamine Plus (Life Technologies, Paisley, UK). Cells were lysed 24 hours following transfection in lysis buffer (0.1M phosphate buffer pH 7.4, 1% Triton X-100, and Complete mini protease inhibitor cocktail (Roche, Mannheim, Germany)). Cell debris was removed by centrifugation at 12,000× g for 10 min.

Overlay Assay

Protein samples containing recombinant RACK1 were separated by SDS-PAGE. Following blotting, the nitrocellulose membrane was incubated in a blocking solution (3% non fat dried milk, 2% BSA, 0.2% Tween-20 in Tris buffered saline (TBS, 0.1M tris pH 7.4, 1.7M NaCl)) for 1 hour. Overlay was in 6 ml of 1:20 diluted clear supernatant from homogenates of PC12 cells expressing either human AChE-R [Grifman et al. (1998) Proc Natl Acad Sci USA 95, 13935–40]. The final protein concentration was 2 mg/mL, in 50 mM Tris-HCl, pH 7.5, 0.2 M NaCl, 0.1% BSA, 0.1% polyethylene glycol (PEG), 12 mM beta-mercaptoethanol and Complete mini protease inhibitors cocktail (Roche), in a final concentration of 0.05% Triton X-100. Following incubation (1h, room temperature), unbound material was removed by 3 brief washes and three 5 min washes in 0.05% Tween-20 in TBS. Following fixation with 4% paraformaldehyde (30 min, at 4° C.), bound AChE was detected using goat polyclonal antibodies targeted to the N-terminal domain of hAChE (Cat. No. sc-6431, Santa Cruz Biotechnology, Santa Cruz, Calif.; dilution 1:500).

Co-immunoprecipitation

Clear supernatants of PC12 or COS cell homogenates (200 µL, 1.5 mg protein/mL) were prepared by manual homogenization, followed by 30 min centrifugation at 12,000× g, 4° C. Supernatants were diluted 5-fold with NET buffer (50 mM Tris-HCl, pH 7.4, 150 mM NaCl, 1 mM EDTA, 0.25% gelatin and Complete mini protease inhibitors cocktail (Roche)), in a final concentration of 0.05% Triton X-100). Goat polyclonal antibodies (Santa Cruz) targeted to the N-terminal domain of hAChE (10 µL, 200 µg/mL) were added for overnight rotation at 40C. 75 µL of Protein G MicroBeads (Miltenyi Biotec, Bergisch Galdbach, Germany) was added and incubation continued for another h. Mixtures were loaded on MACS magnetic separation columns (Miltenyi Biotec), washed 3 times with 200 µL of TBS buffer containing 0.05% Tween-20 and eluted with gel loading buffer. Elutes were separated by sodium dodecyl sulfate polyacrylamide gel electrophoresis (Bio-Rad, Hercules, Calif.), blotted and incubated with the noted detection antibodies. For immunoprecipitation, dissected mouse brain regions were homogenized in nine volumes of the lysis buffer. Homogenates were passed several times through a 21G needle. Insoluble debris was removed by a 30 min 12,000× g centrifugation. Homogenates were kept frozen at −70° C. until use.

Laboratory Animals and Stress Experiments

Male 6–8 weeks old FVB/N mice were subjected to saline injection (0.2 ml, intraperitoneal) which induces mild psychological stress in this stress-sensitive strain. Stressed mice, control and AChE-R transgenic mice [Sternfeld et al. (2000) id ibid] were sacrificed 24 h post-injection. To prepare brain sections, four mice from each line were deeply anesthetized with Pental (pentobarbitone sodium 200 mg/ml, CTS Chemical industries, Petach Tikva, Israel) at a dose of 100 mg/Kg and transcardially perfused with 4% (vol/vol) paraformaldehyde. Brains were post-fixed by immersion in 4% (vol/vol) paraformaldehyde (overnight, 2–8° C.) and incubated in 12% (vol/vol) sucrose in 0.1M phosphate buffered saline (PBS). Coronal cryostat sections (30 µm) were floated in PBS and kept at −20° C. in 40% (vol/vol) ethylene glycol and 1% polyvinylpyrrolidone in 0.1 M potassium acetate (pH 6.5) until staining.

Antibodies and Working Dilutions

Immunohistochemical analyses were essentially as previously described [Shoham and Ebstein (1997) Exp. Neurol.

147, 361–76; Sternfeld et al. (2000) id ibid.], using rabbit anti-ARP [Sternfeld et al. (2000) id ibid.] 1:100, rabbit anti PKCβII (Cat. No. sc-210, Santa Cruz) 1:100, rabbit anti PKCµII (Sigma-Rehovot, Israel) 1:250 and mouse anti RACK1 (Cat. No. R20620, Transduction Labratories, San Diego, Calif.) 1:200. Immunoblot analyses were with rabbit anti-N-terminus AChE antibodies (Cat. No. N-19, Santa Cruz), 1:500; mouse monoclonal antibody against all isoforms of PKC of mouse, rat and human origin (Cat. No. sc-80, Santa Cruz), dilution 1:100, or mouse monoclonal antibody against RACK1 (R20620,Transduction Laboratories), dilution 1:2500.

Sections were incubated with the primary antibody and then with biotin-conjugated donkey anti-rabbit antibody (Cat No. AP132B, Chemicon, Temecula, Calif.; 1 hour, room temp., overnight at 2–8° C.) and extravidin-peroxidase (Sigma). RACK1 staining was further preceded by trypsin type II treatment (Sigma), 1 µg/ml with calcium chloride 0.001% for 2 min, at room temp., which required the addition of 0.001% soybean trypsin inhibitor (Sigma) during staining. Detection was with horseradish peroxidase-conjugated goat anti-mouse antibody (1:100 dilution, Sigma). Pre-incubation of anti-RACK1 with 10 µM RACK1 for 1 h at room temp totally eliminated staining with anti-RACK1, demonstrating specificity. For all antibodies, staining was intensified with 0.075% diaminobenzidine and 0.05% nickel ammonium sulfate.

Fluorescence Double Labeling of RACK1, ARP and PKCβII

RACK1 and ARP: Primary staining solutions contained 0.001% trypsin inhibitor (Sigma type IIS), 0.3% Triton X100, 0.05% Tween 20, 2% normal goat serum, 2% normal donkey serum, rabbit anti-ARP1 (1:100) and mouse anti-RACK1 (1:100). The secondary antibody solution contained 0.3% Triton X100, 0.05% Tween 20, 2% normal goat serum, 2% normal donkey serum, donkey-anti-rabbit conjugated to fluorescein (Chemicon, AP182F) diluted 1:100 and goat-anti-mouse conjugated with tetra-methyl-rhodamine (Sigma, T7782) diluted 1:800. Sections were mounted on SuperFrost slides (Menzel Glaser, Freiburg, Germany), air-dried, covered in ImmuMount (Shandon, Pittsburgh, Pa.) and covered for microscopy.

PKCβII and ARP1: The primary staining solution contained 0.3% Triton X100, 0.05% Tween 20, 2% normal goat serum, 2% normal donkey serum, rabbit anti-ARP (1:100) and mouse-anti-PKCβII (Sigma, P8083), diluted 1:500. Secondary antibody solutions and preparation for microscopy were as specified above for ARP and RACK 1.

Example 1

Hydrocortisone Elevates ACHE Gene Expression in Hematopoietic Stem Cells

This example relates to ACHE gene expression in hematopoietic stem cells and the influence of hydrocortisone thereon. The inventors have searched the extended promoter of the human ACHE gene (cosmid accession no. AF002993) for consensus motifs that may bind stress-associated and hematopoietic transcription factors. Two such clusters, one located 17 Kb upstream from the transcription start site, and another positioned at the first intron, were found to include motifs for AP1, NFkB, EGR-1 (as identified by a matrix search against the TransFac database, Heinemeyer et al., Nucleic Acids Res. 26, 364–370, 1998), interleukin-6 (IL6), with the consensus sequence CTGGG/AAA, glucocorticoid responsive element (GRE) half palindromic site, TGTTCT, and Stat-5, TTCCCAGAA or TT(C/A)(C/T)N(A/G)(G/T)AA (FIG. 1A). Of these, the latter two motifs are known to be actively involved in hematopoiesis (Darnell et al., Science 264, 1415–21, 1994) and cellular stress responses (Tronche et al., Curr. Opin. Genet. Dev. 8, 532–8, 1998). Moreover, they act synergistically in enhancement of β-casein gene expression in hematopoietic cells (Lechner et al., Immunobiology 198, 112–23, 1997) but have not yet been studied in the context of AChE involvement in hematopoiesis.

FIG. 1A is a scheme of the upstream human ACHE sequence including clusters of hematopoietic and stress-related motifs. Depicted is a scheme of the reverse sequence of the cosmid insert (accession No. AF002993) of the human ACHE promoter. The arrow represents the position of a transcription start site. Two potentially relevant regions are shown, one beginning at nucleotide 5267 and one following the first exon (black box). Fully conserved consensus sequences are marked by triangles. These include AP-1, NF-κB, EGR-1, IL-6, glucocorticoid responsive element (GRE) half-palindromic site, and Stat-5.

The functional effects of the glucocorticoid-binding motifs in the ACHE upstream sequence (FIG. 1A) were investigated in human UCB $CD34^+$ stem cells isolated by anti-CD34-coated immunobeads to yield a 85±3% pure population, as confirmed by flow cytometry. $CD34^+$ cells were enriched from human UCB cells using bead-attached antibodies to the CD34 protein.

FIG. 1B shows a representative flow cytometry of the recovered cells, demonstrating that 89% of them express the CD34 antigen. The inset in FIG. 1B shows an example photograph of enriched $CD34^+$ cells stained by May-Grün-wald-Giemsa. Note the large nuclei surrounded by thin rims of cytoplasm, characteristic of stem cells.

Enriched $CD34^+$ cells were subjected to cytochemical staining for AChE catalytic activity in the presence of $10^{-5}$ M iso-OMPA (FIG. 1C, ISO) or BW284C51 (FIG. 1C, BW), selective inhibitors of BuChE and AChE, respectively. Nuclear staining (FIG. 1C, right) was with DAPI. Note the selective appearance of brown precipitates of AChE, but not BuChE reaction products. The data shown in FIG. 1C demonstrate that $CD34^+$ cells contain cytochemically detectable levels of catalytically active AChE. The identity of their cholinesterase as AChE was verified by its sensitivity to the AChE-specific inhibitor BW284C51 and its resistance to the butyryl-cholinesterase (BuChE) inhibitor iso-OMPA (FIG. 1C).

The assumption that hematopoietic ACHE gene expression is modulated under stress was tested in $CD34^+$ cells cultured for 24 hr with increasing doses of hydrocortisone. Treated cells were subjected to cytochemical staining for AChE activity as well as to high resolution in situ hybridization followed by confocal microscopic quantification of labeling density. This method provides an accurate and credible tool for the examination of transcriptional responses in the heterogeneous population of primary HSCs from different individuals. Hybridizations were performed for each of the three transcripts of human AChEmRNA presented in FIG. 1A (S, E and R). Because each cRNA probe has its own characteristic hybridization affinity, each transcript was quantified separately. Individual $CD34^+$ cells were treated with the noted doses of hydrocortisone at levels equivalent to physiologically normal, intermediate and stress conditions (0.1, 0.6 and 1.21 µM, respectively; see De Vroede et al., ibid, 1998). Cells were subjected to in situ hybridization with the noted AChEcRNA probes, followed by confocal microscopy, projection of image slices, quantification and color-coding of the labeling signals.

FIG. 1D presents cytochemically stained cells (top) and representations of 3-dimensional projections created from confocally scanned sections of CD34⁺ cells following in situ hybridization with 5'-biotinylated AChEcRNA probes selective for the "synaptic" AChE-S mRNA variant, the "erythrocytic" AChE-E mRNA variant encoding for glycophospholipid-anchored AChE-E and the "readthrough" AChE-R mRNA form associated with stress. Detection was by appearance of Fast Red precipitates [Grisaru et al. (1999b) id ibid.]. Note increasing cytoplasmic labeling under high hydrocortisone levels. Each photograph represents one out of 10–20 analyzed cells with deviations in labeling of less than 6%. FIG. 1D, left, bottom shows the relative increases in percent above control for each of the analyzed transcripts under stress-relevant concentrations. Note the accumulation of AChE-R mRNA transcripts under moderate hydrocortisone concentrations.

FIG. 1D demonstrates that subtle elevation of hydrocortisone concentration to 0.60 1 µM induced a 40% selective increase in the "readthrough" AChE-R mRNA transcript above the level observed under non-stress hydrocortisone concentration (0.10 µM) [De Vroede et al. (1998) *Arch. Dis. Child* 78, 544–7]. However, at 0.60 µM hydrocortisone, no change was observed in enzyme activity of CD34⁺ cells. In contrast, stress-associated hydrocortisone levels (1.2 µM) enhanced the labeling of all 3 AChEmRNA transcripts and intensified the catalytic activity of the stem cell-associated enzyme. The AChE-R mRNA-specific in situ hybridization, therefore detects a clear increase in this variant against a low background, while total cell-bound enzyme activity registers no deviation from background at a sub-stress hydrocortisone level.

Example 2

Expression of ARP in CD34⁺ Cells

The expression of ARP in CD34⁺ hematopoietic cells was evaluated by flow cytometry in whole cord blood and bone marrow from a patient with immune thrombocytopenic purpura (ITP), as demonstrated in FIG. 2A and FIG. 2B respectively. Bone marrow from ITP patients was chosen to study ARP expression in hematopoietic progenitor cells due to the high turnover of normal CD34⁺ in these patients. Cells were fixed and permeabiliazed with Fix and Perm (Caltag, Calif) and stained with moncoclonal antibodies to CD34 conjugated to pycoerythrin (Beckton Dickinson, Calif. indicated as FL-2 and with highly specific rabbit anti-ARP antibodies followed by anti rabbit antibodies conjugated to fluoroscein isothiocyanate, expression indicated as percentage of positive cells.

These findings demonstrate higher expression of AChE-R in proliferating hematopoietic progenitors from either newborns or individuals suffering from over-proliferation of blood cells.

Example 3

Readthrough AChE is Overproduced in the Myeloidogenic Mid-Gestation Liver

To study the relevance of each of the AChEmRNA transcripts during development of the hematopoietic organs, in situ hybridization was performed on paraffin-embedded sections taken from human fetuses at different gestational ages. Consistent with the embryonic spatiotemporal shifts in blood cell forming tissues, we observed changes in the labeling intensity with the various probes used, in the aorta-gonad-mesonephric region (AGM), liver, spleen and bone marrow cells. FIG. 3A schematically presents the migration of hematopoiesis between the various blood cell forming tissues during fetal development. The top left of the figure represents a sagittal section of a human embryo showing the hematopoietic organs—AGM (aorta-gonad-mesonephros), LIV (liver), SPL (spleen), and BM (bone marrow). The top right of the figure is a scheme of gestational shifts in hematopoietic processes which shows the relative intensity of blood cell formation in the various hematopoietic organs throughout human gestation. (according to Tavassoli et al., Blood Cells 17, 269–81, 1991, Tavian et al. Development 126, 793–803, 1999). Ages of embryos on which in situ hybridization was performed are marked by gray columns.

FIG. 3B presents in situ hybridization results and the average labeling intensities for the AChE-S, AChE-E and AChE-R mRNA transcripts in AGM (triangles, week 9), liver (diamonds), spleen (squares) and bone marrow (triangles, weeks 20–25) of human fetuses at different gestational ages (right side curves). The figure shows representative in situ hybridization micrographs from the noted tissues of human fetuses at the noted gestational ages, using selective probes for each of the above alternative human AChEmRNA transcripts. The right side of the figure shows spatiotemporal changes in labeling intensity for each probe and organ. Note that AChEmRNA expression increases parallel to active hematopoiesis in the examined organs.

For the AChE-S and AChE-E probes, expression levels were distributed similarly in liver and spleen. For example, labeling intensity for both these probes was high in mid-gestation liver and spleen, when the principal hematopoietic activity was erythropoiesis, and labeling of both decreased steadily from the 9$^{th}$ week onward, as myelopoiesis became more prevalent. In contrast, the AChE-R transcript was detected only during the 16 week transition from erythro- to myelopoiesis in the mid-gestation liver and not in the spleen (Porcellini et al., Int. J. Cell Cloning 1, 92–104, 1983). The unique expression pattern of AChE-R mRNA and its apparent correlation with myeloidogenesis demonstrated that AChE-R acts as a selective hematopoietic element.

Example 4

ARP Sustains Cell Expansion and Differentiation

The predicted secondary structure of peptides ARP and ASP was analyzed. FIG. 4A presents the amino acid sequences of ARP and ASP (26 and 40 residues, respectively). Secondary structure predicted using the peptide structure program of the GCG software package (University of Wisconsin) was based on the Chou-Fasman method. Depicted below the sequences are the secondary structures predicted: T, turn, B, β-sheet and H, α-helix, with lower case letters representing lower predicted probability. Note the predicted helix structure for the first 17 residues of ASP, drawn using the Helicalwheel program of the GCG software package. The amphipathic nature of this region is postulated based on the unilateral positioning of hydrophobic residues (F, L, W, W, A).

Both the "synaptic" exon 6-derived and the "readthrough" pseudointron 4-derived peptides (ASP, ARP) include a major region predicted to be rich in turns and β-pleated sheets; in addition, the longer ASP peptide is predicted to contain a unilaterally hydrophobic α-helical domain with amphipathic properties (FIG. 4A). To test whether either of these peptides has biological activity, the inventors added HPLC-purified synthetic peptides (in 50 and 100 ng/ml final concentrations) once every 4 days to the growth medium in which isolated HSCs (CD34$^+$) were cultured for 2 weeks. FIG. 4B shows fold expansion values of viable cells, based on trypan blue exclusion (average of 4–5 experiments±standard error of the mean, SEM) grown for 2 weeks in the presence of the noted growth factor or mixtures of factors and, where marked, 50 ng/ml ASP or ARP. Asterisks note statistical significance of the measured increases in cell counts as compared to cultures without the peptide ($p \leq 0.05$).

The effect of ARP on cell proliferation was further analyzed using BrdU incorporation assay. BrdU incorporation was measured by 5-Bromo-2'-deoxy-Uridine Labeling and Detection Kit III, Roche.

As shown in Table 1, ARP, but not ASP, facilitates BrdU incorporation into cord blood progenitors. ARP induces similar effects on BrdU incorporation into CD34$^+$ progenitors from the peripheral blood of adult donors.

TABLE 1

The effect of ARP on BrdU incorporation to CD34$^+$ cells

| P | hrs post-plating | ARP, 2 nM | ASP, 2 nM | None |
|---|---|---|---|---|
|  | 16 | 0.110 ± 0.005 | 0.095 ± 0.004 | 0.135 ± 0.005 |
| 0.05 | 24 | 0.275 ± 0.045 | 0.182 ± 0.018 | 0.212 ± 0.026 |
| 0.018 | 36 | 0.423 ± 0.099 | 0.260 ± 0.022 | 0.246 ± 0.035 |

Shown are BrdU incorporation values following the noted incubation times.

In addition, the effect of ARP was examined in transformed bone marrow endothelial cells (Schweitzer et al, Lab Invest vol. 76, 5–36:1997). Cells were incubated in a serum free medium (SFM) with 2 nM of ARP, with or without endothelial growth factors (bFGF 20 ng/ml and EGF 10 ng/ml), for 48 hrs. As shown in FIG. 5, BrdU uptake increased in ARP presence. The effect was more pronounced when ARP was combined with bFGF and EGF.

Thus, ARP may serve as a proliferating factor for endothelial cells, having the most dramatic effect when working in synergy with the "classical" endothelial growth factors.

Addition of ARP alone increased the number of viable cells more than 10-fold (FIG. 4B; p<0.008). ARP further improved expansion of viable cells when it was administered in combination with SCF, granulocyte-macrophage colony stimulating factor (GM-CSF), bFGF and EGF or thrombopoietin (TPO). However, its growth factor-accessory effect reached statistical significance only with TPO (p<0.01). Similar doses of ASP were less effective than ARP in promoting cell expansion, alone or when added with any combination of these cytokines for 2 weeks (FIG. 4B and Table 1).

The compatibility of the ARP-supported expansion with differentiation was tested by quantifying the myeloid (CD33$^+$) and megakaryocytic (MK, CD41$^+$) cells after 2 weeks in liquid culture (Table 2). Cells expanded under the influence of ARP displayed increased ability to differentiate into MK and myeloid progeny. Moreover, ARP potentiated the effect of TPO to enhance the number of MKs. Surprisingly, the TPO-potentiating effect of ARP was found to be more pronounced than the TPO-potentiating effect of stem cell factor (SCF). SCF is a known TPO potentiating agent for stem cells (Deutsch et al., Med. Oncol. 13, 31–42, 1996). ARP also facilitated the capacity of GM-CSF and SCF to support myelopoiesis. Thus, the effects of ARP over MK (p=0.08, paired Student's t-Test) and myeloid (p=0.04) expansion are independent. Further, the effect of ARP on the megakaryocytopoietic capacity of TPO and SCF (p=0.03) is synergistic. The myeloid potentiation capacity of ARP over that of GM-CSF and SCF is additive.

TABLE 2

ARP potentiates TPO, GM-CSF and SOF effects on megakaryocytic and myeloid lineages[a]

| cytokine | cell type | |
|---|---|---|
|  | MK (CD41$^+$) | Myeloid (CD33$^+$) |
| None | 0.03 ± 0.02 | 1.50 ± 0.79 |
| ARP | 8.20 ± 4.50 | 2.90 ± 0.65 |
| TPO | 3.93 ± 3.56 | 3.51 ± 2.23 |
| TPO + APP | 48.43 ± 34.94 | 2.95 ± 0.64 |
| GM-CSF | 14.50 | 1.35 |
| GM-CSF + ARP | 7.80 | 1.98 |
| SCF | 0.30 ± 0.21 | 3.90 |
| SCF + ARP | 0.90 ± 0.27 | 6.49 |
| SCF + TPO | 20.60 ± 20.04 | 0.68 |

[a]Presented are fold expansions (and, where noted, SEMs) of 2-week primary cultures of CD34$^+$ cells from 1 to 3 individuals grown with the noted cytokines. ARP, AChE C-terminal "readthrough" peptide; TPO, thrombopoietin; GM-CSF, granulocyte- macrophage colony stimulating factor; SCF, stem cell factor; MK, megakaryocyte. Potentiated expansion values are highlighted in bold letters.

Example 5

Autoregulatory Effect of ARP

ARP was added in concentrations of 50 or 100 ng/ml to cultured CD34$^+$ cells and the levels of the various AChEmRNA transcripts after 24 hr were examined, by in situ hybridization combined with confocal microscopy analysis. FIG. 6 (left) shows representative individual CD34$^+$ cells treated for 24 hr with the noted doses of ARP in the absence of other growth factors and subjected to in situ hybridization with probes selective for each of the alternatively spliced variants of AChEmRNA. The right side of the figure shows average labeling densities for 10–20 cells in each case. FIG. 6 demonstrates similar increases for all 3 transcripts (S,E,R) with peak activity at 50 ng/ml ARP. Note the concomitant increases in all transcripts, and the uniform nature of this response in all of the analyzed cells. This suggests that ARP stimulates transcriptional enhancement of the ACHE gene. Autoregulatory continuation of AChE-R production could sustain the ARP effect long after the initial ARP signal has been terminated.

Example 6

ARP Retrieves the Antisense-Suppressed Cell Proliferation Effect of GM-CSF

Antisense Suppression of ACHE-R Production

The ARP-induced enhancement of ACHE gene expression suggested that the AChE-R protein and not necessarily ARP, may be responsible for the sustained viability and the significant expansion of HSCs. To distinguish between these two possibilities, the inventors employed antisense oligodeoxynucleotides (AS-ODN) to selectively suppress AChE-R mRNA levels, reduce the intracellular production of AChE-R and test, under these conditions, the proliferative effects of GM-CSF with or without ARP. AChE-R mRNA includes a 1,094 bp 3'-untranslated region (UTR), with 62% G,C content. This marks it as a more vulnerable molecule to nucleolytic degradation than AChE-S mRNA, which includes a 219 bp UTR with 66% G,C. A. FIG. 7A shows AS-ODNs targeted to the common sequence domain of mRNA transcripts with variable UTRs. Shown are schematic structures of the two human cholinesterase genes, ACHE and BCHE. Exons are colored or gray, introns are shown in white. The open reading frame (ORF) is drawn above each gene, and the positions and predicted structures of the AS-ODNs that were employed are drawn below. Also marked are the UTRs for the two AChEmRNA transcripts, AChE-S (UTR=219 bp, 66% G, C) and AChE-R (UTR=1, 094 bp, 62% G, C).

To selectively reduce AChE-R mRNA levels in HSCs, extremely low doses (20 pM) of anti-AChEmRNA AS-ODNs [Grisaru et al. (1999b) id ibid.] were employed. AS1 and AS3 are 2'-O-methyl-protected AS-ODNs targeted to ACHE exon 2, which is common for AChE-S and AChE-R mRNA. An irrelevant AS-ODN (ASB) targeted to BuChE mRNA served as a control (FIG. 7A and [Grisaru et al. (1999b) id ibid.]. FIG. 7B shows selective susceptibility of AChE-R mRNA to AS-ODN destruction. CD34$^+$ stem cells were treated for 24 hr at 37° C. with 20 pM 2'-O-methylated AS-ODNs targeted to AChEmRNA or BuChEmRNA. Shown are DAPI and AChE activity stainings (left) and confocal images of in situ hybridizations for the AChE-S and AChE-R transcripts (right) with 20 pM of the ASB, AS1 or AS3 AS-ODNs. Columns show average levels of staining efficiencies for 10–20 cells hybridized with each of the transcript-specific probes. Note maintenance of cell-associated AChE activities and stable levels of AChE-S mRNA under all treatments as opposed to selective reduction of AChE-R mRNA under AS1 treatment. Thus, AS1, but not AS3 reduced the in situ detected AChE-R mRNA levels in CD34$^+$ cells under conditions where AChE-S mRNA levels remained unchanged (FIG. 7B). The irrelevant ASB ODN was ineffective, demonstrating sequence specificity of the AS1 effect.

ARP Retrieves the Antisense-Suppressed Cell Proliferation Effect of GM-CSF

Cell proliferation was evaluated by measuring BrdU incorporation following 16 hr incubation in the presence of 20 pM of the noted AS-ODNs with or without 50 ng/ml ARP and/or GM-CSF. FIG. 7C shows average results of 3–6 reproducible experiments ± SEM. Consistent with its expansion effect, incubation with GM-CSF increased the incorporation of bromodeoxyuracil (BrdU) into CD34$^+$ cells over 16 hr (FIG. 7C). Addition of 50 ng/ml ARP together with GM-CSF significantly potentiated this incorporation ($p<0.03$), whereas ARP, AS1, AS3 or ASB did not affect BrdU incorporation when added alone to the cells (FIG. 7C). The capacity of GM-CSF to enhance BrdU incorporation was totally suppressed when it was added together with 20 pM AS1. The suppressive effect of AS3 on GM-CSF-induced enhancement of BrdU incorporation, was much weaker than that of AS1, consistent with its inability to suppress AChE-R mRNA levels in CD34$^+$ cells. To examine whether ARP alone was required and sufficient to facilitate the cell proliferation effect of GM-CSF, the inventors incubated the cells with GM-CSF and ARP together with the suppressive AS1. ARP completely reversed the AS1-induced suppression in BrdU incorporation, retrieving the full capacity of GM-CSF to enhance cell proliferation (FIG. 7C).

Thus, the data show that ARP enhances the GM-CSF-supported increases in cell proliferation, that AS1 reduces this enhancement far more effectively than AS3, and that ARP retrieves the AS1-suppressed proliferation.

Example 7

ARP can Substitute for Stem Cell Factor

To determine whether the ARP expansion effects could replace any of the known growth factors, the inventors tested ARP alone or combined with known growth factors, on long-term CD34$^+$ cell cultures. FIG. 8A shows cell counts from long-term CD34$^+$ liquid cultures grown in the absence of growth factors (diamonds), in the presence of early-acting cytokines (EAC: IL3, IL6, TPO and FLT3) and SCF (squares), or in the presence of EAC+ARP with SCF (circles) or in the presence of EAC+ARP without SCF (triangles). Viable cell counts are depicted in the upper left part of FIG. 8A. CD34$^+$ cell counts are presented in the upper right part of the figure. The lower left and right parts are graphs of the number of Granulocyte-Marcophage (GM) or Megakaryocyte (MK) progenitor colony forming units.

FIG. 8A, upper left, shows that early-acting cytokines (a mixture of IL3, IL6, TPO and FLT3) promote linear expansion of CD34$^+$ cells for up to 28 days. In the absence of this mixture, there was no proliferation. SCF, although devoid of proliferative activity by itself, enhances significantly the proliferation induced by the above growth factors (Li and Johnson, Blood 84, 408–14, 1994). Addition of ARP, with or without SCF resulted in an enhanced cellular proliferation, leading in both cases to a greater than 2000-fold expansion within 28 days (FIG. 8A, upper left). This demonstrates that the activity of ARP was additive to that of the early-acting cytokines and that it could replace SCF.

FIG. 8A, upper right, shows that ARP operates as a CD34$^+$ survival factor. Note that CD34$^+$ cell numbers reach a plateau at 21 days in the presence of EAC (squares), and that ARP facilitates further increases in CD34$^+$ counts up to at least 28 days, regardless of the presence of SCF (triangles, circles). Thus, the conclusions drawn above from the results of FIG. 8A, upper left, are supported by the finding that ARP with or without SCF promoted, with similar efficacy, the survival of CD34$^+$ cells within the expanded cultures as compared with survival in the absence of growth factors (FIG. 8A, upper right).

FIG. 8A, lower part, show that ARP increases the number of GM and MK progenitors. Shown are counts of colony forming units for GM (left) or MK (right) colonies grown from progenitors removed at 13, 21 and 28 days of the primary expansion phase detailed under FIG. 8A. The numbers of colonies grown after EAC, EAC+SCF+ARP or EAC+ARP treatment are very similar, suggesting redundant expansion properties for SCF and ARP.

FIG. 8B shows that ARP facilitates development of hematon bodies. Representative photographs of the 28-day liquid cultures detailed in FIG. 8A above are shown. In the absence of growth factors, sparse hematopoietic cells and many fibroblasts are seen (control, upper left). Addition of EAC increases the density of small, round hematopoietic stem cells and sparse MKs (FIG. 8B, upper right, white arrow). FIG. 6B, lower half, demonstrates that EAC+ARP facilitate the formation of hematon bodies (insets) without (right) or with SCF (left).

FIG. 8A, lower part, shows that ARP increases the number of GM and MK progenitors. Shown are counts of colony forming units for GM (left) or MK (right) colonies grown from progenitors removed at 13, 21 and 28 days of the primary expansion phase detailed under FIG. 8A. The numbers of colonies grown after EAC, EAC+SCF+ARP or EAC+ARP treatment are very similar, suggesting redundant expansion properties for SCF and ARP.

In summary, CD34+ cultures grown without growth factors for 28 days displayed typical fibroblast morphology (FIG. 8B, Upper left). In contrast, a dense population of small, round cells, with characteristic stem cell morphology, was observed in cultures grown for the same period in the presence of the early-acting cytokines (FIG. 8B, Upper right). The addition of ARP, in the presence or absence of SCF, sustained this stem cell morphology (FIG. 8B, Lower left and right). Interestingly, floating "hematons", which are independent hematopoietic units rich in myeloid, erythroid and megakaryocyte progenitor cells (Blazsek et al., Exp. Hematol. 23, 309–19, 1995) were found in the ARP-containing cultures, demonstrating the differentiation potential of this peptide (FIG. 8B, lower part, insets).

Example 8

ARP-treated Cells Maintain Multipotent Progenitor Properties

To test the number of progenitors and differentiation routes available to ARP-treated cells, the inventors subjected the above cultures to a second expansion phase. Cells removed once a week from the primary liquid cultures were grown in the absence of ARP in a semi-solid substrate. In the absence of the growth factor mixture, there was no secondary expansion. IL3 and GM-CSF were used to induce granulocyte-macrophage (GM) expansion and TPO and SCF was used for megakaryocyte (MK) expansion. During this second expansion phase, blood cell progenitors that had previously been treated with early-acting cytokines developed into either GM or MK colonies (FIG. 8B, lower part), depending upon the added growth factor. The numbers of GM and MK colonies peaked by 3 weeks and were essentially the same in cultures that were previously treated with all of the early acting cytokines, with or without ARP. ARP-supported hematopoiesis thus appeared to maintain normal growth of differentiated myeloid and megakaryocyte colonies.

These tests provide evidence for maintenance of all type of progenitors in ARP-treated cultures.

TABLE 3

The effect of various conditions on cultured cell count[a]

| Treatment | Total viable cells | CD34+ (early progenitors) | CD33+ (early myeloids) | CD33+ and CD15+ (total myeloids) | CD41+ (megakaryocytes) |
|---|---|---|---|---|---|
| Control | 61.0 | 1.0 | 7.2 | 12.3 | 30.9 |
| ARP, 2 nM | 570.0 | 87.2 | 329.0 | 530.0 | 42.3[b] |
| cortisol, 1.2 µM | 80.0 | 13.0 | 45.0 | 73.0 | 10.1[b] |
| ASP, 2 nM | 100.0 | 7.2 | 10.0 | 13.0 | 4.6[b] |
| SCF, 50 ng/ml | 118.0 | 6.3 | 69.0 | 72.0 | 2.6[b] |
| AS1, 20 pM | 81.2 | 1.4 | 2.4 | 5.0 | 30.9 |
| PBAN, 2 nM | 105.0 | 1.7 | 1.6 | 3.1 | 52.9 |

[a]Cultures were seeded at 50,000 cells/well. Shown are cells per culture × $10^{-3}$ on day 14; 1 of 3 reproducible experiments as in the figure above.
[b]These are also CD34+ positive early cells with expansion potential.

Example 9

In vivo Effects of ARP and ASP on Embryonic Brain Development

In order to study the possible involvement of ARP in the embryonic development process, the anti-ARP and anti-ASP antibodies have been used to label structures in the embryonic mouse cortex. These antibodies can label either cell types that produce AChE-R and AChE-S, or cells that have binding sites for the ARP and ASP peptides.

In the dorsolateral nercortex, neurons migrate from the lateral cortical stream toward the outer perimeter of the brain. FIG. 9A shows that at embryonic day 14, the neuron bodies, which lie toward the perimeter of the brain, have AChE-S, whereas, the entire region, from the subventricular zone to the perimeter, expresses AChE-R.

BrdU Labeling in Developing Brain

In order to study the effect of ARP on mitotic activity of developing mouse brain, a BrdU incorporation analysis was performed. The C-terminal peptides ARP or ASP were injected 0.1 mg/Kg into a pregnant mouse; 24 hr later, the BrdU was injected and after 1 hr the embryo was isolated and fixed for examination. To show specificity of the results for the peptides, the experiments were performed in the presence of antisense oligonucleotides. The AS3 ODN, 2 nM, was injected into a pregnant mouse and 5 hr later the BrdU. After 1 hr the embryo was isolated and fixed. Controls were saline injection or an ODN with the inverse sequence of the AS3. Labeled neurons (positive for BrdU incorporation) were counted to assess neuronal proliferation.

Embryonic neuroepithelial cells have one of two fates: (1) to continue proliferation and migration up and down from the ventricular zone up to the cortical plate, or (2) to quit the proliferative cycle and initiate terminal differentiation. The balance between these two processes determines the number of proliferating neuronal progenitors as well as the thickness of the cortical plate where post-mitotic neurons accumulate (see scheme at FIG. 10).

As shown in FIG. 9B, ASP has minor positive effect on proliferating neurons, evidenced in the increased number of BrdU labeled nuclei. ARP enhances neuronal proliferation, yet more significantly, while reducing the thickness of the cortical region harboring differentiating post-mitotic neurons.

AS3, an ODN directed toward a sequence common to both AChE-S and AChE-R, much more effectively suppresses the mRNA of AChE-R than that of AChE-S [Shohami et al. (2000) J. Mol. Med. 78, 228–36]. The suppression of AChE-R is correlated with an increased thickness of the layer of post-mitotic neurons compare to control sections (reproducible outcome from one of three animals used for each treatment).

Immunolabeling of ARP in Treated Brain

To confirm that the antisense treatment suppresses the level of ARP production and that this occurs through destruction of AChE-R mRNA, in situ hybridization and immunolabeling were performed.

FIG. 11A presents labeling pattern of the embryonic brain stained with the anti-ARP antibody after AS3 treatment (right) or in controls (left). This Figure demonstrates that the AChE protein is suppressed by the AS-ODN treatment, and that in the developing cortex, it was concentrated mainly in post-mitotic neurons but may also be visualized along the migratory pathway leading to this layer from the ventricular zone.

Furthermore, FIG. 11B presents an in situ hybridization analysis showing antisense suppression of AChE-R mRNA in the embryonic brain. Also here, post-mitotic neurons are the only cells to express AChE-R mRNA and this expression is completely suppressed following AS3 treatment.

Example 10

In vivo ARP Effects

ARP Accumulates in the Serum under Stress and Facilitates the Stress-Induced Hematopoietic Responses in vivo To find out whether the ARP peptide occurs naturally in blood and if its levels increase under psychological stress, FVB/N mice (n=12) were subjected to confined swim protocol for exerting acute psychological stress as detailed elsewhere [Kaufer et al.(1998) id ibid.]. Serum samples removed 24 hr later were subjected to gradient gel electrophoresis. FIG. 11A, top, shows a Poinceau-stained polyacrylamide gradient gel (4–20%, Bio-Rad) loaded with: (1) protein extract from COS cells transfected with AChE-R encoding plasmid (Ben Aziz-Aloya et al., Proc. Natl. Acad. Sci. USA 90, 2471–5, 1993, Seidman et al., Mol. Cell. Biol. 15, 2993–3002, 1995) and mixed with synthetic ARP (ARP+ AChE-R); (2) recombinant AChE-S (Sigma), mixed with synthetic ASP (ASP+AChE-S); (3) serum (2 μL) from a saline-injected mouse, removed 24 hr post-treatment (Control); (4) serum from a mouse subjected to confined-swim stress as described above, removed 24 hr post-treatment (Stress). Positions of molecular weight markers are shown on the left. The gel was then electroblotted and immunodetected (see "immunoblot" in the Experimental Procedures section for details) with affinity-purified rabbit antibodies elicited toward a recombinant GST-ARP fusion protein (FIG. 11A, bottom). A 67 KDa protein, consistent with the expected size of AChE-R, is detected in the serum (upper arrow). Furthermore, selective labeling of synthetic ARP (but not AChE-S or ASP) by this antibody is detected. Accumulation of ARP in the serum of stressed mice is evident from the intense labeling of native ARP in the stressed mouse serum (lower arrow).

To determine the in vivo capacity of ARP to affect hematopoietic expansion under acute psychological trauma, mice were injected immediately after the stress protocol with 0.1 mg/kg ARP or 30 ng/kg AS1. Another group of mice were not subjected to stress and were injected intraperitoneally with normal saline (n=6) or ARP (n=4). 24 hours later, the animals were sacrificed and whole blood obtained for AChE activity and white blood cells. Bone marrow smears were subjected to immunohistochemical labeling with an affinity purified rabbit antiserum prepared against GST-fused recombinant ARP. FIG. 12B shows the number of labeled cells per 100 cells counted at ×1000 magnification in 5 different fields. Bone-marrow labeling and white blood cell (WBC) count were similar in non-stressed mice regardless of ARP injection. In contrast, ARP intensified labeling and increased the number of small positive cells in the bone marrow of stressed mice, indicating that it enhances AChE expression and increases stem cell expansion in vivo. AS1 reduced the number of cells labeled with anti-ARP antibodies (FIG. 12B). In peripheral blood, WBC counts revealed similar ARP-dependent enhancement and AS1 suppression.

Persistent AChE-R Overproduction Increases Platelet and WBC Counts in a Dose-dependent Manner A series of AChE transgenic mouse pedigrees [Sternfeld et al. (1998b) id ibid.] was employed, to reveal if chronic increases in AChE-R would confer persistent changes in blood cell composition. Blood AChE levels, platelet and WBC counts were determined in FVB/N mice (Control, n=22) as compared to transgenic FVB/N mice carrying the AChE-S (TG-S, n=12), AChE-R (TG-R70 and TG-R45, n=9 and 6, respectively) or inert-inactivated AChE-S (AChE-Sin, n=3) transgenes. FIG. 12C shows results expressed as average+standard error of the mean (SEM). The transgenic lines expressing AChE-S variants indicated no increases in blood AChE and no significant deviations from a normal blood cell composition. In contrast, increases of 2.5 and 130-fold catalytic AChE activities were observed in two pedigrees (TG-R45 and TG-70R), whereas WBC counts were only increased in the more efficiently overproducing line, suggesting a gene dose dependent effect for ARP over the hematopoietic balance also under chronic excess conditions (FIG. 12C).

ARP Accumulation in the Serum Under Stress

The intense labeling of ARP in the unfractionated mouse serum removed 24 hr following stress treatment revealed more pronounced increases in this peptide than in its native protein AChE-R. This may reflect elevated proteolytic activity under stress. Combined with the absence of cleavage sites for common proteases within the ARP sequence, this further explains the reproducible series of proteolytic degradation products of serum AChE-R which were intensified in the stressed serum samples. The physiological implications of this finding are that AChE catalytic activity measurements are underestimates of the extent of its overproduction in the blood under stress. Likewise, measuring acetylcholine hydrolysis may underestimate the actual amounts of the AChE protein and its degradation products in the brain or muscle. The reported decreases of AChE activity in Alzheimer's disease may hence mislead researchers and clinicians alike by masking the accumulation of morphologically active AChE-derived peptides with long-term effects.

ARP Accumulation in Human Blood Plasma under Lipopolysaccharide Exposure

To test whether ARP accumulation can be observed in different stress causing situations (as demonstrated above), ARP expression and AChE activity were analyzed in human serum following exposure to bacterial lipopolysaccharide (LPS) as a model for bacterial infection.

Twenty volunteers, ages 19 to 30 years old were i.v. injected with a placebo or endotoxin (*Salmonella abortus equi.*, 0.8 ng/Kg body weight). Blood was collected at baseline, and at hourly intervals up to 10 hr post-injection.

ARP levels and AChE activity were analysed, as shown hereunder. In addition, the emotional and behavioral states of those twenty volunteers were assessed, as well as rectal temprature, heart rate and plasma levels of cytokines and cortisol (not shown).

FIG. 17A demonstrates analysis of the plasma AChE activities. The level of AChE activity in all samples was determined in the presence of $10^{-5}$M iso-OMPA and for each individual was compared to the placebo injection performed within 10 days (* denotes statistical significance). Significant increase in the AChE activity in the LPS exposed samples is shown. Blood samples were taken from one volunteer at the noted time points following injection of saline or a lipopolysaccharide. Plasma prepared from these blood samples was electrophoresed by SDS-PAGE, and the gel was immunoreacted with anti-ARP-GST antibodies (FIG. 13B). The right lanes indicate the response to a placebo injection and the next set represents the response to injection of LPS. The two right lanes show the reaction with recombinant AChE-R but not with AChE-S, respectively. This significant increase in ARP accumulation in the LPS exposed serum indicates increase in the ARP cleavage, suggesting that it may also increase under bacterial infection.

Interestingly during this experiment, it has been found by the inventors that in conjuction with the accumulation of ARP, endotoxin induced a significant increase in rectal temperature and elevation in cortisol and cytokines levels (data not shown).

Moreover, a significant endotoxin-induced increase in anxiety level was observed at 1–2 hr post-injection but not later as well as significant increase in depressed mood, which was evident at 3–4 hr post injection.

These endotoxin-induced emotional and cognitive disturbances in healthy volunteers were associated with increased plasma levels of AChE-R and cortisol (data not shown).

However, the observed correlations between depressed mood and cortisol secretion, as well as between depressed mood and cytokine secretion, suggesting that AChE-R and cortisol are independently associated with endotoxin-induced increase in depressed mood.

Mass Spectroscopy of Gel-eluted Band

To verify the identity of the plasma-accumulated short peptide that immunoreacted with the anti-ARP antibodies, larger plasma samples (180 μg/lane) were electrophoresed. A Poinceau-stained band that co-migrated with the ARP Ab-positive band was cut out of the gel and subjected to electron spray mass spectrometry. As shown in FIG. 13C, this analysis verified the existence of a peptide having a molecular mass of 3611 in the excised band. Calculation of predicted masses presents the presumed proteolytic cleavage site 36 residues from the C-terminus of AChE-R, between asparagine and arginine residues: N↓RFLPKLLSATGMQGPAGSGWEEGSGSPPGVTPLFSP, also denoted as SEQ ID: No 6.

ARP Modulations Potentiate the in vivo Hematopoietic Responses to Stress

While ARP alone did not exert immediate effects on mouse blood cell composition, its injection under stress enhanced ARP labeling in bone marrow cells and induced an elevation in WBC counts within 24 hr. This suggests that acute stress modifies the number and/or state of ARP-responsive elements on hematopoietic cells. Anti-ARP antibodies labeled primarily small cells in ARP-treated stressed animals, whereas the limited labeling in untreated stressed animals and in AS1-treated stressed animals only appeared in relatively larger cells. This indicates labeling of the stem cells which expanded during the 24 hr post-stress. The similar patterns of the in vivo effects on bone-marrow ARP labeling and WBC counts with the ex vivo expansion effects on CD34$^+$ cells implies that stress-induced increases in AChE-R may be causally related to the post-stress elevation in WBC counts (Goldberg et al., Folia Biol. 36, 319–31, 1990).

Transgenic animal models used here provide an opportunity for testing the chronic effects of elevations of different AChE variants. While AChE-S had no apparent effect on either platelet or WBC counts, AChE-R modulations exerted dose dependent changes: 2.5-fold excess in blood AChE-R activity, similar to the AChE-R elevation noted in the mouse brain under stress [Kaufer et al. (1998) id ibid] sufficed to significantly elevate platelet counts. The more dramatic 130-fold excess in blood AChE-R levels of the robust-producing transgenic pedigree [Sternfeld et al. (1998b) id ibid.] elevated both platelet and WBC counts. This finding, and the in vivo accumulation of ARP under stress, raise the possibility that the increased risk for brain infarcts following acute stress or exposure to anticholinesterases (Harmsen et al., Stroke 21, 223–9, 1990, Schultz et al., Anesthesiology 79, 114–21, 1993) is associated with the increased platelet counts due to AChE-R overproduction. This calls for a search for AChE-R overproduction in Alzheimer's disease patients, where ARP may increase platelet counts and cause the cerebral infarcts, characteristic of this disease (Inestrosa et al., Neurosci Lett 163, 8–10, 1993, Snowdon et al., Jama 277, 813–7, 1997). Anti-ARP antibodies provide a novel diagnostic tool for testing this option (and for risk assessment) and AS-ODN treatment may offer an attractive protocol for prevention of such adverse responses.

The significance of ARP extends beyond the hematopoietic system. There is evidence for cross-talk between hematopoietic cells at different stages of differentiation and bone-marrow stromal or endothelial cells. Stroma influences cytokine production and is responsible for maintaining steady-state hematopoiesis and its adjustment under stress (Gupta et al., Blood 91, 3724–33, 1998). It has been proposed that primitive CD34$^+$ progenitors provide a soluble positive feedback signal to induce cytokine production by either stromal or endothelial cells (Jazwiec et al., Leukemia 12, 1210–20, 1998). ARP may play such a role, with important implications for ex vivo stem cell expansion, cancer treatment and gene therapy. In the mammalian brain, ARP may further affect the stress-associated plasticity of neuron and glia properties, consistent with previous findings of the inventors of morphogenic activities for AChE-R in transfected glia (Karpel et al., J. Neurochem. 66, 114–23, 1996).

The stem cell survival and proliferative effects of ARP denote a previously unforeseen activity that is particular to the AChE-R protein yet distinct from the acetylcholine hydrolysis and cell-cell adhesion capacity characteristic of the core domain common to all AChE isoforms. The pronounced expression of AChE-R during early embryogenesis, further demonstrate the involvement of ARP in inducing the proliferation of other embryonic stem cells. Moreover, neural stem cells were shown to produce a variety of blood cell types in vivo (Bjornson et al. Science 283, 534–7, 1999).

The findings presented here suggest that ARP is involved in the induction of growth and expansion capacities of pluripotent stem cells from multi-tissue origins. The unique properties of this peptide and equivalent peptides can contribute toward the development of diverse human differentiating cell sources for biomedical and research purposes.

Example 11

AChE-R Effects on Hippocampal LTP Suggest Causal Involvement in Neuronal Stress Responses At the molecular level, psychological stress notably leads to fast yet long lasting modulation of gene expression. As for the genes concerning the cholinergic system, it has been shown that within one hour from acute stress, long lasting changes in cholinergic gene expression are facilitated [Kaufer et al. (1998) id ibid.]. This particularly refers to drastic elevation in the levels of the normally rare "readthrough" variant of acetylcholinesterase (AChE-R), coupled with down-regulation of acetylcholine synthesizing and packaging proteins, the enzyme CHAT and the associated vesicular acetylcholine transporter (vAChT). This feedback response presumably contributes to reduce ACh levels following stress. Another outcome of stress responses involves a sudden increase in proteolytic activities. This leads, among other effects, to the cleavage of the C-terminal peptide (ARP) from the "readthrough" core enzyme. Immunodetection using anti-ARP antibodies reveals an increase in AChE-R degradation products in the cerebrospinal fluid of patients under stress [Kaufer (2000) PhD thesis, Hebrew University of Jerusalem, Jerusalem]. Moreover as shown above, the injection of synthetic ARP by itself induces proliferation of hematopoietic progenitor cells and over-expression of bone marrow AChE-R within 24 hr [Grisaru et al. (2001) Molecular Medicine, 7, 93–105]. These recent observations raised the intriguing possibility that ARP also possesses physiological and behavioral functions. To test this working hypothesis, the effects on LTP of confined swim stress (1 hr after induction), were compared with those induced by ARP injection (24 hr post-treatment) and with transgenic mice over-expressing AChE-R.

Differential properties of ACHE variants in synaptic plasticity—Stress effects

The "readthrough" AChE variant is the sole AChE variant that is up-regulated under psychological stress. Therefore, the possibility that the immediate recovery from psychological stress, in light of the over-expression of the AChE "readthrough" form will affect the pattern of LTP, was explored.

Stress was induced by forcing mice to swim twice for 4 min, with 4 min interval, and 1 hr later slices were taken for LTP experiments. The Schaffer collaterals-CA1 synapse pathway was tested. Basal field potentials were recorded for 15 min at 0.033 Hz. LTP was then induced by 3 consecutive tetanic stimulations, each of 1-sec duration, at 50 Hz with 20 sec inter-stimulus intervals. After tetanization, the change in the slope of the post-synaptic field potential (PSP) was followed for up to 3 hrs.

Figure 14A:
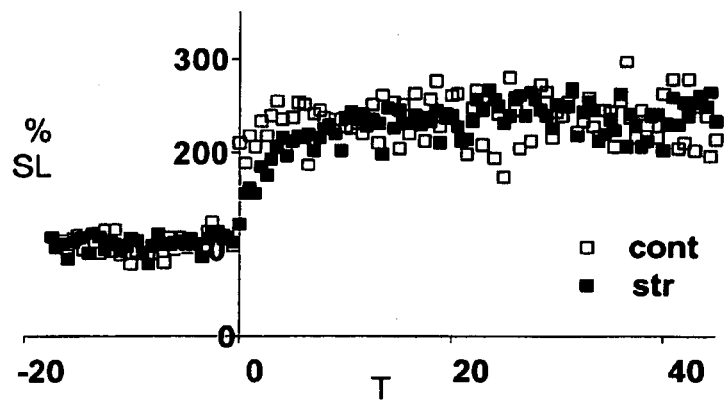

As shown in FIG. 14A, while slices from control mice exhibit a stepwise potentiation of 235±27% (n=3), the slices from stressed mice demonstrate a different pattern. LTP had a slow onset delayed by 5 to 20 min and reached a plateau of 238±18% (n=8) potentiation, similar in that respect to control levels.

Therefore, stress changes the onset of LTP, lagging the early phase, yet achieving a subsequent stable potentiation.

AChE-R Effects

Transgenic mice over-expressing the "readthrough" isoform AChE-R enabled direct examination of the question whether stress affects LTP, via elevation of AChE-R. Slices were prepared from adult control and transgenic mice, 3 to 5 months old, and LTP experiments were performed as described above.

Figure 14B:
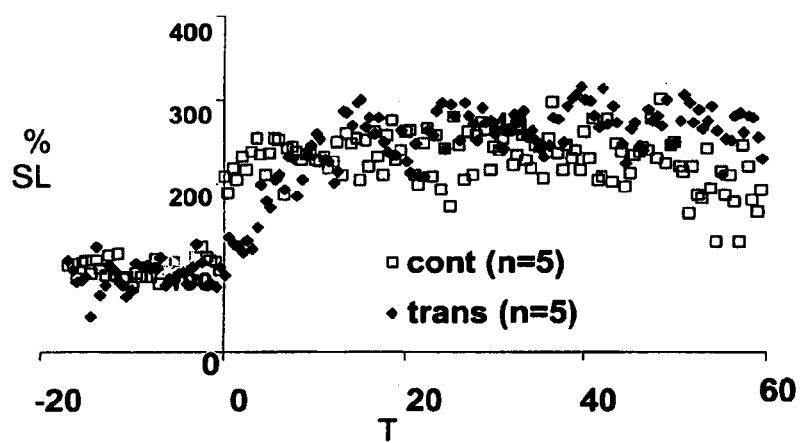

As shown in FIG. 14B, LTP in slices from transgenic mice over-expressing AChE-R shows the same pattern of slow onset as in the stress-induced mice (compare to FIG. 14A).

Injected ARP Effects

Figure 14C:
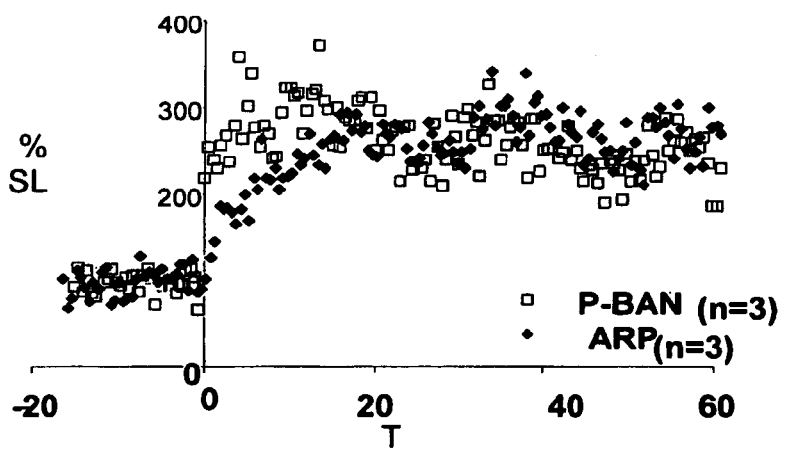

The option that ARP (the AChE Readthrough Peptide) serves as a stress signal was next examined. In case that ARP participates in signaling stress conditions by elevating the "readthrough" isoform in the CNS, as in the hematopoietic system, it would be expected to induce the LTP pattern that was observed under stress conditions or in the AChE-R transgenic mice (FIGS. 14A and 14B respectively). Therefore, mice were injected with ARP (i.p. 0.1 mg/Kg body weight) or with P-BAN, an irrelevant insect peptide of similar size. As shown in FIG. 14C, 24 hr later, the LTP pattern of 15 min slow onset repeated itself in the slices from the ARP injected animals but not from those injected with the control peptide.

In conclusion, these findings point at the proteolytic cleavage of ARP as a causally involved step in the synaptic responses to stress and suggesting existence of ARP binding sites in the hippocampus.

Moreover, these findings point at the possible mechanisms by which ARP might mediate such effects.

Example 12

Testicular Overproduction of the Stress-associated "readthrough" Acetylcholinesterase Variant Impairs Sperm Properties Suppressed male fertility is often attributed to stressful lifestyle, however, the protein(s) mediating such impairments are not yet known. Since ARP accumulation was observed under different stress situations, the contribution and the involvement of AChE-R in stress-induced infertility was next examined.

Testicular ACHE-R is Overexpressed in Psychologically Stressed Mice

The corticosterone levels and AChE activities were examined in testicular homogenates from FVB/N mice that were subjected to repeated acute psychological stress (4 successive daily sessions of confined swim). As shown in FIG. 15A, samples obtained from stressed mice displayed drastically elevated serum corticosterone levels and mildly increased AChE activities.

To study the pattern of AChE-R expression in stressed vs. untreated mice testis, in situ hybridization using a cRNA probe selective for the AChE-R mRNA transcript was performed on sections of testicular tubules from untreated FVB/N mice or from FVB/N mice subjected to 4 constitutive daily treatments of confined swim stress. As shown in FIG. 15B lower lane, the results revealed mild circumference labeling in testicular tubules from untreated FVB/N mice. Twenty-four hr after the last swim session, AChEmRNA labeling intensified and extended into several central cell layers, where spermatogonia are localized.

Similarly, Immunolabeling with an antibody selective for ARP, displayed no detectable staining in control mice, yet stained internal spermatid cell layers in tubuli of stressed mice (FIG. 15B-*top* lane).

Impaired Sperm Qualities under ACHE-R Excess Suggest Functional Significance to ARP To determine the in vivo capacity of ARP to affect different biochemical and physiological male fertility properties, the effect of injection of ARP or chronic expression of AChE-R (AChE-R transgenic mice) on different parameters was examined.

Twenty-four hours following injection of mice with 85 µg/kg ARP (but not PBS), blood corticosterone levels were doubled as compared with FVB/N mice or AChE-R transgenics (Table 4). While the mechanism(s) for such short-term glucocorticoid increases are yet unknown, this finding suggested that ARP might be independently involved in activating peripheral stress responses. Seminal gland weight was substantially reduced in AChE-R transgenics, but not in ARP injected mice, reinforcing the distinction between ARP and AChE-R effects; however, sperm counts were lower both in ARP-injected and in AChE-R transgenics than in untreated FVB/N mice. This did not reflect changes in cell division as the numbers of PCNA-positive cells in testicular tubules remained unchanged (Table 4). Intriguingly, sperm cells displayed significantly reduced motility in both ARP injected mice and AChE-R transgenics (Table 4) suggesting that ARP exerts rapid yet long lasting impairments of sperm properties.

TABLE 4

AChE-R over-expression impairs biochemical and physiological male fertility correlates

| general properties | Animals | | |
|---|---|---|---|
| | Control[a] | ARP injection[b] | AChE-R transgenics[c] |
| blood corticosterone, ng/ml | 31.6 ± 7.5 (3) | 58.1 ± 4.1 (3) | 31.7 ± 3.9 (3) |
| AChE activity, nmol ATCh/min/mg prot.[d] | 0.2 ± 0.06 (5) | 0.3 ± 0.06 (3) | 70.3 ± 1.1 (3) |
| seminal gland wt., mg/gr weight | 10.56 ± 0.95 (5) | 10.79 ± 1.08 (3) | 8.32 ± 0.28 (5) |
| sperm counts, cells/ epididimis × 10$^{-6}$ | 7.12 ± 0.35 (5) | 5.3 ± 1.2 (3) | 3.9 ± 0.4 (3) |
| sperm, motile, % of total sperm cells | 12 ± 3.0 (5) | 5 ± 1.7 (3) | 9 ± 2.3 (3) |
| anti-ARP area immuno stained/tubule perimeter, pixles[d] | None | 1.3 ± 0.5 (10) | 14.1 ± 1.7 (10) |
| PCNA positive cells/ tubule perimeter, no./pixles[e] | 26 ± 0.004 (20) | 28 ± 0.005 (12) | 28 ± 0.005 (20) |

[a]All tested animals were FVB/N adult mice, 2 to 4 month-old males (numbers shown in parentheses). Controls were untreated and PBS injected.
[b]24-hr post i.p. injection of 34 nmol/Kg ARP.
[c]Line 45 [Sternfeld et al. (1998a) id ibid].
[d]Average labeled cells or labeled areas for the noted (in parentheses) number of tubular sections and the identified antibodies.
Asterisks note significant difference (p < 0.05, Wilcoxon-Mann -Whitnety) from controls.

Corticosterone elevation initiates at the hypothalamic—pituitary-adrenal (HPA) axis, activated by calcium increases under psychological stress [Kaufer et al. (1999) *Current Opinion in Neurology* 12, 739–743]. The observed corticosterone and AChE-R overexpression following ARP injection suggest an HPA-activating, auto-regulatory function for ARP. AChE-R accumulation would induce the cell-cell or cell-substrate signaling capacities established for AChE [Grisaru et al.(1999b) id ibid.]. The normally rare AChE-R isoform differs from the major synaptic AChE-S variant in such properties, for example in cultured glia (Karpel et al J. Neurochem., 66, 114–123, 1996), supporting causal involvement for ARP in morphogenic functions. This calls for identifying the yet unknown brain protein partner(s) of ARP and the signal transduction mechanisms it activates.

Both Stress and ARP Injection Enhance ARP Immunolabeling of Spermatid Heads

To subcellularly localize the AChE-R isoform, immunolabeled mature spermatids from the central cavity of testicular tubules were subjected to confocal microscopy (FIG. 16). Anti-ARP antibodies failed to label spermatids from control mice, either naive or PBS-injected (FIG. 16A and data not shown). In contrast, either repeated acute stress (FIG. 16B) or a single ARP injection (FIG. 16C) induced clear intracellular punctuated labeling that was limited to spermatid heads and left their tails essentially unlabeled. The spermatids observed in the central cavity of AChE-R transgenics, with lower sperm cell counts, were only faintly labeled, again in heads but not tails.

Loss of ARP Immunolabeling in Human Sperm Heads from Subjects with Unexplained Couple Infertility To test the validity of the predictions based on the mice results, for human sperm properties, the inventors performed immunolabeling of ARP in smeared sperm cells from individuals with reported unexplained couple infertility. Healthy cells from sperm donations served as controls. Normal specimens were primarily co-stained in sperm head and midpiece regions. In contrast, sperm samples from male partners of couples with unexplained infertility displayed large fractions of cells labeling limited to the midpiece and unlabeled heads (FIG. 17A). Cumulative analysis demonstrated that these differences were statistically significant in that the midpiece alone was stained in 55% of sperm from couple infertility samples but only in 15% of normal donor sperm (FIG. 17B). Thus, alterations in ARP labeling patterns spanned both human and mouse sperm from subjects with impaired (or potentially impaired) sperm properties, as compared to their controls.

While reduced seminal gland weight could probably be attributed to the long-lasting effects of stress, the intensified labeling of developing sperm cells with anti-ARP antibodies suggests direct ARP effects on spermatogenesis and/or sperm properties. Focal perinuclear labeling of pachytene spermatocytes from AChE-R transgenics was associated with an apparent suppression of spermatogenesis manifested in reduced sperm counts. Transient excess, such as that induced following repeated acute stress or ARP injection, caused more limited impairments in spermatogenesis yet impaired sperm functioning most effectively. That this was associated with ARP accumulation was indicated from the modified ARP labeling of sperm heads in mice or midpiece and men.

Anti-ARP antibodies could label both ARP binding and AChE-R production sites. In stressed or ARP-affected mouse spermatids, the punctated head labeling appeared reminiscent of the mitochondrial distribution in the region surrounding spermatid heads. This assumption was supported by the intriguing labeling patterns in human sperm from infertile couples, where staining was most intense in the midpeice region which is enriched in mitochondria in primate sperm.

In summary, these results significantly indicate impaired sperm properties under overproduction of the stress-associated "readthrough" isoform of acetylcholin-esterase, AChE-R and its naturally cleaved C-terminal peptide ARP.

Thus, excess AChE-R and its C-terminal peptide ARP may suppress male fertility through both autonomous system regulation and direct sperm interactions.

Example 13

Detection of ARP Binding Proteins by using the Yeast Two-hybrid System

In order to study the possible signaling pathway through which ARP can exert its intracellular signaling leading to the observed proliferation and differentiation, screening for detection of ARP binding proteins was performed using the yeast 2-hybrid system.

The yeast 2-hybrid system is based on that transcription factors, such as GAL4, consist of two discrete modular domains: the DNA-binding domain (DNA-BD) and the activation domain (AD). A "bait" gene is expressed as a fusion to the DNA-BD, while a cDNA library is expressed as a fusion to the AD (Chien et al. (1991) id ibid; Fields et al. Trends Genet 10, 286–92, 1994). When the fusion proteins interact, the DNA-BD and AD brought into close proximity, thus reconstituting GAL4 and activating transcription of a reporter gene (FIG. 18A).

The bait is cloned into the DNA-BD vector where it is expressed as a fusion to amino acids 1–147 of the yeast GAL4 protein. A second gene or cDNA library is cloned into the AD vector, where it is expressed as a fusion to amino acids 768–881 of the yeast GAL4 protein. When the fusion proteins interact, the DNA-BD and AD domains are brought into close proximity and can activate transcription of reporter genes.

In order to identify AChE C-terminal peptide interacting proteins, the GAL4-based two-hybrid system was used. Sequences that encode AChE C-terminal peptides ARP and ASP were cloned into the DNA-BD pGBKT7 vector (Clonetech), (FIG. 18B) to serve as the bait. Three different cDNA libraries were cloned into the AD pGADT7 vectors and screened; adult and neonatal rat aorta and human fetal brain (Clontech).

Summary of the Yeast 2-Hybrid Preliminary Screens

Four preliminary yeast two-hybrid screens were performed, the outcomes of which are summarized below several points suggest that certain positive clones are meaningful.
1. The number of ARP positives in the developing rat aorta seems to be considerably higher than in the adult tissue, this is in line with the embryonic expression pattern of AChE-R.
2. Several positive clones appear more then once, representing independent cDNA chains of variable lengths.
3. In certain cases, the positives are logical candidates for AChE interactions (see below).

TABLE 5

Screening for Binding Partners

| Bait | Library | Independent clones in the library | Transfection efficiency | Number of positives on -Trp/-Leu/-Ade/-His |
|---|---|---|---|---|
| ASP | rat neonatal aort (SN) | $2.6 \times 10^6$ | 500,000 | 5 |
| r | rat adult aorta (AR) | $2 \times 10^6$ | 1,140,000 | 3 |
| ARP | human fetal brai (RB) | $1 \times 10^7$ | ~40,000 | 12 |
| ARP | rat neonatal aort (RN) | $2.6 \times 10^6$ | 880,000 | 29 |
| ASP | human fetal brain | $1 \times 10^7$ | | |

Candidate Partners:

During the first library screenings, 8 candidate partners emerged. Of these, a literature survey pointed to 2 candidates as most promising.

For ARP:
Fragment of AChE-ARP used for the two-hybrid screen Underlined is the actual ARP-peptide
PLEVRRGLRAQACAFWNRFLPKLLSAT GMQGPAGSGWEEGSGSPPGVTPLFSP, also denoted as SEQ ID: No. 7.
Receptor for Activated Protein Kinase C (RACK)—2 clones
*H. sapiens* melanoma antigen, family D, 1 (MAGED 1)—2 clones
*H. sapiens* guanine nucleotide-binding protein g(i)/g(s)/g(t) βsubunit 2 (transducin β chain 2)
*H. sapiens* duplicate spinal muscular atrophy—2 clones
*H. sapiens* peptidase D (PEPD)
*M. musculus* Eph receptor A6 (Epha6)
*H. sapiens* succinate dehydrogenase iron-protein subunit (sdhB) gene
*H. sapiens* mitogen-activated protein kinase 7 (MAPK7)
*H. sapiens* HLA-B associated transcript-3 (D6S52E) mitochondrial intermediate peptidase (MIP)
12-lipoxygenase For ASP:
Fragment of AChE-ASP used for the two-hybrid screen Underlined is the actual ASP-peptide:
PLEVRRGLRAQACAFWNRFLPKLLSAT DTLDEAERQWKAEFHRWSSYMVHWKNQFDH YSKQDRCSDL, also denoted as SEQ ID NO: 8.
Receptor for Activated Protein Kinase C (RACK)—2 clones (also showed up in the ARP screen, probably binds to the common part).
*H. sapiens* C-terminal binding protein 2 (CTBP2).
*H. sapiens* activating signal cointegrator 1.
*H. sapiens* colon carcinoma laminin-binding protein.
*H. sapiens* clusterin (complement lysis inhibitor, SP-40,40, sulfated glycoprotein 2, testosterone-repressed prostate message 2, apolipoprotein J) (CLU).
*H. sapiens* mRNA for silencer element.
*H. sapiens* heme-regulated initiation factor 2-α kinase (HRI).

Identification of RACK1 as ARP and ASP Interacting Molecule

One of the isolated partners, RACK1, was further analyzed for its ARP interactions. RACK1 is a cytoplasmic G protein homologue, which serves as a protein kinase C receptor.

Interaction between RACK1 and AChE may therefore be the link between AChE and other signaling molecules through which it exerts its non-catalytic intracellular functions.

Amino acid sequence alignment of RACK1 with the sequence obtained from the two-hybrid positive clone shows close to 100% homology (FIG. 19 and SEQ ID: No. 9). Furthermore, only part of the protein was expressed, which narrows the search to this part. Interestingly, the isolated sequence of this part of RACK includes peptides that were reported to be the binding sites of PKC to RACK1 (Ron et al., Proc Natl Acad Sci USA 91, 839–843, 1994)

Example 14

Overlay Assay Demonstrating the AChE-R-RACK1 Interaction

An in vitro overlay assay was combined with protein blot analysis to test for RACK1 interaction with the full AChE-R protein. RACK1 was expressed in *E. coli* and purified by affinity chromatography from *E. coli* as a fusion with maltose binding protein (MBP), and subsequently released from the fusion protein by proteolytic cleavage using factor Xa. Both cleaved and uncleaved preparations were used for the overlay assay. RACK1 samples were submitted to electrophoresis on a 4–10% denaturing polyacrylamide gel, blotted on a NC membrane, which was then stained with Ponceau (FIG. 20A), and stripped. Three identical strips were used for parallel experiments. Anti-RACK1 antibodies recognized the fusion protein, proteolytically-released RACK1 and fragments thereof, but not MBP (FIG. 20B). Parallel membranes were overlaid with a homogenate obtained from rat pheochromocytoma PC12 cells transfected with a plasmid encoding AChE-R [Seidman, S. et al.

(1995) id ibid.]. Antibodies to the N-terminus of human AChE (Santa Cruz) detected specific binding of AChE to the intact RACK1 protein on the overlaid membrane, but not to RACK1 degradation products or to MBP (FIG. 20C). The non-overlaid membrane did not reveal any interaction when incubated with these antibodies, demonstrating AChE-R dependence (FIG. 20D).

Example 15

Accumulation of a RACK1-Immunoreactivce Protein in the Mouse Post-Stress Brain

In order to study the expression of RACK1 in stress situation, homogenates from mouse hippocampus and cortex (composed of 3 stressed, 4–6 and 3 control, 1–3 mice) were separated on a denaturing gel and analyzed by immunoblot with anti-RACK1 antibody (FIG. 21). Surprisingly, a 50 kDa (apparent molecular weight) immunopositive band, which is much larger than normal RACK1 (36 kDa), was observed to accumulate following stress in both hippocampus and cortex. In parallel with the accumulation of this band, the normal sized RACK1 observed to be diminishing in the cortex. The intensity of the 50 kDa band strongly correlated with the plasma corticosterone levels of these mice. Thus, RACK1 increases in quantity in the post-stress mammalian brain, where it forms stable complex with yet unidentified protein(s).

Example 16

ARP1 Promotes Triple Complex Formation with RACK1 and PKCβII pGARP, a vector that encodes a fusion protein between green fluorescent protein (GFP) and ARP1 under the CMV promoter, was used to test whether ARP1 further promotes triple complex formation with PKCβII and RACK1 in mammalian cells (FIG. 22). When transfected into COS cells, which do not express AChE, anti-ARP antibodies immunodetected GARP expression in cell homogenates. Anti-GFP antibodies were ineffective in non-transfected cells but immunoprecipitated GARP, RACK1 and PKCβII from homogenates of GARP transfected COS cells (FIG. 22).

Example 17

AChE-R Promotes Triple Complexes with RACK1 and PKCβII in Native PC12 Cells

Both COS and PC12 cells express RACK1 and PKCβII constitutively, whereas only PC 12 expresses AChE-R, as observed in immunoblots of the soluble fraction of cell homogenates (FIG. 23A). Antibodies targeted to the N-terminal domain of AChE co-immunoprecipitated both PKCβII and RACK1 in PC12 but not COS cells, supporting the notion of tight binding for AChE-R/RACK1/PKCβII in these PC12 cell complexes (FIG. 23B).

Example 18

Stress Induces Neuronal Accumulation of Immunoreactive AChE-R and RACK1

The in vivo relevance of AChE-R/RACK1 interactions was explored in normal and post-stress mouse brain. Immunoreactive RACK1 was observed in the cytoplasm and closely proximal processes of pyramidal neurons, in layers 3 and 5 of the frontal and parietal cortex, in both superficial and deep layers of the piriform cortex, and in regions CA1 and CA3 of the hippocampus. A subset of these neurons also overexpresses AChE-R under acute psychological stress (FIG. 24 and data not shown). Stress-induced increase of RACK1 was seen in parietal cortex layer 5 (compare FIG. 24, C–E and G–I). Unlike RACK1, AChE-R antibodies also stained cells with glial morphology. Also, in some regions, such as hippocampal CA1, RACK1 staining formed an almost continuous pattern, whereas AChE-R was localized to a subset of pyramidal neurons. For both AChE-R and RACK1, uneven perikarial accumulation and increased neurite labeling were observed under stress (FIG. 24).

Example 19

Transgenic AChE-R Overexpression Elevates Brain RACK1 Levels and Intensifies the Formation of Neuronal PKCβII Clusters.

Hippocampal homogenates from AChE-R overexpressing transgenics [Sternfeld et al. (2000) id ibid.] were tested to investigate whether AChE-R overproduction would modulate the levels, properties and/or neuronal localization of its partner proteins RACK1 and PKCβII. The results show that the hippocampal homogenates displayed significant increases (compared to the levels in control FVB/N stress-prone mice) of neuronal AChE-R and RACK1, as well as a faster migrating PKCβII band that was only faintly detected in the hippocampus of a control animal (FIG. 25A).

Of the three target proteins, RACK1 and AChE-R appeared more widely distributed and could be detected in numerous brain regions (FIG. 25B and data not shown). In the brain of AChE-R transgenics, AChE-R overexpression was particularly conspicuous in neuron groups showing punctuated PKCβII staining (FIG. 25B–D). PKCβII labeling, in contrast, appeared higher than control levels in only a fraction of the AChE-R overexpressing subregions. Finally, RACK1 staining was intensified in the AChE-R expressing hippocampal CA1 and dentate gyrus neurons, and less prominent in the parietal cortex. This result suggested that the AChE-R/RACK1/PKCβII interactions facilitated the intracellular retention of the secretory AChE-R protein.

Example 20

Diverse Subcellular Distributions of PKCβII.

In control mice, PKCβII antibodies displayed diffuse staining [Weeber et al. (2000) id ibid.] in sub-regions of layers 5,6 in the cortex, in the stratum oriens and stratum radiatum layers of the hippocampus CA1 field, in the striatum matrix, and in the substantia nigra pars reticulata. Axonal bundles including the nigro-striatal tract were also labeled (data not shown). Another and novel staining pattern consisted of dense PKCβII clusters in neuronal perikaria and in the axonal stems. This punctiform pattern appeared in upper layers of the parietal, temporal and piriform cortex, dorsal striatum, basolateral amygdala, hippocampal CA1 and lateral septum. In general, cells in AChE-R transgenic mice that displayed prominent AChE-R labeling were positive for RACK1 and presented PKCβII punctiform staining (FIG. 25B–E). AChE-R labeling in cells where in control mice included AChE-R, RACK1 and punctated PKCβII, was not intensified in AChE-R transgenic mice. These included neurons in the globus pallidus, substantia nigra, superior culliculus, medial septum and diagonal band (FIG. 25B–E and data not shown). Other neurons were positive for AChE-R staining in the control mice, and yet more so in AChE-R transgenic mice, but had no PKCβII punctiform staining. These resided in the lateral and ventro-medial hypothalamus, central nucleus of the amygdala, the hippocampal dentate gyrus, ventro-lateral thalamus, and the Edinger-Westphal nucleus (FIG. 25C, D). C57B6J mice were tested for the punctated staining pattern, and a weaker but discernible punctiform signal was observed in the same cell populations as in the stress-prone FVB/N strain, used as control (data not shown).

Example 21

Inter-related AChE-R/RACK1/PKCβII Distributions

In samples obtained from AChE-R transgenic mice, anti-PKCβII antibodies detected diffuse and axonal staining patterns similar to those observed in the parental FVB/N strain. However, the punctated pattern was altered. Stronger and denser clusters of PKCβII staining were located on the perikaryal circumference of a larger fraction of hippocampal CA1 neurons (FIG. 25E2). Transgenic mice overexpressing the major synaptic isoform of AChE [Beeri, R. et al. (1995) Curr Biol, 5, 1063–71] did not show such changes in PKCβII expression (data not shown), suggesting that this in vivo effect depended on chronic AChE-R excess and/or that it was prevented by AChE-S excess. AChE-R staining in the transgenic brain was prominent in the cell bodies and proximal processes of many, but not all CA1 hippocampal neurons, suggesting that a specific subset of these neurons was especially amenable for such accumulation (FIG. 25E-3,4). Sparse cells with morphology reminiscent of microglia were also positive for AChE-R staining, both in control and transgenic animals (FIG. 25E-5, 6). Intensified labeling of perikaria and closely proximal neurites of CA1 pyramidal neurons was also observed by staining with RACK1 antibodies (FIG. 256E-3, 4).

Example 22

Subcellular Distributions of AChE-R, RACK1 and PKCβII was Overlapping

Confocal micrographs of upper layer neurons from the parieto-temporal cortex double labeled with antibodies against AChE-R and RACK1 or PKCβII displayed distinct yet overlapping distributions for the three partner proteins within neuronal perikarya in compound field projections. As expected, AChE-R labeling was conspicuously more intense in AChE-R transgenics than in FVB/N controls (compare in FIGS. 26B-1 to 4 and 26C-7 to 10). The overexpression and the associated overlapping increases in the two partner proteins were reflected in different colors (FIGS. 26B and C).

Proteins destined to be secreted are initially concentrated near the nucleus, where their processing takes place, whereas proteins that are associated with the perikaryal cytoskeleton, plasma membrane and/or proximal process structures are distributed more peripherally in the cell. In cortical neurons from control mice, both AChE-R and RACK1 immunostaining formed peri-nuclear accumulations (compare in FIG. 26B-1 to 3). In contrast, the intensity of RACK1 staining in AChE-R transgenic mice was especially high around the perikaryal circumference (compare in FIGS. 26B-2 and 5), suggesting subcellular translocation under AChE-R excess. PKCβII staining clusters were also removed from the peri-nuclear domain in the control mice (FIGS. 26C-8), and showed uneven distribution in larger cellular spaces in transgenic mice (FIGS. 26C-11). In control mice, PKCβII patterns differed from both those of AChE-R and RACK1 in that they demonstrated both diffuse staining and punctated clusters of protein complexes, compatible with the parallel light microscopy patterns. Constitutive AChE-R overexpression further enlarged the perikaryal space occupied by AChE-R, RACK1 and PKCβII and seemed to increase the intracellular density of their complexes.

The invention claimed is:

1. An isolated regulatory peptide consisting of an amino acid sequence as denoted by SEQ ID NO: 1, wherein said peptide promotes cell growth or cell differentiation or both, and wherein said peptide corresponds to the C-terminal region of the readthrough variant of acetylcholinesterase.

2. A synthetic peptide consisting of the amino acid sequence as denoted by SEQ ID NO: 1.

3. The peptide according to any one of claims 1 and 2, consisting of the amino acid sequence as denoted by SEQ ID NO: 1.

4. A synthetic peptide consisting of the amino acid sequence as denoted by SEQ ID NO:1, which peptide promotes cell growth or cell differentiation or both, and corresponds to the C-terminal region of the readthrough variant of acetylcholinesterase, wherein said peptide is linear.

5. A synthetic peptide consisting of the amino acid sequence as denoted by SEQ ID NO:1, which peptide promotes cell growth or cell differentiation or both, and corresponds to the C-terminal region of the readthrough variant of acetyicholinesterase, wherein said peptide is cyclic.

6. The peptide according to any one of claims 1 to 3, wherein said peptide promotes cell survival.

7. The peptide according to any one of claims 1 to 3, which is any one of hematopoietic stem cell growth peptide and differentiation regulatory peptide.

8. The peptide according to claim 6, wherein said peptide promotes stem cell survival or myeloid and megakaryocytic differentiation, or both.

9. The peptide according to claim 6, wherein said peptide promotes endothelial cell growth.

10. A method of ex vivo and in vivo expansion of hematopoietic stem cells, comprising contacting said cells with the regulatory peptide according to claim 6.

11. The method according to claim 10, wherein said regulatory peptide has the amino acid sequence as denoted by SEQ ID NO:1.

12. A method of ex vivo and in vivo promotion of megakaryocytic differentiation of hematopoietic stem cells, comprising contacting said cells with the peptide according to claim 7.

13. The method according to claim 11, wherein said peptide has the amino acid sequence as denoted by SEQ ID NO:1.

14. A method for promoting hematopoietic stem cell survival and/or myeloid and megakaryocytic differentiation, comprising contacting said cells with the peptide according to claim 7.

15. A method for promoting endothelial cell growth, comprising contacting hematopoietic stem cells with the peptide according to claim 8.

* * * * *

UNITED STATES PATENT AND TRADEMARK OFFICE
CERTIFICATE OF CORRECTION

PATENT NO. : 7,067,486 B2  Page 1 of 1
APPLICATION NO. : 09/998042
DATED : June 27, 2006
INVENTOR(S) : Hermona Soreq et al.

It is certified that error appears in the above-identified patent and that said Letters Patent is hereby corrected as shown below:

In the drawings, Sheet 5, Fig. 4A, the last two amino acid residues (Asp "D" and Leu "L") at the terminus were missing. The portion of Figure 4A reading "ASP: DTLDEAERQWKAEFHRWSSYMVHWKNQFDHYSKQDRCS" should appear as --ASP: DTLDEAERQWKAEFHRWSSYMVHWKNQFDHYSKQDRCSDL--.

Signed and Sealed this

Fourth Day of May, 2010

David J. Kappos
*Director of the United States Patent and Trademark Office*

SEQUENCE LISTING

```
<160> NUMBER OF SEQ ID NOS: 9

<210> SEQ ID NO 1
<211> LENGTH: 26
<212> TYPE: PRT
<213> ORGANISM: HOMO SAPIENS

<400> SEQUENCE: 1

Gly Met Gln Gly Pro Ala Gly Ser Gly Trp Glu Glu Gly Ser Gly Ser
 1               5                  10                  15

Pro Pro Gly Val Thr Pro Leu Phe Ser Pro
            20                  25

<210> SEQ ID NO 2
<211> LENGTH: 40
<212> TYPE: PRT
<213> ORGANISM: HOMO SAPIENCE

<400> SEQUENCE: 2

Asp Thr Leu Asp Glu Ala Glu Arg Gln Trp Lys Ala Glu Phe His Arg
```

```
                1               5              10              15
Trp Ser Ser Tyr Met Val His Trp Lys Asn Gln Phe Asp His Tyr Ser
                        20                  25                  30

Lys Gln Asp Arg Cys Ser Asp Leu
                35                  40

<210> SEQ ID NO 3
<211> LENGTH: 27
<212> TYPE: PRT
<213> ORGANISM: HOMO SAPIENS

<400> SEQUENCE: 3

Phe His Arg Trp Ser Ser Tyr Met Val His Trp Lys Asn Gln Phe Asp
  1               5                  10                  15

His Tyr Ser Lys Gln Asp Arg Cys Ser Asp Leu
                20                  25

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence:5' primer
      for intron 4 of human acetylcholinesterase

<400> SEQUENCE: 4
gctggatcca tcgaggggcg aggtatgcag gggccagcgg gc                         42

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:3' primer
      for intron 4 of human acetylcholinesterase

<400> SEQUENCE: 5
tataagcttc taggggaga agagagggt                                         30

<210> SEQ ID NO 6
<211> LENGTH: 37
<212> TYPE: PRT
<213> ORGANISM: homo sapiens

<400> SEQUENCE: 6

Asn Arg Phe Leu Pro Lys Leu Leu Ser Ala Thr Gly Met Gln Gly Pro
  1               5                  10                  15

Ala Gly Ser Gly Trp Glu Glu Gly Ser Gly Ser Pro Pro Gly Val Thr
                20                  25                  30

Pro Leu Phe Ser Pro
                35

<210> SEQ ID NO 7
<211> LENGTH: 53
<212> TYPE: PRT
<213> ORGANISM: Artificial Sequence
<220> FEATURE:
<223> OTHER INFORMATION: Description of Artificial Sequence:arp-two
      hybrid screen peptide

<400> SEQUENCE: 7

Pro Leu Glu Val Arg Arg Gly Leu Arg Ala Gln Ala Cys Ala Phe Trp
  1               5                  10                  15
```

-continued

Asn Arg Phe Leu Pro Lys Leu Leu Ser Ala Thr Gly Met Gln Gly Pro
            20                  25                  30

Ala Gly Ser Gly Trp Glu Gly Ser Gly Ser Pro Pro Gly Val Thr
            35                  40                  45

Pro Leu Phe Ser Pro
        50

<210> SEQ ID NO 8
<211> LENGTH: 67
<212> TYPE: PRT
<213> ORGANISM: Artificial Sequence
<220> FEATURE:
<223> OTHER INFORMATION: Description of Artificial Sequence:
      ASP - peptide for two-hybrid screen

<400> SEQUENCE: 8

Pro Leu Glu Val Arg Arg Gly Leu Arg Ala Gln Ala Cys Ala Phe Trp
 1               5                  10                  15

Asn Arg Phe Leu Pro Lys Leu Leu Ser Ala Thr Asp Thr Leu Asp Glu
            20                  25                  30

Ala Glu Arg Gln Trp Lys Ala Glu Phe His Arg Trp Ser Ser Tyr Met
            35                  40                  45

Val His Trp Lys Asn Gln Phe Asp His Tyr Ser Lys Gln Asp Arg Cys
        50                  55                  60

Ser Asp Leu
 65

<210> SEQ ID NO 9
<211> LENGTH: 317
<212> TYPE: PRT
<213> ORGANISM: Artificial Sequence
<220> FEATURE:
<223> OTHER INFORMATION: Description of Artificial Sequence:homology of
      ARP and RACK

<400> SEQUENCE: 9

Met Thr Glu Gln Met Thr Leu Arg Gly Thr Leu Lys Gly His Asn Gly
 1               5                  10                  15

Trp Val Thr Gln Ile Ala Thr Thr Pro Gln Phe Pro Asp Met Ile Leu
            20                  25                  30

Ser Ala Ser Arg Asp Lys Thr Ile Ile Met Trp Lys Leu Thr Arg Asp
            35                  40                  45

Glu Thr Asn Tyr Gly Ile Pro Gln Arg Ala Leu Arg Gly His Ser His
        50                  55                  60

Phe Val Ser Asp Val Val Ile Ser Ser Asp Gly Gln Phe Ala Leu Ser
 65                  70                  75                  80

Gly Ser Trp Asp Gly Thr Leu Arg Leu Trp Asp Leu Thr Thr Gly Thr
            85                  90                  95

Thr Thr Arg Arg Phe Val Gly His Thr Lys Asp Val Leu Ser Val Ala
            100                 105                 110

Phe Ser Ser Asp Asn Arg Gln Ile Val Ser Gly Ser Arg Asp Lys Thr
            115                 120                 125

Ile Lys Leu Trp Asn Thr Leu Gly Val Cys Lys Tyr Thr Val Gln Asp
        130                 135                 140

Glu Ser His Ser Glu Trp Val Ser Cys Val Arg Phe Ser Pro Asn Ser
145                 150                 155                 160

Ser Asn Pro Ile Ile Val Ser Cys Gly Trp Asp Lys Leu Val Lys Val
            165                 170                 175

-continued

```
Trp Asn Leu Ala Asn Cys Lys Leu Lys Thr Asn His Ile Gly His Thr
            180             185             190

Gly Tyr Leu Asn Thr Val Thr Val Ser Pro Asp Gly Ser Leu Cys Ala
        195             200             205

Ser Gly Gly Lys Asp Gly Gln Ala Met Leu Trp Asp Leu Asn Glu Gly
    210             215             220

Lys His Leu Tyr Thr Leu Asp Gly Gly Asp Ile Ile Asn Ala Leu Cys
225             230             235             240

Phe Ser Pro Asn Arg Tyr Trp Leu Cys Ala Ala Thr Gly Pro Ser Ile
            245             250             255

Lys Ile Trp Asp Leu Glu Gly Lys Ile Met Val Asp Glu Leu Lys Gln
            260             265             270

Glu Val Ile Ser Thr Ser Ser Lys Ala Glu Pro Pro Gln Cys Thr Ser
        275             280             285

Leu Ala Trp Ser Ala Asp Gly Gln Thr Leu Phe Ala Gly Tyr Thr Asp
    290             295             300

Asn Leu Val Arg Val Trp Gln Val Thr Ile Gly Thr Arg
305             310             315
```